(12) United States Patent
Valtakari et al.

(10) Patent No.: US 9,404,164 B2
(45) Date of Patent: Aug. 2, 2016

(54) PROTEASE ENZYME AND USES THEREOF

(75) Inventors: Leena Valtakari, Rajamäki (FI); Kari Juntunen, Espoo (FI); Marja Paloheimo, Vantaa (FI); Pentti Ojapalo, Tuusula (FI)

(73) Assignee: AB Enzymes Oy, Rajamäki (FI)

( * ) Notice: Subject to any disclaimer, the term of this patent is extended or adjusted under 35 U.S.C. 154(b) by 0 days.

(21) Appl. No.: 13/433,984

(22) Filed: Mar. 29, 2012

(65) Prior Publication Data
US 2012/0252064 A1 Oct. 4, 2012

Related U.S. Application Data

(60) Provisional application No. 61/470,168, filed on Mar. 31, 2011.

(30) Foreign Application Priority Data

Mar. 31, 2011 (FI) ..................................... 20115310

(51) Int. Cl.
*C12N 9/58* (2006.01)
*C11D 3/386* (2006.01)

(52) U.S. Cl.
CPC ............... *C12Y 304/21* (2013.01); *C11D 3/386* (2013.01); *C12N 9/58* (2013.01)

(58) Field of Classification Search
None
See application file for complete search history.

(56) References Cited

U.S. PATENT DOCUMENTS

| | | | |
|---|---|---|---|
| 3,652,399 A | 3/1972 | Isono et al. | |
| 5,288,627 A | 2/1994 | Nielsen et al. | |
| 5,770,418 A | 6/1998 | Yaver et al. | |
| 5,843,745 A | 12/1998 | Berka et al. | |
| 5,962,765 A | 10/1999 | St. Leger et al. | |
| 6,300,116 B1 * | 10/2001 | von der Osten et al. | 435/220 |
| 6,573,086 B1 | 6/2003 | Emalfrab et al. | |
| 6,682,924 B1 | 1/2004 | Sierkstra et al. | |
| 2004/0023355 A1 | 2/2004 | Sierkstra et al. | |
| 2010/0120649 A1 | 5/2010 | Andersen | |
| 2011/0003729 A1 | 1/2011 | Juntunen et al. | |
| 2011/0008870 A1 | 1/2011 | Makinen et al. | |
| 2011/0028375 A1 | 2/2011 | Juntunen et al. | |
| 2012/0107905 A1 | 5/2012 | Juntunen et al. | |

FOREIGN PATENT DOCUMENTS

| | | |
|---|---|---|
| EP | 0244234 | 11/1987 |
| EP | 0352244 A2 | 1/1990 |
| EP | 0290567 | 6/1992 |
| EP | 0290569 | 6/1992 |
| EP | 0519229 A2 | 12/1992 |
| EP | 0 479 870 | 10/2000 |
| EP | 1347045 | 9/2003 |
| EP | 1464626 A2 | 10/2004 |
| EP | 1870453 A1 | 12/2007 |
| EP | 1 009 815 | 1/2008 |
| EP | 1464626 B1 | 11/2009 |
| WO | 88/03946 | 6/1988 |
| WO | 88/07581 | 10/1988 |
| WO | 89/04361 | 5/1989 |
| WO | 89/06270 | 7/1989 |
| WO | 92/03529 | 3/1992 |
| WO | 92/05239 | 4/1992 |
| WO | 92/18599 | 10/1992 |
| WO | 94/25583 | 11/1994 |
| WO | 96/18722 | 6/1996 |
| WO | 97/02753 | 1/1997 |
| WO | 97/08325 | 3/1997 |
| WO | 97/28243 | 8/1997 |
| WO | 98/20116 | 5/1998 |
| WO | 02/08398 | 1/2002 |
| WO | 2006/073839 | 7/2006 |
| WO | 2007/145963 | 12/2007 |
| WO | 2008/045148 | 4/2008 |
| WO | 2009/096916 | 8/2009 |
| WO | 2010/039840 | 4/2010 |
| WO | 2010/125174 | 11/2010 |
| WO | 2010/125175 | 11/2010 |
| WO | 2011/003968 | 1/2011 |

OTHER PUBLICATIONS

Beg QK et al. (2003). Purification and characterization of an oxidation-stable, thiol-dependent serine alkaline protease from Bacillus mojavensis. Enzyme and Microbial Technology, v32, p. 294-304.*
Gayle RB et al. (1993). Identification of Regions in Interleukin—1a Important for Activity. The Journal of Biological Chemistry, v268(29), p. 22105-22111.*
Whisstock JC et al. (2003). Prediction of protein function from protein sequence and structure. Quarterly Reviews of Biophysics, v36(3), p. 307-340.*
Venalainen JI et al. (2004). Evolutionary relationships of the prolyl oligopeptidase family enzymes. European Journal of Biochemistry, v271, p. 2705-2715.*
Lewis et al. (1967). Sugar Alcohols (Polyols) in Fungi and Green Plants. I. Distribution, Physiology and Metabolism. New Phytol, v66, ; Reference U.*
International Search Report issued in PCT/EP2012/055762 dated Sep. 25, 2012, 5 pages.

(Continued)

*Primary Examiner* — Scott Long
*Assistant Examiner* — Sean C Barron
(74) *Attorney, Agent, or Firm* — Fish & Richardson P.C.

(57) ABSTRACT

The present invention is related to a fungal serine protease enzyme, which said enzyme has serine protease activity and comprises an amino acid sequence of *Malbranchea* ALKO4122 mature protease as defined in SEQ ID NO:18 or an amino acid sequence having at least 66% identity to the amino acid sequence of SEQ ID NO:18. Also disclosed is an isolated nucleic acid molecule, comprising a polynucleotide sequence which encodes a fungal serine protease enzyme, nucleic acid sequences encoding said protease, a host cell and a process of producing a polypeptide having serine protease activity. Said protease is useful as an enzyme preparation applicable in detergent compositions and for treating fibers, wool, hair, leather, or silk, for treating food or feed, or for any applications involving modification, degradation or removal of proteinaceous material.

19 Claims, 18 Drawing Sheets

(56) References Cited

OTHER PUBLICATIONS

Written Opinion issued in PCT/EP2012/055762 dated Sep. 25, 2012, 7 pages.
Ong et al., "Production, purification and characterization of thermomycolase, the extracellular serine protease of the thermophilic fungus *Malbranchea pulchella* var. *sulfurea*," Can. J. Microbiol., 22:165-176 (1976).
Sharpton et al., "Comparative genomic analyses of the human fungal pathogens *Coccidioides* and their relatives," Genome Research, 19(10): 1722-1731 (2009).
Stevenson et al., "The Substrate Specificity of Thermomycolase, an Extracellular Serine Proteinase from the Thermophilic Fungus *Malbranchea pulchella* var. *sulfurea*," Biochem. J., 151(3):527-542 (1975).
Uniprot database [Online], Database Accession No. C5PCX1, Sep. 1, 2009, from Sharpton et al., "Comparative genomic analyses of the human fungal pathogens *Coccidioides* and their relatives," Genome Research, 19(10): 1722-1731 (2009), 2 pages.
Abu-Shady, M. R. et al., "Production, Partial Purification and Some Properties of Thermostable Alkaline Protease from *Malbranchea sulfurea* and its Compatibility with Commercial Detergents", *Afr. J. Mycol. And Biotech.*, vol. 9, No. 3, (2001), pp. 17-26.
D'Acunzo, F. et al., "Oxidation of phenols by laccase and laccase-mediator systems", Eur. J. Biochem., vol. 269, (2002), pp. 5330-5335.
Fabbrini, M. et al., "Comparing the catalytic efficiency of some mediators of lacasse", Journal of Molecular Catalysis B: Enzymatic, vol. 16, (2002), pp. 231-240.
Genbank Acc#AAA34209 from Geremia et al., Mol Microbiol May 1993;8(3):603-613. Alignment with Seq ID No. 10 of U.S. Appl. No. 12/803,456 (3 pages).
Liao, J. et al., "Engineering proteinase K using machine learning and synthetic genes", BMC Biotechnology, vol. 7, No. 16, (2007), pp. 1-19.
Uniprot 201110 database Acc# A4V8W7_TRIHA from Suarez et al., Curr Genet. May 2007; 51(5):331-42, Epub Apr. 6, 2007., Alignment with Seq ID No. 18 of U.S. Appl. No. 12/799,638 (2 pages).
Uniprot database Acc# Q86ZV3_TRIHM from Steyaert et al., Mycologia 96: 1245-1252 (2004). Alignment with Seq ID No. 10 of U.S. Appl. No. 12/803,456 (2 pages).
USPTO in house alignment Q86ZV3_TRIHM from Steyaert et al. Mycologia 96:1245-1252 (2004) Alignment with Seq ID No. 10 of U.S. Appl. No. 12/803,456 (1 page).
USPTO in house alignment AAA34209 from Geremia et al., Mol. Microbiol. May 1993;8(3):603-613. Alignment with Seq ID No. 10 for U.S. Appl. No. 12/803,456 (1 page).
Search Report issued in the corresponding Finnish Patent Application No. 20106135 dated May 13, 2011 (1 page).
Altschul, S. F. et al., "Basic Local Alignment Search Tool", J. Mol. Biol., vol. 215, (1990), pp. 403-410.
AMFEP, Association of Manufacturers and Formulators of Enzyme products, List of enzymes at http://www.amfep.org/list.html (updated Oct. 2009).
Antal, Z. S. et al,, "Colony growth, in vitro antagonism and secretion of extracellular enzymes in cold-tolerant strains of *Trichoderma* species", Mycol. Res,, vol. 5, (2000), pp. 545-549.
Anwar, A. et al., "Alkaline Proteases: A Review", Bioresource Technology, vol. 64, (1998), pp. 175-183.
Banerjee, U. C. et al., "Thermostable alkaline protease from Bacillus brevis and its characterization as a laundry detergent additive", Process Biochemistry, vol. 35, (1999), pp. 213-219.
Bolton, E. T. et al., "A General Method for the Isolation of RNA Complementary to DNA", Proc. Nat. Acad. Sci. USA, vol. 48, (1962), pp. 1390-1397.
Chen, Y-J. et al., "The intramolecular chaperone-mediated protein folding", Current Opinion in Structural Biology, Vol, 18, (2008), pp. 765-770.
Cherry, J. R. et al., "Directed evolution of industrial enzymes: an update", Current Opinion in Biotechnology, vol. 14, (2003), pp. 438-443.
Dienes, D. et al., "Identification of a trypsin-like serine protease from Trichoderma reesei GM9414", Enzyme and Microbial Technology, vol. 40, (2007), pp. 1087-1094.p-.
Edman, P. et al., "A Protein Sequenator", European J. Biochem., vol. 1, (1967), pp. 80-91.
EMBL database (online), Database Accession No. DR657362, Jul. 14, 2005, from Brown, D. W., et al., "Analysis of 87,000 expressed sequence tags reveals alternatively spliced introns in multiple genes of the fumonisin gene cluster", (Unpublished) (1 page).
EMBL database (online), Database Accession No. BI750343, Jun. 15, 2004, from Harris, L. J. et al. "Expressed Sequence Tags from Fusarium graminearum mycelium", (Unpublished) (1 page).
EMBL database (online), Database Accession No. AM294980, Apr. 20, 2007, from Suarez, M. B., et al., "Characterization of genes encoding novel peptidases in the biocontrol fungus *Trichoderma harzianum* CECT 2413 using the TrichoEST functional genomics approach", Curr. Genet. vol. 51, No. 5, (2007), pp. 331-342 (2 pages).
European Patent Office database (online), Database Accession No. HC687299, May 10, 2010, from Shasky, J. et al., "Methods for producing polypeptides in enzyme-deficient mutants of fusarium venenatum; Sequence 84 from Patent WO2010039840", Patent No. WO2010039840-A1, Apr. 8, 2010 (1 page).
European Patent Office database (online), Database Accession No. GM007507, Nov. 20, 2008, from Madison, E.L., "Protease screening methods and proteases identified thereby"; Sequence 313 from Patent No. WO2008045148-A1, Apr. 17, 2008 (1 page).
Gasteiger, E. et al., "ExPASy: The proteomics server for in-depth protein knowledge and analysis", Nucleic Acids Research, vol. 31, No. 13, (2003), pp. 3784-3788.
Gaucher, G. M. et al. "567. Thermomycolin", Handbook of Proteolytic Enzymes, (2004), pp. 1834-1835.
Gayle, R. B. et al., "Identification of Regions in Interleukin-1α Important for Activity", The Journal of Biological Chemistry, vol. 268, No. 29, (1993), pp. 22105-22111.
Genbank database, Database Accession No. AAA34209.1, May 28, 1993, from Geremia, R.A. et al., "Molecular Characterization of the proteinase-encoding gene, prbl, related to mycoparasitism by Trichoderma harzianum", Molecular Microbiology, vol. 8, No. 3, (1993), pp. 603-613 (3 pages).
Geremia, R. A. et al., "Molecular characterization of the proteinase-encoding gene, prbl, related to mycoparasitism by Trichoderma harzianum", Molecular Microbiology, vol. 8, No, 3, (1993), pp. 603-613.
Gupta, R. et al., "An overview on fermentation, downstream processing and properties of microbial alkaline protease", Appl. Microbiol. Biotechnol., vol. 60, (2002), pp. 381-395.
Gurr, S. J, et al., "The structure and organization of nuclear genes in filamentous fungi", Kinghorn, Jr. (ed.), Gene Structure in Eukaryotic Microbes, IRL Press, Oxford, (1987), pp. 93-139.
Joutsjoki, V. V. et al., "Transformation of Trichoderma reesei with the Hormoconis resinae glucoamylase P (gamP) gene: production of a heterologous glucoamylase by Trichoderma reesei", Current Genetics, vol. 24, (1993), pp. 223-228.
Kalisz, H. M., "Microbial Proteinases", Advances in Biochemical Engineering/Biotechnology, vol. 36, (1988), pp. 1-65.
Karhunen, T. et al., "High frequency one-step gene replacement in Trichoderma reesei. I. Endoglucanase I overproduction", Mol. Gen, Genet., vol. 241, (1993), pp. 515-522.
Kelly, J. M. et al., "Transformation of Aspergillus niger by the amdS gene of Aspergillus nidulans", The EMBO Journal, vol. 4, No. 2, (1985), pp. 475-479.
Kredics, L. et al., "Extracellular Proteases of Trichoderma Species", Acta Microbiologica et Immunologica Hungarica, vol. 52, No. 2, (2005), pp. 169-184.
Laemmli, U. K., "Cleavage of Structural Proteins during the Assembly of Head of Bacteriophage T4", Nature, vol. 227, (1970), pp. 680-685.
Malardier, L., et al., "Cloning of the nitrate reductase gene (niaD) of Aspergillus nidulans and its use for transformation of Fusarium oxysporum", Gene, vol. 78, (1989), pp. 147-156.

(56) References Cited

OTHER PUBLICATIONS

Manonmani, H.K. et al. "Purification and properties of an extracellular proteinase of Trichoderma koningii", Enzyme Microb. Technol., vol. 15, (1993), pp. 624-628.

Martinez, D. et al., "Gene sequencing and analysis of the biomass-degrading fungus Trichoderma reesei (syn. *Hypocrea jecorina*)", Nature Biotechnology, vol. 26., No. 5, (2008), pp. 553-560.

Maurer, K. H., "Detergent proteases", Curr. Opin. Biotechnol., vol. 15, (2004), pp. 330-334.

Maurer, K. H. et al. "Enzymes, Detergent", Encyclopedia of Industrial Biotechnology: Bioprocess, Bioseparation, and Cell Technology (Michael C. Flickinger, ed.), John Wiley & Sons, Inc., (2010), pp. 1-17.

NCBI REFSEQ Database (online), Database Accession No. XP_383491, Apr. 9, 2008, No Author Found, Hypothetical protein FG03315.1 (Gibberella zeae PH-1) (1 page).

Nielsen, H. et al., Short Communication, "Identification of prokaryotic and eukaryotic signal peptides and prediction of their cleavage sites", Protein Engineering, vol. 10, No. 1, (1997), pp. 1-6.

Nielsen, H. et al., "Prediction of signal peptides and signal anchors by a hidden Markov model", In: Proceedings of the Sixth International Conference on Intelligent Systems for Molecular Biology (ISMB 6), AAAI Press, Menlo Park, California, (1998), pp. 122-130.

Ong, P. S. et al., "Production, purification and characterization of thermomycolase, the extracellular serine protease of the thermophilic fungus *Malbranchea pulchella* var. sulfurea", Can. J. Microbiol., vol. 22, (1975), pp. 165-175.

Paloheimo, M. et al., "High-Yield Production of a Bacterial *Xylanase* in the Filamentous Fungus *Trichoderma reesei* Requires a Carrier Polypeptide with an Intact Domain Structure", applied and Environmental Microbiology, vol. 69, No. 12, (2003), pp. 7073-7082.

Penttilä, M. et al., "A versatile transformation system for the cellulolytic filamentous fungus *Trichoderma reesei*", Gene, vol. 61, (1987), pp. 155-164.

Poutanen, P. et al., "Use of matrix-assisted laser desorption/ionization time-of-flight mass mapping and nanospray liquid chromatography/electrospray ionization tandem mass spectrometry sequence tag analysis for high sensitivity identification of yeast proteins separated by two-dimensional gel electrophoresis", Rapid Communications in Mass Spectrometry, vol. 15, No. 18, (2001), pp. 1685-1962.

Pozo, M. J., "Functional analysis of tvspl, a serine protease-encoding gene in the biocontrol agent Trichoderma virens", Fungal Genetics and Biology, vol. 41, (2004), pp. 336-348.

Raeder, U. et al., "Rapid preparation of DNA from filamentous fungi", Letters in Applied Microbiology, vol. 1, (1985), pp. 17-20.

Rao, M. B. et al., "Molecular and biotechnological Aspects of Microbial Proteases", Microbiology and Molecular Biology Reviews, vol. 62, No. 3, (1998), pp. 597-635.

Sambrook, J. and Russell, D. W., Molecular Cloning, a Laboratory Manual, Cold Spring Harbor Laboratory, New York, US, (2001), pp. 6.51, 6.52, 11.27.

Shevchenko, A. et al., "Mass spectrometric sequencing of proteins from silver-stained polyacrylamide gels", Anal. Chem., Vo. 68, No. 5 (1996), pp. 850-858.

Shimogaki, H. et al., "Purification and Properties of a Novel Surface-Active Agent- and Alkaline-resistant Protease from *Bacillus* sp. Y.", Agric. Biol. Chem., vol. 55, No, 9. (1991), pp. 2251-2258.

Siezen, R. J. et al., "Subtilases: The superfamily of subtilisin-like serine proteases", Protein Science, vol. 6, (1997), pp. 501-523 (total pp. 30).

Steyaert, J. M. et al., "Co-expression of two genes, a chitinase (chit42) and proteinase (prbl) implicated in mycoparasitism by Trichoderma hamatum", Mycologia, vol. 96, No. 6, (2004), pp. 1245-1252.

Suarez, M. B. et al., "Characterization of genes encoding novel peptidases in the biocontrol fungus *Trichoderma harzianum* CECT 2413 using the TrichoEST functional genomics approach", Curr. Genet., vol. 51, No. 5, (2007), pp. 331-342.

UNIPROT database (online), Database Accession No. C7ZKJ9, Oct. 13, 2009, from Coleman, J.J. et al, "The genome of Nectria haematococca: contribution of supernumerary chromosomes to gene expansion", PLoS Genet. 5: E1000618-E1000618, (2009), (1 page).

UNIPROT database (online), Database Accession No. C9SL49, Nov. 24, 2009, from Ma, L.-J.J., et al, "Annotation of Verticillium alboatrum VaMs. 102.", Submitted (May 2008) to the EMBL/GenBank/DDBJ databases, (1 page).

UNIPROT database (online), Database Accession No. E3Q3S5, Jan. 11, 2011, from Vaillancourt, L. et al., "The genome sequence of *Glomerella graminicola* strain M1.001.", Submitted (Jun. 2009) to the EMBL/GenBank/DDBJ databases, (1 page).

UNIPROT database (online), Database Accession No. C7YXB3, Oct. 13, 2009, from Coleman, J. J. et al., "The genome of *Nectria haematococca*: contribution of supernumerary chromosomes to gene expansion", PLoS Genet. 5: E1000618-E1000618, (2009), (1 page).

UNIPROT database (online), Database Accession No. A5JS74, Jun. 26, 2007, from Gao, L. et al., "Gene cloning of serine protease from Hirsutella minnesotania", Submitted (Apr. 2007) to the EMBL/GenBank/DDBJ databases, (1 page).

UNIPROT database (online), Database Accession No. Q69IF7, Sep. 13, 2004, from Hane, J.K. et al., "Dothideomycete-plant interactions illuminated by genome sequencing and EST analysis of the wheat pathogen *Stagonospora nodorum*.", Plant Cell, vol. 19, (2007), pp. 3347-3368, (1 page).

UNIPROTKB database (online), Database Accession No. Q874K4, Feb. 10, 2009, from Pozo, J. J. et al., "Functional analysis of tvspl, a serine protease-encoding gene in the biocontrol agent Trichoderma virens", Fungal Genet. Biol., vol. 41, (2004), pp. 336-348 (1 page).

UNIPROTKB database (online), Database Accession No. Q86ZV3-TRIHM, Feb. 10, 2009, from Steyaert, J. M. et al, Co-expression of two genes, a chitinase (chit42) and proteinase, Mycologia, vol. 96, No. 6, (2004), pp. 1245-1252 (1 page).

UNIPROTKB database (online), Database Accession No. Q03420, Jun. 16, 2009, from Geremia, R. A. et al., "Molecular characterization of the preoteinase-encoding gene, prbl, related to mycoparasitism by Trichoderma harzianum", Mol. Microbiol., vol. 8, (1993), pp. 603-613 (2 pages).

UNIPROTKB database (online), Database Accession No. A4V8W7_TRIHA, Feb. 10, 2009, from Suarez, M. B. et al., "Characterization of genes encoding novel peptidases in the biocontrol fungus *Trichoderma harzianum* CECT 2413 using the TrichoEST functional genomics approach", Curr. Genet., vol. 51, (2007), pp. 331-342 (1 page).

Whisstock, J. C. et al., "Prediction of protein function from protein sequence and structure", Quarterly Reviews of Biophysics, vol. 36, No. 3 (2003), pp. 307-304.

International Search Report from corresponding PCT Application No. PCT/EP2011/068837 dated Dec. 15, 2011, (6 pages).

Alkaline protease Aspergillus fumigatus CAA5806.1, created Sep. 3, 1998 (2 pages).

Branden and Tooze, Introduction to Protein Structure, 2nd edition, Garland Science Publisher, pp. 3-12 (1999).

Hill et al., "Fucntional Analysis of conserved Histidines in ADP-Glucose Pyrophosphorylase from *Escherichia coli*," Biochem. Biophys. Res. Comm., 244:573-577 (1998).

Katz et al., "Extreme DNA sequence variation in isolates of *Aspergillus fumigatus*," FEMS Immunology & Medical Microbiology, 20(4):283-288 (1998).

Lazar et al., "Transforming Growth Factor alpha: Mutation of Aspartic Acid 47 and Leucine 48 Results in Different Biological Activity," Mol. Cell. Biol., 8:1247-1252.

McDonagh et al., "Production of caseinophosphopeptides (CPPs) from sodium caseinate using a range of commercial protease preparations," International Dairy Journal 8(1): 39-45 (Mar. 1998).

Guo, H.H. et al., "Protein tolerance to random amino acid change", PNAS, vol. 101, No. 25, (2004), pp. 9205-9210.

* cited by examiner

```
  1   tcatgagcag gcaatcccac tcagttcaat tttgttgatc tacattaatc atgggcgtct
  1              DET27 (s)                                     m  g  v 61   tcagcaaact cttgtatctg tcttttgcag tcacggcctc tgtcaatgcc ggtgaaatcc
  4    f  s  k   l  l  y  l  s  f  a   v  t  a   s  v  n  a   g  e  i 121   tttcagtcgc caacaaggac agtgttatcc ctgacacgta tatcgtggtg ttgaaggaag
 24    l  s  v   a  n  k  d  s  v  i   p  d  t  y  i  v  v   l  k  e 181   gagtttcaac ccaggagttc aatgctcata aaaactgggt gaacgagatt catcgcacca
 44    g  v  s   t  q  e  f  n  a  h   k  n  w   v  n  e  i   h  r  t 241   acctcacgag gcgtgacctg ggtttcactg gcgagttaaa gcatagctat gattttggtg
 64    n  l  t   r  r  d  l  g  f  t   g  e  l   k  h  s  y   d  f  g 301   gacatggact gaagggctac agcggcaagt ttgatgccac tgccattcag gaaattgcca
 84    g  h  g   l  k  g  y  s  g  k   f  d  a   t  a  i  q   e  i  a 361   atgatcctaa tgtatgcttg ttaagaattc ttcccagcga gatatcttca tgcaagccat
104    n  d  p   n                              Intron 1

421   gcaattgctg acaggtgaat taggtggcct acgtcgaacc ggaccaggag gtgaagcttg
108                                     v  a  y   v  e  p   d  q  e  v  k  l 481   atGCATTGGT GACGCAGAGT AATGCACCAT CCTGGGGCCT TGGCCGTATT TCCAACCGAC
120    d  A  L   V  T  Q  S  N  A  P   S  W  G   L  G  R  I   S  N  R 541   AGGCTGGTAT TCGTGATTAC CACTACGATG ACTCCGCCGG TGAAGGCGTC ATCGTCTATG
140    Q  A  G   I  R  D  Y  H  Y  D   D  S  A   G  E  G  V   I  V  Y 601   ATGTTGACAC CGGTATTGAC ATCAGCCATC CGGATTTCGA GGGCCGTGCT ATATGGGGTT
160    D  V  D   T  G  I  D  I  S  H   P  D  F   E  G  R  A   I  W  G 661   CCAACCATGT CGACCGCGTT AACCAGGATC AGAATGGCCA TGGGACACAC GTTGCTGGTA
180    S  N  H   V  D  R  V  N  Q  D   Q  N  G   H  G  T  H   V  A  G 721   CTATTGGTGG AAGGGCGTAC GGAGTCGCCA AGAAGGCCAC AATAGTGGCT GTCAAGGTTC
200    T  I  G   G  R  A  Y  G  V  A   K  K  A   T  I  V  A   V  K  V 781   TCGACGCCCA GGGGTCAGGT ACTATCAGCG GTATTATTGC TGGTCTTGAC TGGAGTGTCA
220    L  D  A   Q  G  S  G  T  I  S   G  I  I   A  G  L  D   W  S  V 841   ATCATGCTCG ACAGAATGGA GTCACTAGAA GAGCGGCTTT GAACATGAGC CTTGGCGGTG
240    N  H  A   R  Q  N  G  V  T  R   R  A  A   L  N  M  S   L  G  G 901   GGCGCAGTAT CTCTTTCAAT CAGGCTGCTG CAAGTGCTGT CCAAGCCGGA TTGTTCGTCG
260    G  R  S   I  S  F  N  Q  A  A   A  S  A   V  Q  A  G   L  F  V
```

Fig. 1A

```
 961  CGGTTGCTGC CGGAAATGAA GGGgtaagtg acttctttct ggccoctoct atccgtacct
 280   A  V  A   A  G  N  E   G                      Intron 2

1021  gcagaagcta accagattgc tcttattttt tttcttttt caaaatatag CAAAATGCAG
 288                                                         Q  N  A 1081  GTAACACTTC CCCAGCCTCA GAGCCTTCTG TTTGCACAGT AGGGGCAACC TCATCGAATG
 291   G  N  T   S  P  A  S   E  P  S   V  C  T   V  G  A   T  S  S  N 1141  ATGCCGCCAC ATCCTGGTCC AACTATGGCT CAGTTGgtac gtagggctcg gttttattta
 311   D  A  A   T  S  W  S   N  Y  G   S  V 1201  ttacttcttc cccacatgcg atcagaccgg ccgctgacta tatttagTTG ACGTTTACGC
 323                       Intron 3                          V  D  V  Y 1261  TCCCGGAGAC GCAATTGTCT CTACCTGGCC CGGTGGCGGT TCCAGGTCTC TCTCAGGCAC
 327   A  P  G  D   A  I  V  S   T  W   P  G  G   S  R  S   L  S  G 1321  ATCGATGGCT TCTCCACACG TCGCCGGCCT GGGTGCATAC CTCATCGCTC TGGAGGGCAT
 347   T  S  M  A   S  P  H   V  A  G   L  G  A  Y   L  I  A   L  E  G 1381  TAGCGGAGGC AGTGTATGTG ACCGTATCAA AGAGCTGGCT CAACCTGTCG TCCAGCCTGG
 367   I  S  G  G   S  V  C   D  R  I   K  E  L   A  Q  P   V  V  Q  P 1441  TCCAGGCACC ACCAACCGTC TTATCTACAA CGGCAGTGGC CGCtaaattg atagtagcta
 387   G  P  G  T   T  N  R   L  I  Y   N  G  S  G   R  *

1501  cagaaggcat agggcttgcg gcgactcggg caatgcagga tatttt
                                DET28 (as)
```

Fig. 1B

SEQUENCE LISTING

<160> NUMBER OF SEQ ID NOS: 22

<210> SEQ ID NO 1
<211> LENGTH: 17
<212> TYPE: DNA
<213> ORGANISM: Artificial Sequence -continued

```
<220> FEATURE:
<223> OTHER INFORMATION: Sequence of DET1 sense primer used in PCR for
      Malbranchea protease probe synthesis.
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 1
ggncayggna cncaygt                                                   17

<210> SEQ ID NO 2
<211> LENGTH: 20
<212> TYPE: DNA
<213> ORGANISM: Artificial Sequence
<220> FEATURE:
<223> OTHER INFORMATION: Sequence of DET2 sense primer used in PCR for
      Malbranchea protease probe synthesis.
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 2
aaytgggcng tnaaygayat                                                20

<210> SEQ ID NO 3
<211> LENGTH: 20
<212> TYPE: DNA
<213> ORGANISM: Artificial Sequence
<220> FEATURE:
<223> OTHER INFORMATION: Sequence of DET3 antisense primer used in PCR
      for Malbranchea protease probe synthesis.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 3
nccrtarttn gtraanswng                                                20

<210> SEQ ID NO 4
<211> LENGTH: 20
<212> TYPE: DNA
<213> ORGANISM: Artificial Sequence
<220> FEATURE:
<223> OTHER INFORMATION: Sequence of DET4 antisense primer used in PCR
      for Malbranchea protease probe synthesis.
```

```
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 4
ngccatnswn gtnccnswda                                            20

<210> SEQ ID NO 5
<211> LENGTH: 26
<212> TYPE: DNA
<213> ORGANISM: Artificial Sequence
<220> FEATURE:
<223> OTHER INFORMATION: Sequence of DET5 sense primer used in PCR for
      Malbranchea protease probe synthesis.
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 5
cargcnggna thmgngayta ycayta                                     26

<210> SEQ ID NO 6
<211> LENGTH: 6
<212> TYPE: PRT
<213> ORGANISM: Artificial Sequence
<220> FEATURE:
<223> OTHER INFORMATION: Sequence of a consensus peptide sequence used
      for design of DET1 sense PCR primer.

<400> SEQUENCE: 6

Gly His Gly Thr His Val
1               5

<210> SEQ ID NO 7
<211> LENGTH: 7
<212> TYPE: PRT
<213> ORGANISM: Artificial Sequence
<220> FEATURE:
<223> OTHER INFORMATION: Sequence of a consensus peptide sequence used
      for design of DET2 sense PCR primer.

<400> SEQUENCE: 7

Asn Trp Ala Val Asn Asp Ile
1               5
```

```
<210> SEQ ID NO 8
<211> LENGTH: 7
<212> TYPE: PRT
<213> ORGANISM: Artificial Sequence
<220> FEATURE:
<223> OTHER INFORMATION: Sequence of a consensus peptide sequence used
      for design of DET3 antisense PCR primer.

<400> SEQUENCE: 8

Ala Ser Phe Thr Asn Tyr Gly
1               5

<210> SEQ ID NO 9
<211> LENGTH: 7
<212> TYPE: PRT
<213> ORGANISM: Artificial Sequence
<220> FEATURE:
<223> OTHER INFORMATION: Sequence of a consensus peptide sequence used
      for design of DET4 antisense PCR primer.

<400> SEQUENCE: 9

Ile Ser Gly Thr Ser Met Ala
1               5

<210> SEQ ID NO 10
<211> LENGTH: 9
<212> TYPE: PRT
<213> ORGANISM: Artificial Sequence
<220> FEATURE:
<223> OTHER INFORMATION: Sequence of the peptide sequence used for
      design of DET5 sense PCR primer.

<400> SEQUENCE: 10

Gln Ala Gly Ile Arg Asp Tyr His Tyr
1               5

<210> SEQ ID NO 11
<211> LENGTH: 791
<212> TYPE: DNA
<213> ORGANISM: Artificial Sequence
<220> FEATURE:
<223> OTHER INFORMATION: Sequence of the PCR fragment obtained using
      DET5 and DET4 in PCR reaction and Malbranchea ALKO4122 genomic DNA
      as a template. This fragment contains a partial Malbranchea
      protease gene and is an insert in the plasmid pALK3092.

<400> SEQUENCE: 11
caggcgggaa ttagggatta tcactacgat gactccgccg gtgaaggcgt catcgtctat     60
gatgttgaca ccggtattga catcagccat ccggatttcg agggccgtgc tatatggggt    120
tccaaccatg tcgaccgcgt taaccaggat cagaatggcc atgggacaca cgttgctggt    180
actattggtg aagggcgta cggagtcgcc aagaaggcca caatagtggc tgtcaaggtt    240
ctcgacgccc aggggtcagg tactatcagc ggtattattg ctggtcttga ctggagtgtc    300
aatcatgctc gacagaatgg agccactaga agagcggctt tgaacatgag ccttggcggt    360
gggcgcagta tctctttcaa tcaggctgct gcaagtgctg tccaagccgg attgttcgtc    420
gcggttgctg ccggaaatga agggtaagt gacttctttc tggcccctcc tatccgtacc    480
tgcagaagct aaccagattg ctcttatttt ttttcttttt tcaaaatata gcaaaatgca    540
ggtaacactt ccccagcctc agagccttct gtttgcacag taggggcaac ctcatcgaat    600
gatgccgcca catcctggtc caactatggc tcagttggta cgtagggctc ggttttattt    660
attacttctt ccccacatgc gatcagaccg gccgctgact atatttagtt gacgtttacg    720
```

```
ctcccggaga cgcaattgtc tctacctggc ccggtggcgg ttccaggtct ctcaccggca    780
cctcgatggc t                                                          791
```

<210> SEQ ID NO 12
<211> LENGTH: 791
<212> TYPE: DNA
<213> ORGANISM: Artificial Sequence
<220> FEATURE:
<223> OTHER INFORMATION: Sequence of the PCR fragment obtained using
      DET5 and DET4 in PCR reaction and Malbranchea ALKO4178 genomic DNA
      as a template. This fragment contains a partial Malbranchea
      protease gene and is an insert in the plasmid pALK3093.

<400> SEQUENCE: 12

```
caagccggaa ttagtgatta ccactacgat gactccgccg gtgaaggcgt catcgtctat     60
gatgttgaca ccggtattga catcagccat ccggatttcg aggccgtgc tatatggggt    120 tccaaccatg tcgaccgcgt taaccaggat cagaatggcc atgggacaca cgttgctggt    180
actattggtg aagggcgta cggagtcgcc aagaaggcca caatagtggc tgtcaaggtt    240
ctcgacgccc aggggtcagg tactatcagc ggtattattg ctggtcttga ctggagtgtc    300
aatcatgctc gacagaatgg agtcactaga gagcggcctt tgaacatgag ccttggcggt    360
gggcgcagta tctcttttcaa tcaggctgct gcaagtgctg tccaagccgg attgttcgtc    420
gcggttgctg ccggaaatga aggggtaagt gacttcttc tggcccctcc tatccgtacc    480
tgcagaagct aaccagattg ctcttatttt ttttcttttt tcaaaatata gcaaaatgca    540
ggtaacactt ccccagcctc agagccttct gtttgcacag taggcaac ctcatcgaat     600 gatgccgcca tcctggtc caactatggc tcagttggta cgtagggctc ggttttattt    660
attacttctt ccccacatgc gatcagaccg gccgctgact atatttagtt gacgtttacg    720
ctcccggaga cgcaattgtc tctacctggc ccggtggcgg ttccaggtct ctctcaggaa    780
caaccatggc t                                                          791
```

<210> SEQ ID NO 13
<211> LENGTH: 1436
<212> TYPE: DNA
<213> ORGANISM: Malbranchea cinnamomea
<220> FEATURE:
<221> NAME/KEY: misc_feature
<223> OTHER INFORMATION: genomic sequence

<400> SEQUENCE: 13

```
atgggcgtct tcagcaaact cttgtatctg tcttttgcag tcacggcctc tgtcaatgcc     60
ggtgaaatcc tttcagtcgc caacaaggac agtgttatcc ctgacacgta tatcgtggtg    120
ttgaaggaag gagtttcaac ccaggagttc aatgctcata aaaactgggt gaacgagatt    180
catcgcacca acctcacgag gcgtgacctg ggtttcactg gcgagttaaa gcatagctat    240
gattttggtg acatggact gaagggctac agcggcaagt tgatgccac tgccattcag    300 gaaattgcca atgatcctaa tgtatgcttg ttaagaattc ttcccagcga gatatcttca    360
tgcaagccat gcaattgctg acaggtgaat taggtggcct acgtcgaacc ggaccaggag    420
gtgaagcttg atgcattggt gacgcagagt aatgcaccat cctggggcct tggccgtatt    480
tccaaccgac aggctggtat tcgtgattac cactacgatg actccgccgg tgaaggcgtc    540
atcgtctatg atgttgacac cggtattgac atcagccatc cggatttcga ggccgtgct    600 atatggggtt ccaaccatgt cgaccgcgtt aaccaggatc agaatggcca tgggacacac    660
gttgctggta ctattggtgg aagggcgtac ggagtcgcca agaaggccac aatagtggct    720
```

-continued

```
gtcaaggttc tcgacgccca ggggtcaggt actatcagcg gtattattgc tggtcttgac      780
tggagtgtca atcatgctcg acagaatgga gtcactagaa gagcggcttt gaacatgagc      840
cttggcggtg ggcgcagtat ctctttcaat caggctgctg caagtgctgt ccaagccgga      900
ttgttcgtcg cggttgctgc cggaaatgaa ggggtaagtg acttcttcct ggcccctcct      960
atccgtacct gcagaagcta accagattgc tcttattttt tttctttttt caaaatatag     1020
caaaatgcag gtaacacttc cccagcctca gagccttctg tttgcacagt aggggcaacc     1080
tcatcgaatg atgccgccac atcctggtcc aactatggct cagttggtac gtagggctcg     1140
gttttattta ttacttcttc cccacatgcg atcagaccgg ccgctgacta tatttagttg     1200
acgtttacgc tcccggagac gcaattgtct ctacctggcc cggtggcggt tccaggtctc     1260
tctcaggcac atcgatggct tctccacacg tcgccggcct gggtgcatac ctcatcgctc     1320
tggagggcat tagcggaggc agtgtatgtg accgtatcaa agagctggct caacctgtcg     1380
tccagcctgg tccaggcacc accaaccgtc ttatctacaa cggcagtggc cgctaa        1436
```

<210> SEQ ID NO 14
<211> LENGTH: 401
<212> TYPE: PRT
<213> ORGANISM: Malbranchea cinnamomea
<220> FEATURE:
<221> NAME/KEY: misc_feature
<223> OTHER INFORMATION: genomic sequence

<400> SEQUENCE: 14

```
Met Gly Val Phe Ser Lys Leu Leu Tyr Leu Ser Phe Ala Val Thr Ala
1               5                   10                  15

Ser Val Asn Ala Gly Glu Ile Leu Ser Val Ala Asn Lys Asp Ser Val
            20                  25                  30

Ile Pro Asp Thr Tyr Ile Val Leu Lys Glu Gly Val Ser Thr Gln
        35                  40                  45

Glu Phe Asn Ala His Lys Asn Trp Val Asn Glu Ile His Arg Thr Asn
    50                  55                  60

Leu Thr Arg Arg Asp Leu Gly Phe Thr Gly Glu Leu Lys His Ser Tyr
65                  70                  75                  80

Asp Phe Gly Gly His Gly Leu Lys Gly Tyr Ser Gly Lys Phe Asp Ala
                85                  90                  95

Thr Ala Ile Gln Glu Ile Ala Asn Asp Pro Asn Val Ala Tyr Val Glu
            100                 105                 110

Pro Asp Gln Glu Val Lys Leu Asp Ala Leu Val Thr Gln Ser Asn Ala
        115                 120                 125

Pro Ser Trp Gly Leu Gly Arg Ile Ser Asn Arg Gln Ala Gly Ile Arg
    130                 135                 140

Asp Tyr His Tyr Asp Asp Ser Ala Gly Glu Gly Val Ile Val Tyr Asp
145                 150                 155                 160

Val Asp Thr Gly Ile Asp Ile Ser His Pro Asp Phe Glu Gly Arg Ala
                165                 170                 175

Ile Trp Gly Ser Asn His Val Asp Arg Val Asn Gln Asp Gln Asn Gly
            180                 185                 190

His Gly Thr His Val Ala Gly Thr Ile Gly Gly Arg Ala Tyr Gly Val
        195                 200                 205

Ala Lys Lys Ala Thr Ile Val Ala Val Lys Val Leu Asp Ala Gln Gly
    210                 215                 220

Ser Gly Thr Ile Ser Gly Ile Ile Ala Gly Leu Asp Trp Ser Val Asn
225                 230                 235                 240
```

```
His Ala Arg Gln Asn Gly Val Thr Arg Arg Ala Ala Leu Asn Met Ser
                245                 250                 255

Leu Gly Gly Gly Arg Ser Ile Ser Phe Asn Gln Ala Ala Ala Ser Ala
            260                 265                 270

Val Gln Ala Gly Leu Phe Val Ala Val Ala Ala Gly Asn Glu Gly Gln
        275                 280                 285

Asn Ala Gly Asn Thr Ser Pro Ala Ser Glu Pro Ser Val Cys Thr Val
    290                 295                 300

Gly Ala Thr Ser Ser Asn Asp Ala Ala Thr Ser Trp Ser Asn Tyr Gly
305                 310                 315                 320

Ser Val Val Asp Val Tyr Ala Pro Gly Asp Ala Ile Val Ser Thr Trp
                325                 330                 335

Pro Gly Gly Gly Ser Arg Ser Leu Ser Gly Thr Ser Met Ala Ser Pro
            340                 345                 350

His Val Ala Gly Leu Gly Ala Tyr Leu Ile Ala Leu Glu Gly Ile Ser
        355                 360                 365

Gly Gly Ser Val Cys Asp Arg Ile Lys Glu Leu Ala Gln Pro Val Val
    370                 375                 380

Gln Pro Gly Pro Gly Thr Thr Asn Arg Leu Ile Tyr Asn Gly Ser Gly
385                 390                 395                 400

Arg
```

<210> SEQ ID NO 15
<211> LENGTH: 1376
<212> TYPE: DNA
<213> ORGANISM: Malbranchea cinnamomea
<220> FEATURE:
<221> NAME/KEY: misc_feature
<223> OTHER INFORMATION: genomic sequence

<400> SEQUENCE: 15

```
ggtgaaatcc tttcagtcgc caacaaggac agtgttatcc ctgacacgta tatcgtggtg      60
ttgaaggaag gagtttcaac ccaggagttc aatgctcata aaaactgggt gaacgagatt     120
catcgcacca acctcacgag gcgtgacctg ggtttcactg gcgagttaaa gcatagctat     180
gattttggtg acatggact gaagggctac agcggcaagt tgatgccac tgccattcag      240
gaaattgcca atgatcctaa tgtatgcttg ttaagaattc ttcccagcga gatatcttca     300
tgcaagccat gcaattgctg acaggtgaat taggtggcct acgtcgaacc ggaccaggag     360
gtgaagcttg atgcattggt gacgcagagt aatgcaccat cctggggcct tggccgtatt     420
tccaaccgac aggctggtat tcgtgattac cactacgatg actccgccgg tgaaggcgtc     480
atcgtctatg atgttgacac cggtattgac atcagccatc cggatttcga gggccgtgct     540
atatggggtt ccaaccatgt cgaccgcgtt aaccaggatc agaatggcca tgggacacac     600
gttgctggta ctattggtgg aagggcgtac ggagtcgcca agaaggccac aatagtggct     660
gtcaaggttc tcgacgccca ggggtcaggt actatcagcg gtattattgc tggtcttgac     720
tggagtgtca atcatgctcg acagaatgga gtcactagaa gagcggcttt gaacatgagc     780
cttggcggtg ggcgcagtat ctctttcaat caggctgctg caagtgctgt ccaagccgga     840
ttgttcgtcg cggttgctgc cggaaatgaa ggggtaagtg acttctttct ggcccctcct     900
atccgtacct gcagaagcta accagattgc tcttattttt ttcttttttt caaaatatag     960
caaaatgcag gtaacactttc cccagcctca gagccttctg tttgcacagt aggggcaacc    1020
tcatcgaatg atgccgccac atcctggtcc aactatggct cagttggtac gtagggctcg    1080
```

```
gttttattta ttacttcttc cccacatgcg atcagaccgg ccgctgacta tatttagttg    1140
acgtttacgc tcccggagac gcaattgtct ctacctggcc cggtggcggt tccaggtctc    1200
tctcaggcac atcgatggct ctccacacg tcgccggcct gggtgcatac ctcatcgctc     1260
tggagggcat tagcggaggc agtgtatgtg accgtatcaa agagctggct caacctgtcg    1320
tccagcctgg tccaggcacc accaaccgtc ttatctacaa cggcagtggc cgctaa         1376
```

<210> SEQ ID NO 16
<211> LENGTH: 381
<212> TYPE: PRT
<213> ORGANISM: Malbranchea cinnamomea
<220> FEATURE:
<221> NAME/KEY: misc_feature
<223> OTHER INFORMATION: genomic sequence

<400> SEQUENCE: 16

```
Gly Glu Ile Leu Ser Val Ala Asn Lys Asp Ser Val Ile Pro Asp Thr
 1               5                  10                  15

Tyr Ile Val Val Leu Lys Glu Gly Val Ser Thr Gln Glu Phe Asn Ala
                20                  25                  30

His Lys Asn Trp Val Asn Glu Ile His Arg Thr Asn Leu Thr Arg Arg
            35                  40                  45

Asp Leu Gly Phe Thr Gly Glu Leu Lys His Ser Tyr Asp Phe Gly Gly
        50                  55                  60

His Gly Leu Lys Gly Tyr Ser Gly Lys Phe Asp Ala Thr Ala Ile Gln
65                  70                  75                  80

Glu Ile Ala Asn Asp Pro Asn Val Ala Tyr Val Glu Pro Asp Gln Glu
                85                  90                  95

Val Lys Leu Asp Ala Leu Val Thr Gln Ser Asn Ala Pro Ser Trp Gly
            100                 105                 110

Leu Gly Arg Ile Ser Asn Arg Gln Ala Gly Ile Arg Asp Tyr His Tyr
        115                 120                 125

Asp Asp Ser Ala Gly Glu Gly Val Ile Val Tyr Asp Val Asp Thr Gly
    130                 135                 140

Ile Asp Ile Ser His Pro Asp Phe Glu Gly Arg Ala Ile Trp Gly Ser
145                 150                 155                 160

Asn His Val Asp Arg Val Asn Gln Asp Gln Asn Gly His Gly Thr His
                165                 170                 175

Val Ala Gly Thr Ile Gly Gly Arg Ala Tyr Gly Val Ala Lys Lys Ala
            180                 185                 190

Thr Ile Val Ala Val Lys Val Leu Asp Ala Gln Gly Ser Gly Thr Ile
        195                 200                 205

Ser Gly Ile Ile Ala Gly Leu Asp Trp Ser Val Asn His Ala Arg Gln
    210                 215                 220

Asn Gly Val Thr Arg Arg Ala Ala Leu Asn Met Ser Leu Gly Gly Gly
225                 230                 235                 240

Arg Ser Ile Ser Phe Asn Gln Ala Ala Ser Ala Val Gln Ala Gly
                245                 250                 255

Leu Phe Val Ala Val Ala Ala Gly Asn Glu Gly Gln Asn Ala Gly Asn
            260                 265                 270

Thr Ser Pro Ala Ser Glu Pro Ser Val Cys Thr Val Gly Ala Thr Ser
        275                 280                 285

Ser Asn Asp Ala Ala Thr Ser Trp Ser Asn Tyr Gly Ser Val Val Asp
    290                 295                 300
```

```
Val Tyr Ala Pro Gly Asp Ala Ile Val Ser Thr Trp Pro Gly Gly Gly
305                 310                 315                 320

Ser Arg Ser Leu Ser Gly Thr Ser Met Ala Ser Pro His Val Ala Gly
            325                 330                 335

Leu Gly Ala Tyr Leu Ile Ala Leu Glu Gly Ile Ser Gly Ser Val
        340                 345                 350

Cys Asp Arg Ile Lys Glu Leu Ala Gln Pro Val Val Gln Pro Gly Pro
            355                 360                 365

Gly Thr Thr Asn Arg Leu Ile Tyr Asn Gly Ser Gly Arg
        370                 375                 380

<210> SEQ ID NO 17
<211> LENGTH: 1004
<212> TYPE: DNA
<213> ORGANISM: Malbranchea cinnamomea
<220> FEATURE:
<221> NAME/KEY: misc_feature
<223> OTHER INFORMATION: genomic sequence

<400> SEQUENCE: 17
gcattggtga cgcagagtaa tgcaccatcc tggggccttg ccgtatttc caaccgacag      60
gctggtattc gtgattacca ctacgatgac tccgccggtg aaggcgtcat cgtctatgat    120
gttgacaccg gtattgacat cagccatccg gatttcgagg ccgtgctat atggggttcc    180
aaccatgtcg accgcgttaa ccaggatcag aatggccatg gacacacgt tgctggtact    240
attggtggaa gggcgtacgg agtcgccaag aaggccacaa tagtggctgt caaggttctc    300
gacgcccagg ggtcaggtac tatcagcggt attattgctg tcttgactg gagtgtcaat    360
catgctcgac agaatggagt cactagaaga gcggctttga acatgagcct tggcggtggg    420
cgcagtatct ctttcaatca ggctgctgca agtgctgtcc aagccggatt gttcgtcgcg    480
gttgctgccg gaaatgaagg ggtaagtgac ttctttctgg ccctcctat ccgtacctgc    540
agaagctaac cagattgctc ttattttttt tctttttca aaatatagca aaatgcaggt    600
aacacttccc cagcctcaga gccttctgtt tgcacagtag gggcaacctc atcgaatgat    660
gccgccacat cctggtccaa ctatggctca gttggtacgt agggctcggt tttatttatt    720
acttcttccc cacatgcgat cagaccggcc gctgactata tttagttgac gtttacgctc    780
ccggagacgc aattgtctct acctggcccg gtggcggttc caggtctctc tcaggcacat    840
cgatggcttc tccacacgtc gccggcctgg gtgcatacct catcgctctg gagggcatta    900
gcggaggcag tgtatgtgac cgtatcaaag agctggctca acctgtcgtc cagcctggtc    960
caggcaccac caaccgtctt atctacaacg gcagtggccg ctaa                   1004

<210> SEQ ID NO 18
<211> LENGTH: 281
<212> TYPE: PRT
<213> ORGANISM: Malbranchea cinnamomea
<220> FEATURE:
<221> NAME/KEY: misc_feature
<223> OTHER INFORMATION: genomic sequence

<400> SEQUENCE: 18

Ala Leu Val Thr Gln Ser Asn Ala Pro Ser Trp Gly Leu Gly Arg Ile
1               5                   10                  15

Ser Asn Arg Gln Ala Gly Ile Arg Asp Tyr His Tyr Asp Asp Ser Ala
            20                  25                  30

Gly Glu Gly Val Ile Val Tyr Asp Val Asp Thr Gly Ile Asp Ile Ser
        35                  40                  45
```

```
His Pro Asp Phe Glu Gly Arg Ala Ile Trp Gly Ser Asn His Val Asp
    50                  55                  60
Arg Val Asn Gln Asp Gln Asn Gly His Gly Thr His Val Ala Gly Thr
65                  70                  75                  80
Ile Gly Gly Arg Ala Tyr Gly Val Ala Lys Lys Ala Thr Ile Val Ala
                85                  90                  95
Val Lys Val Leu Asp Ala Gln Gly Ser Gly Thr Ile Ser Gly Ile Ile
            100                 105                 110
Ala Gly Leu Asp Trp Ser Val Asn His Ala Arg Gln Asn Gly Val Thr
        115                 120                 125
Arg Arg Ala Ala Leu Asn Met Ser Leu Gly Gly Gly Arg Ser Ile Ser
    130                 135                 140
Phe Asn Gln Ala Ala Ala Ser Ala Val Gln Ala Gly Leu Phe Val Ala
145                 150                 155                 160
Val Ala Ala Gly Asn Glu Gly Gln Asn Ala Gly Asn Thr Ser Pro Ala
                165                 170                 175
Ser Glu Pro Ser Val Cys Thr Val Gly Ala Thr Ser Ser Asn Asp Ala
            180                 185                 190
Ala Thr Ser Trp Ser Asn Tyr Gly Ser Val Val Asp Val Tyr Ala Pro
        195                 200                 205
Gly Asp Ala Ile Val Ser Thr Trp Pro Gly Gly Ser Arg Ser Leu
    210                 215                 220
Ser Gly Thr Ser Met Ala Ser Pro His Val Ala Gly Leu Gly Ala Tyr
225                 230                 235                 240
Leu Ile Ala Leu Glu Gly Ile Ser Gly Ser Val Cys Asp Arg Ile
                245                 250                 255
Lys Glu Leu Ala Gln Pro Val Val Gln Pro Gly Pro Gly Thr Thr Asn
            260                 265                 270
Arg Leu Ile Tyr Asn Gly Ser Gly Arg
        275                 280

<210> SEQ ID NO 19
<211> LENGTH: 21
<212> TYPE: DNA
<213> ORGANISM: Artificial Sequence
<220> FEATURE:
<223> OTHER INFORMATION: Sequence of the PCR sense primer DET27 used for
      cloning of the Malbranchea ALKO4178 protease gene.

<400> SEQUENCE: 19
gcaggcaatc ccactcagtt c                                           21

<210> SEQ ID NO 20
<211> LENGTH: 19
<212> TYPE: DNA
<213> ORGANISM: Artificial Sequence
<220> FEATURE:
<223> OTHER INFORMATION: Sequence of the PCR antisense primer DET28 used
      for cloning of the Malbranchea ALKO4178 protease gene.

<400> SEQUENCE: 20
atcctgcatt gcccgagtc                                              19

<210> SEQ ID NO 21
<211> LENGTH: 45
<212> TYPE: DNA
<213> ORGANISM: Artificial Sequence
<220> FEATURE:
<223> OTHER INFORMATION: Sequence of the PCR sense primer DET17.
```

```
<400> SEQUENCE: 21
tccccgcgga ctgcgcatca tgggcgtctt cagcaaactc ttgta        45

<210> SEQ ID NO 22
<211> LENGTH: 35
<212> TYPE: DNA
<213> ORGANISM: Artificial Sequence
<220> FEATURE:
<223> OTHER INFORMATION: Sequence of the PCR antisense primer DET18.

<400> SEQUENCE: 22
cgcggatcct tagcggccac tgccgttgta gataa        35
```

PROTEASE ENZYME AND USES THEREOF

CROSS REFERENCE TO RELATED APPLICATIONS

Under 35 U.S.C. §119(e), this application claims the benefit of both U.S. Provisional Application No. 61/470,168, filed Mar. 31, 2011, and Finnish Patent Application No. 20115310, filed Mar. 31, 2011. The contents of each of the foregoing applications are hereby incorporated by reference in their entireties in this application.

FIELD OF THE INVENTION

The present invention relates to a serine protease enzyme, particularly to a fungal serine protease enzyme useful in various applications, particularly in detergents. The invention relates to a nucleic acid molecule encoding said enzyme, a recombinant vector, a host cell for producing said enzyme, an enzyme composition comprising said enzyme as well as a process for preparing such composition. This invention relates also to various uses of said enzyme and compositions comprising said enzyme.

BACKGROUND

Microbial proteases are among the most important hydrolytic enzymes and find applications in various industrial sectors, such as detergents, food, leather, pharmaceuticals, diagnostics, waste management and silver recovery. Microbial extracellular proteases account for a major part of the total worldwide industrial enzyme sales (Cherry and Fidantsef, 2003). Approximately 90% of the commercial proteases are detergent enzymes (Gupta et al., 2002). The commercial detergent preparations currently in use comprise the naturally occurring alkaline serine proteases (EC 3.4.21) of the subtilisin family or subtilisins (EC 3.4.21.62), originating from *Bacillus* species, or are recombinant protease preparations thereof (Maurer, 2004).

Examples of commercial proteases are such as Subtilisin Carlsberg (Alcalase®), Subtilisin 309 (Savinase®), Subtilisin 147 (Esperase®), Kannase®, Everlase®, Ovozyme®, and the cold-wash protease Polarzyme® (Novozymes A/S, DK), Purafect®, Purafect® Ox, Purafect® Prime and Properase® (Genencor Int., Inc., USA), and the BLAP S and X series (Henkel, D E).

Several alkaline serine proteases and genes encoding these enzymes have also been isolated from eukaryotic organisms, including yeast and filamentous fungi. U.S. Pat. No. 3,652, 399 and EP 519229 (Takeda Chemical Industries, Ltd., JP) disclose an alkaline protease from the genus *Fusarium* (asexual state, teleomorph) or *Gibberella*, (sexual state, anamorph) particularly from *Fusarium* sp. S-19-5 (ATCC 20192, IFO 8884), *F. oxysporum* f. sp. lint (IFO 5880) or *G. saubinetti* (ATCC 20193, IF06608), useful in the formulation of detergent and other cleanser compositions. WO1994025583 (NovoNordisk A/S, DK) discloses an active trypsin-like protease enzyme derivable from a *Fusarium* species, in particular a strain of *F. oxysporum* (DSM 2672), and the DNA sequence encoding the same. The amino acid and nucleotide sequences of the serine proteases from *F. equiseti* and *F. acuminatum* have been disclosed in WO 2010125174 and WO 2010125175, respectively (AB Enzymes Oy, FI). Also, alkaline proteases from fungal species such as *Tritirachium* and *Conidiobolus* have been reported (reviewed in Anwar and Saleemuddin 1998)

The major problem in the use of proteases in liquid detergents is their instability. In liquid detergents enzymes are in direct contact with water and chatropic agents like anionic surfactants and complexing agents, which can lead to irreversible denaturation. Proteases degrade proteins including other enzymes in detergent formulations and themselves. The auto-proteolysis is enhanced by surfactants and heat. Thus, the stability of liquid detergents containing protease represents a major challenge for product development (Maurer, 2010).

Various methods have been used for improving the stability of industrial serine proteases. WO 92/03529 (NovoNordisk A/S, DK), US 2009/096916 (Genencor Int. Inc., US) and WO 2007/145963 (Procter & Gamble Co., US) disclose the use of a reversible protease inhibitor of a peptide or protein type. Liquid detergent compositions comprising proteases often include protease inhibitors such as boric acid with or without polyols to inhibit the activity of proteases. One example of such inhibitors is 4-formyl phenyl boronic acid (4-FPBA) disclosed in US 2010/0120649 (Novozymes A/S, DK). The stability of proteases has also been improved by using a combination of halide salts with polyols (WO 02/08398, Genencor Int. Inc., US). EP 0352244A2 (NovoNordisk A/S, DK) suggests improving the stability of *Bacillus* derived enzymes using amphoteric compounds, such as surfactants.

Based on the information derived from the crystal structures and sequence similarity comparisons between homologous proteins, variants with improved stability and/or improved performance may be designed. Variants of the natural serine proteases with improved catalytic efficiency and/or better stability towards temperature, oxidizing agents and different washing conditions, as well as improved storage stability in liquid detergents have been developed through site-directed and/or random mutagenesis.

Thermomycolin EC 3.4.21.65, isolated as an extracellular alkaline endopeptidase, is produced by a thermophilic fungus *Malbranchea pulcella* var. *sulfurea*. Thermomycolin is described as a 325 residue, single-chain protein. It has the active-site sequence -Leu-Ser-(Gly)-Thr-Ser*-Met-, which is typical for a member of the subtilisin family. Thermomycolin possesses one disulfide bridge, which is exceptional. Thermomycolin is not as thermostable as the extracellular serine proteinases of thermophilic bacteria, but it is more stable than most fungal proteinases (Gaucher and Stevenson, 2004). According to Ong and Gaucher (1975) the thermal inactivation of thermomycolin occurs at 73° C. in the presence of 10 mM $Ca^{2+}$. Thermomycolin hydrolyses casein on broad pH range. The optimum pH for hydrolysis of casein is about 8.5.

Abu-Shady et al. (2001) disclose properties of a protease from *Malbranchea sulfurea* that is a local isolate from soil samples collected from butcheries in Egypt and cultured to obtain a protease enzyme. This publication describes the relative activity of *M. sulphurea* protease in the presence of certain detergents at low concentrations (0.7%) at 30-90° C. using preincubation time of 15-60 mM, i.e. at conditions resembling washing conditions. However, it does not give any indication of the stain removal performance or the storage stability of this protease in detergent itself, which are essential properties for the suitability for use of a protease in detergent formulations. The publication also describes the temperature and pH profiles of a partially purified protease. The optimum temperature of the protease is at 50° C. and optimum pH at 9.0.

Despite the fact that numerous patent publications, reviews and articles have been published, disclosing fungal serine proteases from various microorganisms, for example, the low temperature alkaline proteases from actinomycete (*Nocar-*

*diopsis dassonvillei*) and fungal (*Paecilomyces marquandii*) microorganisms, e.g. in EP 0290567 and EP 0290569 (Novo Nordisk A/S, DK), there is still a great need for new proteases, which are suitable for and effective in modifying, degrading and removing proteinaceous materials of different stains, particularly at low or moderate temperature ranges and which are stable in the presence of detergents with highly varying properties. Due to the autocatalytic property of serine proteases, the stability during storage is also very important.

It is also desirable that the serine protease can be produced in high amounts, and can be cost-effectively down-stream processed, by easy separation from fermentation broth and mycelia.

SUMMARY OF THE INVENTION

The object of the present invention is to provide a serine protease of fungal origin which is active at broad pH ranges and functions particularly well at low and moderate temperatures. The serine proteases for detergent application have to be stable also in the presence of detergents and to be compatible with detergents. Particularly, the object of the invention is to provide a serine protease, which is capable of removing proteinaceous material, including stains in washing laundry and dishes, at lower temperatures than a commercial enzyme preparation, whereby for example more sensitive materials can be washed and energy is saved. Further objects of the invention are to provide a nucleic acid molecule encoding said enzyme, a recombinant vector, a host cell for producing said enzyme, a composition comprising said enzyme, a process for preparing such composition, as well as s uses of said enzyme and compositions comprising said enzyme.

The fungal serine protease according to the invention can be produced in high-yielding fungal hosts and its downstream processing, e.g. separation of fermentation broth and mycelia is easy to perform.

The present invention relates to a fungal serine protease enzyme, which has serine protease activity and comprises an amino acid sequence having at least 66% identity to the amino acid sequence as defined in SEQ ID No:18. A preferred serine protease is derived from *Malbranchea cinnamomea* (Lib.) Oorschot de Hoog.

In the present context, "derived from" is intended not only to indicate a serine protease produced or producible by a strain of the organism in question, but also a serine protease encoded by a DNA sequence isolated from such strain and produced in a host organism transformed with said DNA sequence. Finally, the term is intended to indicate a serine protease, which is encoded by a DNA sequence of synthetic and/or cDNA origin and which has the identifying characteristics of serine protease in question.

Preferably the invention relates to a fungal serine protease enzyme, which has serine protease activity and comprises an amino acid sequence having at least 66% identity to the amino acid sequence of the mature *Malbranchea* ALKO4122 protease as defined in SEQ ID No:18 or the an amino acid sequence of the mature *Malbranchea* ALKO4122 protease as defined in SEQ ID No:18.

The fungal serine protease enzyme of the invention is obtainable from *Malbranchea*, preferably from *Malbranchea cinnamomea* (Lib.) Oorschot de Hoog (Synonym of *Malbranchea pulchella* var. *sulfurea* (Miehe) Cooney & R. Emers.). According to the particularly preferred embodiment the serine protease enzyme of the invention is obtainable from the *Malbranchea* ALKO4122 strain deposited under accession number CBS 128533 or from the strain *Malbranchea* ALKO4178 deposited under accession number CBS 128564.

The protease enzyme of *Malbranchea* ALKO4178 is essentially identical with the protease enzyme of *Malbranchea* ALKO4122 strain.

The fungal serine protease enzyme has a molecular mass between 20 and 35 kDa. The temperature optimum of the enzyme is in the range from 30° C. to 80° C. at pH 8.5, preferably at approximately 70° C. The pH optimum of the enzyme is in the range from at least pH 6 to pH 10 at 50° C., preferably at pH 10. The temperature and pH characteristics were determined using 30 min reaction time and casein as a substrate.

The fungal serine protease of the invention is capable in degrading or removing proteinaceous stains in the presence of detergents at a temperature from 0° C. to 90° C., preferably at a temperature from 5° C. to 60° C., particularly preferably at a temperature from 10° C. to 40° C.

The fungal serine protease enzyme of the invention is encoded by an isolated polynucleotide sequence, which hybridizes under stringent conditions to a polynucleotide sequence included in plasmid pALK3092 comprising the nucleotide sequence SEQ ID No:11, deposited in *E. coli* RF8758 under accession number DSM 24426 or to the sequence encoding the mature ALKO4122 protease SEQ ID No:17. Alternatively, the fungal serine protease enzyme of the invention is encoded by an isolated polynucleotide sequence, which hybridizes under stringent conditions to a polynucleotide sequence included in plasmid pALK3093 comprising the nucleotide sequence SEQ ID No:12, deposited in *E. coli* RF8759 under accession number DSM 24427.

Said enzyme is encoded by an isolated polynucleotide sequence, which encodes a polypeptide comprising an amino acid sequence of the mature *Malbranchea* ALKO4122 protease as defined in SEQ ID No:18 or an amino acid sequence having at least 66% identity to the amino acid sequence of the mature *Malbranchea* ALKO4122 protease as defined in SEQ ID No:18. Preferably, said enzyme is encoded by an isolated nucleic acid molecule comprising the nucleotide sequence SEQ ID No:17.

The full-length fungal serine protease enzyme of the invention is encoded by the polynucleotide sequence included in pALK3094 deposited in *Escherichia coli* RF8791 under accession number DSM 24410.

The fungal serine protease enzyme is produced from a recombinant expression vector comprising the nucleic acid molecule encoding a fungal serine protease of the invention, operably linked to regulatory sequences capable of directing the expression of the serine protease enzyme in a suitable host. Suitable hosts include heterologous hosts, preferably microbial hosts of the genus *Trichoderma, Aspergillus, Fusarium, Humicola, Chrysosporium, Neurospora, Rhizopus, Penicillium, Myceliophthora*, and *Mortierella*. Preferably said enzyme is produced in *Trichoderma* or *Aspergillus*, most preferably in *T. reesei*.

The present invention relates also to an isolated nucleic acid molecule comprising a polynucleotide sequence encoding a serine protease enzyme selected from the group consisting of:
  (a) a nucleic acid molecule encoding a polypeptide having serine protease activity and comprising the amino acid sequence as depicted in SEQ ID No:18;
  (b) a nucleic acid molecule encoding a polypeptide having serine protease activity and at least 66% identity to the amino acid sequence of SEQ ID No:18;
  (c) a nucleic acid molecule comprising the coding sequence of the nucleotide sequence as depicted in SEQ ID No: 17;

(d) a nucleic acid molecule comprising the coding sequence of the polynucleotide sequence contained in DSM 24410;

(e) a nucleic acid molecule the coding sequence of which differs from the coding sequence of a nucleic acid molecule of any one of (c) to (d) due to the degeneracy of the genetic code; and (f) a nucleic acid molecule hybridizing under stringent conditions to a nucleic acid molecule contained in DSM 24426, or SEQ ID No:17 encoding a polypeptide having serine protease activity and an amino acid sequence which shows at least 66% identity to the amino acid sequence as depicted in SEQ ID No:18.

The invention further relates to a recombinant expression vector comprising the nucleotide sequence of the invention operably linked to regulatory sequences capable of directing expression of said serine protease gene in a suitable host. Suitable hosts include heterologous hosts, preferably microbial hosts of the genus *Trichoderma, Aspergillus, Fusarium, Humicola, Chrysosporium, Neurospora, Rhizopus, Myceliophthora*, and *Mortierella*. Preferably said enzyme is produced in *Trichoderma* or *Aspergillus*, most preferably in *T. reesei*.

The invention relates also to a host cell comprising the recombinant expression vector as described above. Preferably, the host cell is a microbial host, such as a filamentous fungus. Preferred hosts are of a genus *Trichoderma, Aspergillus, Fusarium, Humicola, Chrysosporium, Neurospora, Rhizopus, Penicillium, Myceliophthora*, and *Mortierella*. More preferably the host is *Trichoderma* or *Aspergillus*, most preferably a filamentous fungus *T. reesei*.

The present invention relates to a process of producing a polypeptide having serine protease activity, said process comprising the steps of culturing the host cell of the invention and recovering the polypeptide. Also within the invention is a polypeptide having serine protease activity encoded by the nucleic acid sequence of the invention and which is obtainable by the process described above.

The invention relates to a process for obtaining an enzyme preparation comprising the steps of culturing a host cell of the invention and either recovering the polypeptide from the cells or separating the cells from the culture medium and obtaining the supernatant. Within the invention is also an enzyme preparation obtainable by the process described above.

The invention relates to an enzyme preparation, which comprises the serine protease enzyme of the invention.

The invention further relates to a composition comprising the serine protease enzyme of the invention.

The enzyme preparation or composition (e.g. detergent formulation) containing the protease enzyme of the invention may further comprise other enzymes selected from the group consisting of proteases (other protease than that of the invention), amylases, cellulases, lipases, xylanases, mannanases, cutinases, pectinases and oxidases with or without a mediator as well as suitable additives selected from the group consisting of stabilizers, buffers, surfactants, bleaching agents, mediators, anti-corrosion agents, builders, anti-redeposition agents, optical brighteners, dyes, pigments, perfumes, caustics, abrasives and preservatives, etc.

The spent culture medium of the production host can be used as such, or the host cells may be removed, and/or it may be concentrated, filtrated or fractionated. It may also be dried. The enzyme preparation and the composition comprising the serine protease enzyme of the invention may be in the form of liquid, powder, granulate or tablets. The enzyme may be in immobilized form in the preparation or in the composition.

Also within the invention is the use of the serine protease enzyme or the enzyme preparation of the invention for detergents, for treating fibers, for treating proteinaceous material such as wool, hair, leather, silk, for treating food or feed, or for any applications involving modification, degradation or removal of proteinaceous material. Particularly, the enzyme or enzyme preparation is useful as a detergent additive in detergent liquids, detergent powders and detergent tablets.

BRIEF DESCRIPTION OF DRAWINGS

FIGS. 1 (1A and 1B) shows the nucleotide sequence of the *Malbranchea* ALKO4122 protease gene, its partial promoter (50 nucleotides upstream from ATG) and terminator sequences (60 nucleotides downstream from the stop codon) and the deduced amino acid sequence of the encoded protease. The putative signal peptide, analyzed by SignalP V3.0 program is in lower case letters and underlined. The pro sequence and the deduced amino acids of the pro sequence are in lower case letters. The mature nucleotide and peptide sequences are in capital letters. The three putative intron sequences are in lower case, italic letters and marked by a dotted line below the nucleotide sequence. The stop codon is shown by an asterisk below the sequence. The locations of primers DET27 (5'-sense primer, s) and DET28 (3'-antisense primer, as) used in PCR cloning of the *Malbranchea* ALKO4178 protease gene are underlined using double lines.

FIG. 1A shows the nucleotide sequence of the *Malbranchea* ALKO4122 protease gene and its partial promoter. The protease gene sequence includes nucleotides from 51 to 960, the sequence region encoding the amino acid sequence from Met 1 to Val 279 and the first codon of Ala 280 of the protease.

FIG. 1B shows the nucleotide sequence of the *Malbranchea* ALKO4122 protease gene and its partial terminator. The protease gene sequence includes nucleotides from 961 to 1486 (the stop codon TAA included), the sequence region encoding the amino acid sequence from Ala 280 (the two last codons) to Arg 401 of the protease.

FIGS. 5 (5A and 5B) shows the relative activity of the enzyme at different temperatures and pH values.

FIGS. 7 (7A, 7B, 7D and 7C) describes the stain removal performance of recombinant Malbranchea ALKO4122 protease with blood/milk/ink stain (Art. 117, CO+PES, Serial No. 10-07, old batch, EMPA) at 10-50° C., approx. pH 8, 60 min in the presence of Commercial liquid detergent with concentration of 5 g/l. Savinase® Ultra 16L was used for comparison.

FIGS. 8 (8A, 8B, 8C and 8D) describes the stain removal performance of recombinant Malbranchea ALKO4122 protease with blood/milk/ink stain (Art. 117, CO+PES, Serial No. 11-08, new batch, EMPA) at 10-50° C., approx. pH 8, 60 min in the presence of Commercial liquid detergent with concentration of 5 g/l. Savinase® 16L and Savinase® Ultra 16L were used for comparison.

FIGS. 9 (9A, 9B, 9C, 9D, 9E, 9F, 9G and 9H) shows the performance of recombinant Malbranchea ALKO4122 protease on different stains in Launder Ometer tests in the presence of Commercial liquid detergent with concentration of 5 g/l at 30 and 60° C., 60 min, approx. pH 8. Commercial preparation Savinase® Ultra 16L was used for comparison.

FIGS. 10 (10A and 10B) shows the performance of the protease in the presence of detergent powder.

FIGS. 11 (11A and 11B) shows the stability of the protease during storage at 37° C.

FIGS. 12 (12A and 12B) shows the stability of the protease in detergent.

SEQUENCE LISTING

Figure 2:
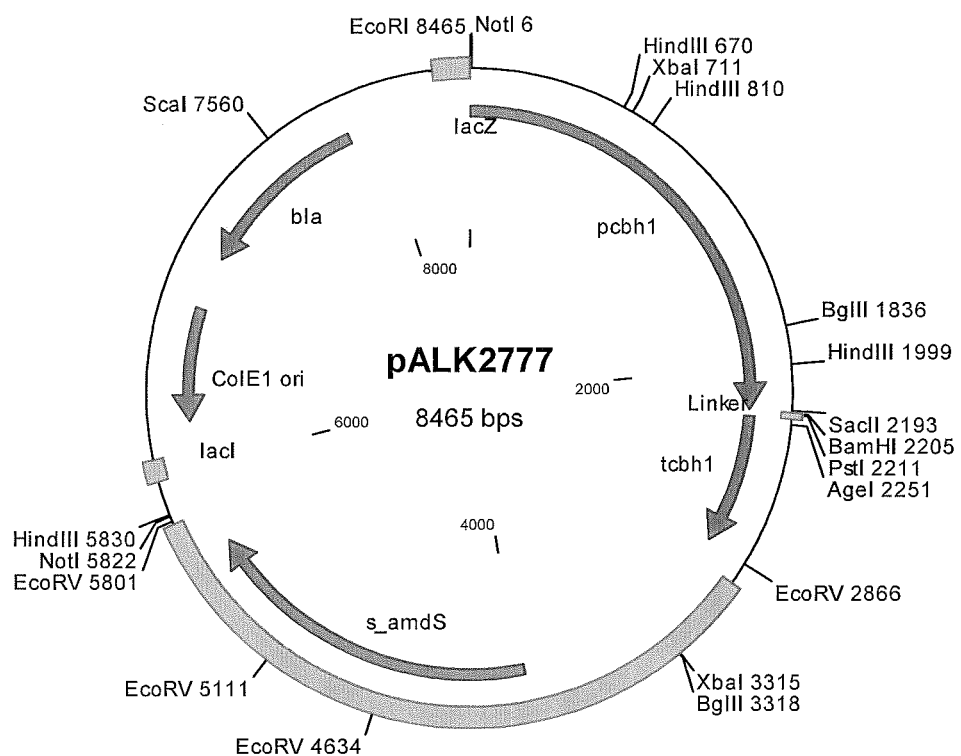
FIG. 2 schematically shows the map of pALK2777 plasmid used as a backbone for constructing the pALK3097 expression cassette. The *Malbranchea* protease gene was ligated between the cbh1 (cel7A) promoter (exact fusion via the SacII site) and terminator sequences (via the BamHI site in the linker) into SacII-BamHI cleaved pALK2777. For further details, see Example 2. The pALK2777 plasmid includes a synthetic amdS marker gene for transformant screening. pcbh1, cbh1 promoter; tcbh1, cbh1 terminator; s_amdS, synthetic amdS marker gene (cDNA); Linker, linker sequence including e.g. BamHI site.

SEQ ID NO:1 Sequence of DET1 sense primer used in PCR for Malbranchea protease probe synthesis.
SEQ ID NO:2 Sequence of DET2 sense primer used in PCR for Malbranchea protease probe synthesis.
SEQ ID NO:3 Sequence of DET3 antisense primer used in PCR for Malbranchea protease probe synthesis.
SEQ ID NO:4 Sequence of DET4 antisense primer used in PCR for Malbranchea protease probe synthesis.
SEQ ID NO:5 Sequence of DET5 sense primer used in PCR for Malbranchea protease probe synthesis.
SEQ ID NO:6 Sequence of a consensus peptide sequence used for design of DET1 sense PCR primer.
SEQ ID NO:7 Sequence of a consensus peptide sequence used for design of DET2 sense PCR primer.
SEQ ID NO:8 Sequence of a consensus peptide sequence used for design of DET3 antisense PCR primer.
SEQ ID NO:9 Sequence of a consensus peptide sequence used for design of DET4 antisense PCR primer.
SEQ ID NO:10 Sequence of the peptide sequence used for design of DET5 sense PCR primer.
SEQ ID NO:11 Sequence of the PCR fragment obtained using DET5 and DET4 in PCR reaction and Malbranchea ALKO4122 genomic DNA as a template. This fragment contains a partial Malbranchea protease gene and is an insert in the plasmid pALK3092.
SEQ ID NO:12 Sequence of the PCR fragment obtained using DET5 and DET4 in PCR reaction and Malbranchea ALKO4178 genomic DNA as a template. This fragment contains a partial *Malbranchea* protease gene and is an insert in the plasmid pALK3093.

SEQ ID NO:13 The nucleotide sequence encoding the full-length amino acid sequence of *Malbranchea* ALKO4122 protease. The full-length gene is included in the plasmid pALK3094. The protease gene sequence cloned from *Malbranchea* ALKO4178 by PCR was identical to this sequence.

SEQ ID NO:14 The full-length amino acid sequence of *Malbranchea* ALKO4122 protease including amino acids Met1 to Arg 401 of the full length protease.

SEQ ID NO:15 The nucleotide sequence encoding the amino acid sequence of the proenzyme form of *Malbranchea* ALKO4122 protease.

SEQ ID NO:16 The amino acid sequence of the proenzyme form of *Malbranchea* ALKO4122 protease including amino acids Gly 21 to Arg 401 of the full length protease.

SEQ ID NO:17 The nucleotide sequence encoding the amino acid sequence of the mature form of *Malbranchea* ALKO4122 protease.

SEQ ID NO:18 The amino acid sequence of the mature form of *Malbranchea* ALKO4122 protease including amino acids Ala 121 to Arg 401 of the full length enzyme.

SEQ ID NO:19 Sequence of the PCR sense primer DET27 used for cloning of the *Malbranchea* ALKO4178 protease gene.

SEQ ID NO:20 Sequence of the PCR antisense primer DET28 used for cloning of the *Malbranchea* ALKO4178 protease gene.

SEQ ID NO:21 Sequence of the PCR sense primer DET17 used in construction of the expression cassette in pALK3097.

SEQ ID NO:22 Sequence of the PCR antisense primer DET18 used in construction of the expression cassette in pALK3097.

DEPOSITS

*Malbranchea* ALKO4122 was deposited at the Centraalbureau Voor Schimmelcultures at Uppsalalaan 8, 3508 AD, Utrecht, the Netherlands on 20 Dec. 2010 and assigned accession number CBS 128533.

*Malbranchea* ALKO4178 was deposited at the Centraalbureau Voor Schimmelcultures at Uppsalalaan 8, 3508 AD, Utrecht, the Netherlands on 5 Jan. 2011 and assigned accession number CBS 128564.

The *E. coli* strain RF8791 including the plasmid pALK3094 was deposited at the Deutsche Sammlung von Mikroorganismen und Zellkulturen GmbH (DSMZ), Inhoffenstrasse 7 B, D-38124 Braunschweig, Germany on 20 Dec. 2010 and assigned accession number DSM 24410.

The *E. coli* strain RF8758 including the plasmid pALK3092 was deposited at the Deutsche Sammlung von Mikroorganismen und Zellkulturen GmbH (DSMZ), Inhoffenstrasse 7 B, D-38124 Braunschweig, Germany on 3 Jan. 2010 and assigned accession number DSM 24426.

The *E. coli* strain RF8759 including the plasmid pALK3093 was deposited at the Deutsche Sammlung von Mikroorganismen und Zellkulturen GmbH (DSMZ), Inhoffenstrasse 7 B, D-38124 Braunschweig, Germany on 3 Jan. 2010 and assigned accession number DSM 24427.

DETAILED DESCRIPTION

The present invention provides a serine protease enzyme of fungal origin. This protease is active at broad pH ranges and has a wide temperature optimum in washing, and particularly good performance at low temperature ranges as well as at moderate and high temperatures. The enzyme is ideal for detergent applications, withstanding typical detergent compositions and being effective at low enzyme levels in detergent solutions. Particularly, the protease is active at application temperatures 0° C.-90° C., the preferred range being from 5° C. to 60° C., more preferably from 10 to 40° C. The protease of the invention is also highly stable in liquid detergent compositions. Thus, the present invention provides a new serine protease for use in detergent and other applications, particularly in liquid formulations. The fungal serine protease can be produced in high-yielding fungal hosts and its down-stream processing, e.g. separation of fermentation broth and mycelia is easy to perform.

Particularly, the present invention provides a serine protease enzyme, which has serine protease activity and comprises an amino acid sequence having at least 66% identity to the amino acid sequence as defined in SEQ ID No:18. Preferably the present invention provides a fungal serine protease enzyme, which has serine protease activity and comprises an amino acid sequence as defined in SEQ ID No:18. A preferred serine protease is derived from *Malbranchea cinnamomea* (Lib.) Oorschot de Hoog.

By "serine protease" or "serine endopeptidase" or "serine endoproteinase" is in connection to this invention meant an enzyme classified as EC 3.4.21 by the Nomenclature of the International Union of Biochemistry and Molecular Biology. Proteases can be classified using group specific inhibitors. The diverse group of serine protease inhibitors includes synthetic chemical inhibitors and natural proteinaceous inhibitors. Thus, the serine protease activity can be determined in an assay based on cleavage of a specific substrate or in an assay using any protein containing substrate with or without a specific inhibitor of serine proteases under suitable conditions.

By the term "serine protease activity" as used in the invention is meant hydrolytic activity on protein containing substrates, e.g. casein, haemoglobin and BSA. The methods for analysing proteolytic activity are well-known in the literature and are referred e.g. in Gupta et al. (2002).

The serine proteases are synthesized as inactive zymogenic precursors or zymogens in the form of a preproenzyme, which are activated by removal of the signal sequence (secretion signal peptide or prepeptide) and the prosequence (propeptide) to yield an active mature form of the enzyme (Chen and Inouye, 2008). This activation process involves action of proteases and may result from limited self-digestive or autocatalytic processing of the serine protease, e.g. during posttranslational phases of the production or in the spent culture medium or during the storage of the culture medium or enzyme preparation. Activation of the proenzyme may also be achieved by adding a proteolytic enzyme capable of converting the inactive proenzyme into active mature enzyme into the culture medium during or after cultivation of the host organism. The shortening of the enzyme can also be achieved e.g. by truncating the gene encoding the polypeptide prior to transforming it to the production host. The "prepro-form" of the serine protease in the present invention means an enzyme comprising the pre- and propeptides. The "pro-form" means an enzyme, which comprises the propeptide but lacks the prepeptide (signal sequence).

The term "mature" means the form of the serine protease enzyme which after removal of the signal sequence (prepeptide) and propeptide comprises the essential amino acids for enzymatic or catalytic activity. In filamentous fungi it is the native form secreted into the culture medium. The first amino acid of mature sequence can be determined by N-terminal sequencing of secreted protease. In case no biochemical data is available the location of the N-terminus can be estimated by aligning the amino acid sequence with mature amino acid sequence(s) of homologous protein(s). The alignment can be performed using e.g. ClustalW2 alignment (www.ebi.ac.uk/Tools/msa/clustalw2).

The largest group of commercial serine proteases are "alkaline serine proteases", which means that the enzymes are active and stable at pH 9 to pH 11 or even at pH 10 to 12.5 (Shimogaki et al., 1991) and have isoelectric point around pH 9. Determination of the optimal pH of the catalytic activity can be carried out in a suitable buffer at different pH values by following the activity on a protein substrate. Typically the detergent proteases perform best when the pH value of the detergent solution in which it works is approximately the same as the pI value for the enzyme. pI can be determined by isoelectric focusing on an immobilized pH gradient gel composed of polyacrylamide, starch or agarose or by estimating the pI from the amino acid sequence, for example by using the pI/MW tool at ExPASy server (http://expasy.org/tools/pi_tool.html; Gasteiger et al., 2003).

The molecular masses of mature alkaline serine proteases range between 15 and 35 kDa, typically from about 25 to 30 kDa (Rao et al. 1998). The molecular mass of the serine protease can be determined by mass spectrometry or on SDS-PAGE according to Laemmli (1970). The molecular mass can also be predicted from the amino acid sequence of the enzyme.

The temperature optima of most natural serine proteases are around 60° C. (Rao et al., 1998). The temperature optimum of a serine protease can be determined in a suitable buffer at different temperatures with casein substrate as described in Example 3 or by using other substrates and buffer systems described in the literature (Gupta et al., 2002).

The mature recombinant *Malbranchea* serine protease according to the invention has a molecular weight of approximately 29 kDa, an optimal temperature of approximately 70° C. at pH 8.5 using 30 min reaction time and casein as a substrate, and active at alkaline pH range such as pH 10 at 50° C. using 30 min reaction time and casein as a substrate. The recombinant *Malbranchea* serine protease has a good performance in the presence of detergents with highly varying properties, at broad, i.e. from low to moderate, and even high temperature ranges. The recombinant *Malbranchea* serine protease, depending on the washing conditions and auxiliary ingredients and additives in detergents, is useful particularly at temperatures at or below 60° C.

To improve the performance of the *Malbranchea* serine protease in varying industrial applications, such as in detergents, it is desirable to improve the properties of the native enzyme. These properties include e.g. storage stability, stability in the presence or absence of detergent, pH stability, oxidative stability or resistance against bleaching agents and substrate specificity. The autoproteolytic activity of the enzyme has an effect on the storage stability and it should be as low as possible. It is also self-evident that for example in laundry and dish washing compositions the wash performance of the modified protease should not be impaired in comparison to the parent or precursor protease enzyme. In other words it is desirable that the enzyme variants have similar or even improved wash performance and stain removal properties when compared to the parent serine protease.

The produced protease enzymes, particularly the serine proteases can be purified by using conventional methods of enzyme chemistry, such as salt preparation, ultrafiltration, ion exchange chromatography, affinity chromatography, gel filtration and hydrophobic interaction chromatography. Purification can be monitored by protein determination, enzyme activity assays and by SDS polyacrylamide gel electrophoresis. The enzyme activity and stability of the purified enzyme at various temperature and pH values as well as the molecular mass and the isoelectric point can be determined.

Figure 4:
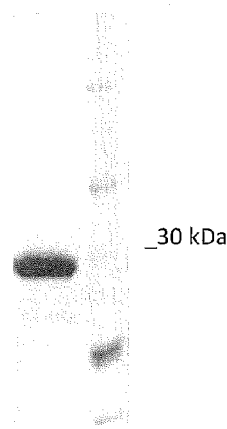
FIG. 4 shows the partially purified recombinant protein analysed on 12% SDS PAGE gel. Lane 1. Sample of the partially purified *Malbranchea* protease, Lane 2. MW marker (Page Ruler Unstained Protein Ladder, Fermentas).

The purification of a recombinant serine protease of the present invention has been demonstrated in Example 4. The centrifuged and filtered culture supernatant was applied to HiPrep 26/10 Desalting column (from GE Healthcare) equilibrated in 20 mM MES pH 5.3. A gel filtered sample was applied to a 1 mL S Sepharose HP column (from GE Healthcare) equilibrated in 20 mM MES pH 5.3. Proteins were eluted using increasing NaCl gradient (0.5 M). Protease containing fractions were pooled and concentrated using Amicon Ultra-4 10,000 CO Centrifugal filter devices MILLIPORE. A sample was further purified using Superdex 75 gel filtration column equilibrated with 20 mM MES, 150 mM NaCl pH 5.3. Protease contains fractions were pooled. A final sample was analysed on SDS PAGE gel FIG. 4. Naturally, it is possible to separate the enzyme of the present invention by using other known purification methods instead, or in addition to the methods described herein. The recombinant serine protease was purified as described in Example 4 and used for characterization of pH and temperature profiles as described in Example 5.

Protease activity is generally based on degradation of soluble substrates. In detergent application proteases have to work on substances which are at least partly insoluble. Thus an important parameter for a detergent protease is the ability to adsorb to and hydrolyse these insoluble fragments.

The serine protease enzyme of the invention may be derived from any organism including bacteria, archaea, fungi, yeasts and even higher eukaryote, such as plants. Preferably said enzyme originates from a fungus, including filamentous fungi and yeasts, for example from a genus selected from the group comprising *Malbranchea*. Fungal alkaline proteases are advantageous to the bacterial proteases due to the ease of down-stream processing to produce a microbe-free enzyme or enzyme composition. Mycelium can be easily removed through filtration techniques prior to the purification of the enzyme.

Mild odor of fungal fermentation products of the present invention is a benefit over *Bacillus* derived products which typically have an unpleasant odor. Therefore less perfume is needed for the final composition for covering the odor and this makes the product suitable also for applications where the use of perfumes is not desirable.

The present invention relates to a fungal serine protease, which has a good performance in the presence of detergents with highly varying properties, at broad, i.e. from low to moderate temperature ranges from 0° C. to 90° C., preferably at temperatures ranging between 5 and 60° C., and particularly preferably at temperatures ranging between 10 and 40° C.

In the present invention good performance in presence of detergent means that the enzyme, in this case the recombinant fungal serine protease of the invention, functions at lower temperature ranges than many commercial subtilisins. In other words, good performance means that the enzyme is capable of degrading or removing proteinaceous stains or material at low to moderate temperature ranges, but especially at lower temperature ranges than the present commercial subtilisin products, for example the commercial subtilisin enzyme product Savinase® or Savinase® Ultra 16L (Novozymes A/S, DK).

The fungal serine protease of the invention, depending on the washing conditions and auxiliary ingredients and additives in detergents, is useful particularly in temperatures at or below 60° C. The enzyme functions also at or below 50° C., at or below 40° C., at or below 30° C. at or below 20° C. and at or below 10° C. It is particularly surprising that a thermophilic enzyme having a temperature optimum around 70° C. is effective and useful at temperatures below 40° C., even at temperatures below 30° C.

In the presence of a detergent, the fungal serine protease of the invention functions at temperatures as defined above and particularly, said fungal serine protease has a good performance in the presence of detergent at or below 40° C. Stain removal performance of the fungal serine protease from *Malbranchea* in varying test conditions, on different stains, measured as deltaL* is by far better than the performance of the commercial products, Savinase® and Savinase® Ultra 16L (Novozymes A/S, DK). The results are shown in Examples 6 to 8 and in FIGS. 6 to 10.

According to a preferred embodiment of the invention the recombinant fungal serine protease enzyme is a polypeptide having serine protease activity and comprising an amino acid sequence of the mature *Malbranchea* ALKO4122 protease as defined in SEQ ID No:18 or an amino acid sequence having at least 66% identity to the amino acid sequence of the mature *Malbranchea* ALKO4122 protease as defined in SEQ ID No:18.

Preferred enzymes show at least 66%, preferably at least 70%, more preferably at least 75%, even more preferably at least 80% identity. Still more preferably the amino acid sequences show at least 85% or at least 90% or 95%, more preferably at least 98%, most preferably 99% identity to the amino acid sequence of SEQ ID No:18. Suitably the identities of the enzymes are compared using the corresponding mature sequence regions.

The serine protease of the present invention in derivable from *Malbranchea*, preferably from *Malbranchea cinnamomea* (Lib.) Oorschot de Hoog (Synonym of *Malbranchea pulchella* var. *sulfurea* (Miehe) Cooney & R. Emers.), which is a member of EC3.4.21. According to the particularly preferred embodiment the serine protease enzyme of the invention is derivable from the *Malbranchea* ALKO4122 strain deposited under accession number CBS 128533 or from the strain *Malbranchea* ALKO4178 deposited under accession number CBS 128564. The protease of *Malbranchea* ALKO4178 is essentially identical with the protease of *Malbranchea* ALKO4122 strain.

By the term "identity" is here meant the identity between two amino acid sequences compared to each other within the corresponding sequence region having approximately the same amount of amino acids. For example, the identity of a full-length or a mature sequence of the two amino acid sequences may be compared. The amino acid sequences of the two molecules to be compared may differ in one or more positions, which however does not alter the biological function or structure of the molecules. Such variation may occur naturally because of different host organisms or mutations in the amino acid sequence or they may be achieved by specific mutagenesis. The variation may result from deletion, substitution, insertion, addition or combination of one or more positions in the amino acid sequence. The identity of the sequences is measured by using ClustalW2 alignment (www.ebi.ac.uk/Tools/msa/clustalw2) with default settings (Protein Weight Matrix: Gonnet, Gap open: 10, Gap extension: 0.20, Gap distances 5).

One preferred embodiment of the invention is a mature fungal serine protease enzyme having serine protease activity and an amino acid sequence of the *Malbranchea* ALKO4122 protease as defined in SEQ ID No:18. The mature enzyme lacks the signal sequence or prepeptide and the prosequence or propeptide. The mature serine protease of the invention includes amino acids Ala121 to Arg401 of the full length protease characterized in SEQ ID No:14. Thus, within the scope of the invention is also the full-length *Malbranchea* ALKO4122 protease enzyme having SEQ ID No:14 including the signal sequence (prepeptide) and propeptide as well as the proenzyme form lacking the signal sequence (prepeptide) thus having SEQ ID No:16.

The present invention relates to a fungal serine protease enzyme, the mature form of which has a molecular mass or molecular weight between 20 and 35 kDa, preferably between 25 and 33 kDa, more preferably between 28 and 30 kDa. The most preferred MW is the predicted molecular mass of 29 kDa for the mature polypeptide obtained by using the Compute pI/MW tool at ExPASy server (Gasteiger et al., 2003).

The enzyme of the invention is effective in degrading proteinaceous material at a broad temperature range. The fungal serine protease has a temperature optimum in the range from 30° C. to 80° C. (at least about 10% of the maximum activity), preferably from 40° C. to 80° C. (at least about 20% of the maximum activity), and more preferably between 50° C. and 80° C. (at least about 40% of the maximum activity), most preferably from 60° C. to 80° C. (at least about 65% of the maximum activity), the maximum activity being at 70° C., when measured at pH 8.5 using 30 min reaction time and casein as a substrate as described in Example 5.

The enzyme has a pH optimum in the range from pH 6 to at least pH 10 at 50° C. using 30 min reaction time and casein as a substrate as described in Example 5. In particular, the pH optimum is between pH 6 and pH 10 (at least about 60% of the maximum activity), and more preferably between pH 9 and pH 10 (at least about 70% of the maximum activity), and most preferably at about pH 10.

The serine protease, suitably the fungal serine protease of the invention has "good performance in the presence of detergent", i.e. is capable of degrading or removing proteinaceous stains or material in the presence of detergent at low temperature ranges, specifically at lower temperature ranges than the present commercial subtilisin products, for example the commercial enzyme product Savinase® or Savinase® Ultra 16L (Novozymes A/S, DK). In the presence of a detergent the enzyme of the invention functions well between 5° C. and 60° C., preferably at or below 50° C. The enzyme functions also in temperatures at or below 40° C., or at or below 30° C.

According to a preferred embodiment of the invention the fungal serine protease enzyme is encoded by an isolated polynucleotide sequence which hybridizes under stringent conditions to a polynucleotide or probe sequence included in plasmid pALK3092 comprising the nucleotide sequence SEQ ID No:11 in *E. coli* RF8758, deposited at the Deutsche Sammlung von Mikroorganismen and Zellkulturen (DSMZ) under accession number DSM 24426.

In a similar way, the fungal serine protease enzyme (obtained from *Malbranchea* ALKO4178) of the invention is encoded by an isolated polynucleotide sequence, which hybridizes under stringent conditions to a polynucleotide sequence included in plasmid pALK3093 comprising the nucleotide sequence SEQ ID No:12, deposited in *E. coli* RF8759 under accession number DSM 24427.

Further, the fungal serine protease enzyme of the invention is encoded by an isolated polynucleotide sequence, which hybridizes under stringent conditions to a polynucleotide sequence included in plasmid pALK3094 comprising the nucleotide sequence SEQ ID No:17, deposited in *E. coli* RF8791 under accession number DSM 24410.

In the present invention the *Malbranchea* protease gene was isolated with a probe prepared by PCR using stringent hybridization as described in Example 1d. Standard molecular biology methods can be used in isolation of cDNA or a genomic DNA of the host organism, e.g. the methods described in the molecular biology handbooks, such as Sambrook and Russell, 2001.

Hybridization with a DNA probe, such as for example SEQ ID NO:11, SEQ ID NO:12 or SEQ ID NO:17 consisting of more than 100-200 nucleotides, is usually performed at "high stringency" conditions, i.e. hybridization at a temperature, which is 20-25° C. below the calculated melting temperature (Tm) of a perfect hybrid, the Tm calculated according to Bolton and McCarthy (1962). Usually prehybridization and hybridization are performed at least at 65° C. in 6×SSC (or 6×SSPE), 5×Denhardt's reagent, 0.5% (w/v) SDS, 100 µg/ml denatured, fragmented salmon sperm DNA. Addition of 50% formamide lowers the prehybridization and hybridization temperatures to 42° C. Washes are performed in low salt concentration, e.g. in 2×SSC-0.5% SDS (w/v) for 15 minutes at room temperature (RT), followed in 2×SSC-0.1% SDS (w/v) at RT, and finally in 0.1×SSC-0.1% SDS (w/v) at least at 65° C., or in conditions described in Example 1d.

According to one preferred embodiment the fungal serine protease enzyme of the invention is encoded by an isolated nucleic acid molecule, which encodes a polypeptide comprising the amino acid sequence characterized in SEQ ID No:18, or a polypeptide having at least 66% identity to the amino acid sequence SEQ ID No:18. Preferred enzymes show at least 66%, preferably at least 70%, more preferably at least 75%, even more preferably at least 80% identity. Still more preferably the amino acid sequences show at least 85% or at least 90% or 95%, more preferably at least 98%, most preferably 99% identity to the amino acid sequence of SEQ ID No:18. The identities of the enzymes are compared using the corresponding mature sequence regions.

Thus, within the scope of the invention is a polypeptide sequence, which is encoded by a nucleic acid molecule encoding the amino acid sequence of the full-length serine protease of the invention including the prepeptide (signal sequence) and the propeptide in addition to the mature form of the enzyme, and which amino acid sequence is characterized in SEQ ID No:14.

Also, within the scope of the invention is a polypeptide sequence, which is encoded by a nucleic acid molecule encoding the propeptide form of serine protease enzyme of the invention including the propeptide in addition to the mature form of the enzyme, and which amino acid sequence is characterized in SEQ ID No:16.

One preferred embodiment of the invention is the fungal serine protease enzyme encoded by an isolated nucleic acid molecule, which comprises the nucleotide sequence encoding the mature form of the *Malbranchea* ALKO4122 serine protease having SEQ ID No:18.

According to one preferred embodiment the fungal serine protease enzyme of the invention is encoded by an isolated nucleic acid molecule comprising the nucleotide sequence SEQ ID No:17 encoding the mature form of the *Malbranchea* ALKO4122 enzyme (SEQ ID No:18).

Thus, within the scope of the invention is the polypeptide encoded by the nucleic acid molecule having the nucleotide sequence SEQ ID No:13 comprising the "coding sequence" for the enzyme. The expression "coding sequence" means the nucleotide sequence which initiates from the translation start codon (ATG) and stops at the translation stop codon (TAA, TAG or TGA). The translated full-length polypeptide starts usually with methionine and may comprise intron regions.

Also, within the scope of the invention is a fungal serine protease enzyme encoded by a nucleic acid molecule comprising the nucleotide sequence SEQ ID NO:15, which encodes the *Malbranchea* ALKO4122 proenzyme form.

According to another preferred embodiment of the invention the fungal serine protease is encoded by the polynucleotide sequence included in plasmid pALK3094 comprising the nucleotide sequence SEQ ID No:13 in *E. coli* RF8791, deposited under accession number DSM 24410.

One embodiment of the invention is the serine protease enzyme produced from a recombinant expression vector comprising the nucleic acid molecule, which encodes the fungal serine protease enzyme as characterized above operably linked to regulatory sequences capable of directing the expression of said serine protease enzyme in a suitable host. Construction of said recombinant expression vector and use of said vector is described in more detail in Example 2.

Suitable hosts for production of the fungal serine protease enzyme are homologous or heterologous hosts, such as the microbial hosts including bacteria, yeasts and fungi. Filamentous fungi, such as *Trichoderma, Aspergillus, Fusarium, Humicola, Chrysosporium, Neurospora, Rhizopus, Penicillium, Myceliophthora*, and *Mortierella*, are preferred production hosts due to the ease of down-stream processing and recovery of the enzyme product. Suitable hosts include species such as *T. reesei, A. niger, A. oryzae, A. sojae, A. awamori*, or *A. japonicus* type of strains, *F. venenatum* or *F. oxysporum, H. insolens* or *H. lanuginosa, N. crassa* and *C. lucknowense*, some of which are listed as enzyme production host organisms in e.g. AMFEP 2009 list of commercial enzymes (www.amfep.org/list.html). More preferably, the enzyme is produced in a filamentous fungal host of the genus *Trichoderma* or *Aspergillus*, such as *T. reesei* or *A. niger, A. oryzae* or *A. awamori*. According the most preferred embodiment of the invention the fungal serine protease enzyme is produced in *T. reesei*.

The present invention relates also to an isolated nucleic acid molecule comprising a polynucleotide sequence encoding the serine protease enzyme selected from the group consisting of:

(g) a nucleic acid molecule encoding a polypeptide having serine protease activity and comprising the amino acid sequence as depicted in SEQ ID No:18;

(h) a nucleic acid molecule encoding a polypeptide having serine protease activity and at least 66% identity to the amino acid sequence of SEQ ID No:18;

(i) a nucleic acid molecule comprising the coding sequence of the nucleotide sequence as depicted in SEQ ID No: 17;

(j) a nucleic acid molecule comprising the coding sequence of the polynucleotide sequence contained in DSM 24410;

(k) a nucleic acid molecule the coding sequence of which differs from the coding sequence of a nucleic acid molecule of any one of (c) to (d) due to the degeneracy of the genetic code; and (l) a nucleic acid molecule hybridizing under stringent conditions to a nucleic acid molecule contained in DSM 24426, or SEQ ID No:17 encoding a polypeptide having serine protease activity and an amino acid sequence which shows at least 66% identity to the amino acid sequence as depicted in SEQ ID No:18.

The nucleic acid molecule of the invention may be RNA or DNA, wherein the DNA may constitute of the genomic DNA or cDNA.

Standard molecular biology methods can be used in isolation and enzyme treatments of the polynucleotide sequence encoding the fungal serine protease of the invention, including isolation of genomic and plasmid DNA, digestion of DNA to produce DNA fragments, sequencing, E. coli transformations etc. The basic methods are described in the standard molecular biology handbooks, e.g. Sambrook and Russell, 2001.

Isolation of the Malbranchea protease gene encoding the Malbranchea ALKO4122 polypeptide is described in Example 1. Briefly, the PCR fragment obtained by using the degenerate oligonucleotide primers (SEQ ID No: 5 and SEQ ID No: 4) in the PCR reaction was used to isolate the protease gene from Malbranchea ALKO4122. The genomic fragment including the protease gene was ligated into pBluescript II KS+ vector. The full-length Malbranchea protease gene was included in the plasmid pALK3094 deposited in E. coli to the DSMZ culture collection under accession number DSM 24410. The deduced amino acid sequence of the serine protease was analyzed from the DNA sequence.

The nucleotide sequence of Malbranchea ALKO4122 protease (SEQ ID No: 13) its partial promoter and terminator sequences and the deduced amino acid sequence (SEQ ID No:14) are presented in FIG. 1A-B. The length of the gene is 1436 by (including the stop codon). Three putative introns were found having the length of 72, 87 and 71 bps. The deduced protein sequence consists of 401 amino acids including a predicted signal sequence of 20 amino acids (SignalP V3.0; Nielsen et al., 1997 and Nielsen and Krogh, 1998) and a predicted propeptide from Gly21 to Asp120. The predicted molecular mass was 28.5 kDa for the mature polypeptide and the predicted pI was 6.15. These predictions were made using the Compute pI/MW tool at ExPASy server (Gasteiger et al., 2003). The deduced amino acid sequence contained three possible N-glycosylation sites (Asn134, Asn172 and Asn277), but according to CBS Server NetNGlyc V1.0 only two sites, Asn134 and Asn277 are likely. The homologies to the published protease sequences were searched using the BLASTP program, version 2.2.25 at NCBI (National Center for Biotechnology Information) (Altschul et al., 1990). The identity values of the mature Malbranchea protease sequence to the corresponding regions of the most homologous sequences were obtained by using ClustalW2 alignment (Matrix: Gonnet, Gap open: 10, Gap extension: 0.20, Gap distances 5; available e.g. in www.ebi.ac.uk/Tools/msa/clustalw2/). The results are shown in Table 2.

The highest identity values obtained from the BLASTP search for the mature Malbranchea ALKO4122 protease of the present invention (SEQ ID NO: 18) were as follows: 65%, for Coccidioides posadasii putative subtilisin-like protease (EER24932.1) and Coccidioides immitis hypothetical protein CIMG_09197 (XP_001239485.1), 65% for Uncinocarpus reesii hypothetical protein UREG_05170 (EEP80328.1), 64% for Coccidioides immitis hypothetical protein CIMB_01394 (XP_001247623.1), Coccidioides posadasii putative subtilisin-like protease (EER23662.1), Uncinocarpus reesii hypothetical protein (EEP81307.1) and Arthroderma otae alkaline proteinase (EEQ28657.1). The highest identities for the sequences in patent division were 55% for SEQ ID NO:2 in U.S. Pat. No. 5,962,765 (AAE30270.1; protease from Metarhizium anisopliae) and SEQ ID:15 in WO 8807581 (AAA54276.1; protease from Tritirachium album). The mature Malbranchea ALKO4122 protease sequence (SEQ ID NO:18) was aligned with the mature sequences of the above homologous sequences using ClustalW2 alignment. The identity values (score %) obtained by using ClustalW2 alignment (www.ebi.ac.uk/Tools/msa/clustalw2/) obtained were from 63%-65%.

Thus, within the scope of the invention is an isolated polynucleotide sequence or isolated nucleic acid molecule, which encodes a fungal serine protease enzyme or polypeptide comprising the amino acid sequence of the mature form of the Malbranchea ALKO4122 enzyme characterized in SEQ ID No: 18, 15, i.e. amino acids Ala121 to Arg401 of the full length serine protease of SEQ ID No:14.

The nucleic acid molecule is preferably a molecule comprising the coding sequence as depicted in SEQ ID No:17, which encodes the mature form of the fungal serine protease enzyme of this invention.

The isolated nucleic acid molecule of the invention may be a molecule comprising the coding sequence of the polynucleotide sequence contained in DSM 24410, DSM 24426 or DSM 24427. DSM 24426 carries the nucleotide sequence of the PCR fragment (SEQ ID No:11) used in cloning the full length Malbranchea ALKO4122 protease gene. DSM 24427 carries the nucleotide sequence of the PCR fragment (SEQ ID No:12) obtained from Malbranchea ALKO4178. DSM 24410 carries the nucleotide sequence of the full length Malbranchea ALKO4122 protease gene (SEQ ID No:13).

The nucleic acid molecule of the invention may also be an analogue of the nucleotide sequence characterized in above. The "degeneracy" means analogues of the nucleotide sequence, which differ in one or more nucleotides or codons, but which encode the recombinant protease of the invention.

The nucleic acid molecule may also be a nucleic acid molecule hybridizing under stringent conditions to a PCR probe contained in plasmids pALK3092 or pALK3093 deposited in E. coli under the accession numbers DSM 24426 and DSM 24427, respectively, or to a DNA sequence SEQ ID NO: 17 encoding a mature polypeptide having serine protease activity and an amino acid sequence. The hybridizing DNA may originate from a fungus belonging to species Malbranchea or it may originate from other fungal species.

Thus, within the scope of the invention is an isolated nucleic acid molecule comprising a nucleotide sequence as depicted in SEQ ID No:17 and analogues thereof.

The present invention relates also to a recombinant expression vector or recombinant expression construct, which can be used to propagate or express the nucleic acid sequence encoding the chosen serine protease in a suitable prokaryotic or eukaryotic host. The recombinant expression vector comprises DNA or nucleic acid sequences which facilitate or direct expression and secretion of the serine protease encoding sequence in a suitable host, such as promoters, enhancers, terminators (including transcription and translation termination signals) and signal sequences operably linked the polynucleotide sequence encoding said serine protease. The expression vector may further comprise marker genes for selection of the transformant strains or the selection marker may be introduced to the host in another vector construct by co-transformation. Said regulatory sequences may be homologous or heterologous to the production organism or they may originate from the organism, from which the gene encoding the serine protease is isolated.

Examples of promoters for expressing the serine protease of the invention in filamentous fungal hosts are the promoters of A. oryzae TAKA amylase, alkaline protease ALP and triose phosphate isomerase, Rhizopus miehei lipase, Aspergillus niger or A. awamori glucoamylase (glaA), Fusarium oxysporum trypsin-like protease, Chrysosporium lucknowense cellobiohydrolase 1 promoter, Trichoderma reesei cellobiohydrolase I (Cel7A) etc.

In yeast, for example promoters of *S. cerevisiae* enolase (ENO-1), galactokinase (GAL1), alcohol dehydrogenase (ADH2) and 3-phosphoglycerate kinase can be used to provide expression.

Examples of promoter sequences for directing the transcription of the serine protease of the invention in a bacterial host are the promoter of lac operon of *Escherichia coli*, the *Streptomyces coelicolor* agarase dagA promoter, the promoter of the *B. licheniformis* alpha-amylase gene (amyL), the promoter of the *B. stearothermophilus* maltogenic amylase gene (amyM), the promoters of the *B. sublitis* xylA and xylB genes, etc.

Suitable terminators include those of the above mentioned genes or any other characterized terminator sequences.

Suitable transformation or selection markers include those which complement a defect in the host, for example the dal genes from *B. subtilis* or *B. licheniformis* or *Aspergillus* amdS and niaD. The selection may be based also on a marker conferring antibiotic resistance, such as ampicillin, kanamycin, chloramphenicol, tetracycline, phleomycin or hygromycin resistance.

Extracellular expression of the serine protease of the invention is preferable. Thus, the recombinant vector comprises sequences facilitating secretion in the selected host. The signal sequence of the serine protease of the invention or the presequence or prepeptide may be included in the recombinant expression vector or the natural signal sequence may be replaced with another signal sequence capable of facilitating expression in the selected host. Thus, the chosen signal sequence may be homologous or heterologous to the expression host. Also a natural propeptide may be replaced with another propeptide. The propeptide may be homologous or heterologous to the expression host.

Examples of suitable signal sequences are those of the fungal or yeast organisms, e.g. signal sequences from well expressed genes. Such signal sequences are well known from the literature.

The recombinant vector may further comprise sequences facilitating integration of the vector into the host chromosomal DNA to obtain stable expression and/or to facilitate targeting to a certain position in the host genome.

The *Malbranchea* ALKO4122 protease of the invention with its own signal sequence was expressed from the *T. reesei* cbh1 (cel7A) promoter as described in Example 2. The expression construction used to transform the *T. reesei* host included also cbh1 terminator and synthetic amdS marker for selecting the transformants from the untrasformed cells.

The present invention relates also to host cells comprising the recombinant expression vector as described above. Suitable hosts for production of the fungal serine protease enzyme are homologous or heterologous hosts, such as the microbial hosts including bacteria, yeasts and fungi. Production systems in plant or mammalian cells are also possible.

Filamentous fungi, such *Trichoderma, Aspergillus, Fusarium, Humicola, Chrysosporium, Neurospora, Rhizopus, Penicillium, Myceliophthora,* and *Mortierella,* are preferred production hosts due to the ease of down-stream processing and recovery of the enzyme product. Suitable expression and production host systems are for example the production system developed for the filamentous fungus host *Trichoderma reesei* (EP 244234), or *Aspergillus* production systems, such as *A. oryzae* or *A. niger* (WO 9708325, U.S. Pat. No. 5,843,745, U.S. Pat. No. 5,770,418), *A. awamori, A. sojae* and *A. japonicus*-type strains, or the production system developed for *Fusarium*, such as *F. oxysporum* (Malardier et al., 1989) or *F. venenatum*, and for *Neurospora crassa, Rhizopus miehei, Mortierella alpinis, H. lanuginosa* or *H. insolens* or for *Chrysosporium lucknowense* (U.S. Pat. No. 6,573,086). Suitable production systems developed for yeasts are systems developed for *Saccharomyces, Schizosaccharomyces,* or *Pichia pastoris*. Suitable production systems developed for bacteria are a production system developed for *Bacillus*, for example for *B. subtilis, B. licheniformis, B. amyloliquefaciens,* for *E. coli,* or for the actinomycete *Streptomyces*. Preferably the serine protease of the invention is produced in a filamentous fungal host of the genus *Trichoderma* or *Aspergillus*, such as *T. reesei*, or *A. niger, A. oryzae, A. sojae, A. awamori* or *A. japonicus*-type strains. According the most preferred embodiment of the invention the fungal serine protease enzyme is produced in *T. reesei*.

The present invention relates also to a process for producing a polypeptide having serine protease activity, said process comprising the steps of culturing the natural or recombinant host cell carrying the recombinant expression vector for a serine protease of the invention under suitable conditions and optionally isolating said enzyme. The production medium may be a medium suitable for growing the host organism and containing inducers for efficient expression. Suitable media are well-known from the literature.

The invention relates to a polypeptide having serine protease activity, said polypeptide being encoded by the nucleic acid molecule of the invention and which is obtainable by the process described above.

The invention further relates to a process for obtaining an enzyme preparation comprising a polypeptide, which has serine protease activity, said process comprising the steps of culturing a host cell carrying the expression vector of the invention and either recovering the polypeptide from the cells or separating the cells from the culture medium and obtaining the supernatant having serine protease activity.

The present invention relates also to an enzyme preparation, which comprises the serine protease enzyme characterized above. The enzyme preparation or composition has serine protease activity and is obtainable by the process according to the invention.

Within the invention is an enzyme preparation as well as composition comprising the serine protease of the invention.

The enzyme preparation or composition (e.g. detergent formulation) containing the protease enzyme of the invention may further comprise other enzymes selected from the group consisting of proteases (other protease than that of the invention), amylases, lipases, cellulases, cutinases, pectinases, mannanases, xylanases and oxidases, such as a laccase or peroxidase with or without a mediator. These enzymes are expected to enhance the performance of the serine proteases of the invention e.g. by removing the carbohydrates and oils or fats present in the material to be handled. Said enzymes may be natural or recombinant enzymes produced by the host strain or may be added to the culture supernatant after the production process.

Said enzyme preparation or composition may further comprise one or more suitable additives selected from the group consisting of surfactants or surface active agents, buffers, anti-corrosion agents, stabilizers, bleaching agents, mediators, builders, caustics, abrasives and preservatives, optical brighteners, antiredeposition agents, dyes, pigments, perfumes etc.

Surfactants are useful in emulsifying grease and wetting surfaces. The surfactant may be a non-ionic including semipolar and/or anionic and/or cationic and/or zwitterionic.

Buffers may be added to the enzyme preparation or composition to modify pH or affect performance or stability of other ingredients.

Suitable stabilizers include polyols such as propylene glycol or glycerol, a sugar or sugar alcohol, lactic acid, boric acid, or boric acid derivatives, peptides, etc.

Bleaching agent is used to oxidize and degrade organic compounds. Examples of suitable chemical bleaching systems are $H_2O_2$ sources, such as perborate or percarbonate with or without peracid-forming bleach activators such as tetraacetylethylenediamine, or alternatively peroxyacids, e.g. amide, imide or sulfone type. Chemical oxidizers may be replaced partially or completely by using oxidizing enzymes, such as laccases or peroxidases. Many laccases do not function effectively in the absence of mediators.

Builders or complexing agents include substances, such as zeolite, diphosphate, triphosphate, carbonate, citrate, etc. The enzyme preparation may further comprise one or more polymers, such as carboxymethylcellulose, poly(ethylene glycol), poly(vinyl alcohol), poly(vinylpyrrolidone), etc. Also, softeners, caustics, preservatives for preventing spoilage of other ingredients, abrasives and substances modifying the foaming and viscosity properties can be added.

According to one preferred embodiment of the invention said enzyme preparation or composition comprising said enzyme is in the form of liquid, powder, granulate or tablets. According to a preferred embodiment of the invention said composition is a detergent formulation in the form of liquid, powder, granulate or tablets. Further, the enzyme in the preparation or composition may be in the form of immobilized enzyme.

The serine protease of the present invention may like other proteases, particularly alkaline proteases be used in the detergent, protein, brewing, meat, photographic, leather, dairy and pharmaceutical industries (Kalisz, 1988; Rao et al., 1998). For example, it may be used as an alternative to chemicals to convert fibrous protein waste (e.g. horn, feather, nails and hair) to useful biomass, protein concentrate or amino acids (Anwar and Saleemuddin, 1998). The use of the serine protease of the present invention may like other enzymes prove successful in improving leather quality and in reducing environmental pollution and saving energy and it may like alkaline proteases be useful in synthesis of peptides and resolution of the mixture of D,L-amino acids. Subtilisin in combination with broad-spectrum antibiotics in the treatment of burns and wounds is an example of the use of serine proteases in pharmaceutical industry, therefore the fungal serine protease of the present invention may also find such use and may also like alkaline proteases be applicable in removal of blood on surgical equipments and cleaning contact lenses or dentures. Like alkaline protease from *Conidiobolus coronatus*, the fungal serine protease of the present invention may be used for replacing trypsin in animal cell cultures. The proteases of the invention can also be used in cleaning of membranes and destruction of biofilms. In baking the proteases can be used e.g. in destruction of the gluten network and in other food applications in hydrolysis of food proteins, e.g proteins in milk. They can also be used e.g. in treating yeast, rendering (extracting more protein from animal bones), creating new flavours, reducing bitterness, changing emulsifying properties, generating bioactive peptides and reducing allergenicity of proteins. The substrates include animal, plant and microbial proteins.

Detergent industry, particularly the laundry detergent industry, has emerged as the single major consumer of proteases active at high pH range (Anwar and Saleemuddin, 1998). The ideal detergent protease should possess broad substrate specificity to facilitate the removal of large variety of stains due to food, grass, blood and other body secretions. It has to be active in the pH and ionic strength of the detergent solution, the washing temperature and pH, and tolerate mechanical handling as well as the chelating and oxidizing agents added to detergents. Due to awareness for energy conservation, it is currently desirable to use the protease at lower temperatures.

The present invention relates also to the use of the serine protease enzyme or the enzyme preparation for detergents, treating textile fibers, for treating proteinaceous materials, such as wool, hair, silk, leather, for treating feed or food, or for any application involving modification, degradation or removal of proteinaceous material.

One preferred embodiment of the invention is therefore the use of the serine protease enzyme as characterized above as a detergent additive useful for laundry detergent and dish wash compositions, including automatic dish washing compositions.

The expression "detergent" is used to mean substance or material intended to assist cleaning or having cleaning properties. The term "detergency" indicates presence or degree of cleaning property. The degree of cleaning property can be tested on different proteinaceous or protein containing substrate materials or stains or stain mixtures bound to solid, water-insoluble carrier, such as textile fibers or glass. Typical proteinaceous material includes blood, milk, ink, egg, grass and sauces. For testing purposes variety of proteinaceous stains are commercially available. The function of the detergent enzyme is to degrade and remove the protein-containing stains. Test results depend on the type of stain, the composition of the detergent and the nature and status of textiles used in the washing test (Maurer, 2004).

The term "low temperature" in context of the present application means temperature ranges from 10° C. to 30° C., which according to the Experiments are not optimal for the performance of many of the presently available enzyme preparations, particularly the detergent enzyme preparations. By the term "moderate temperature" is meant a temperature range from 30° C. to 60° C.

The term "applicable at low or moderate temperature ranges" includes industrial applications in which it is desirable that the enzyme functions effectively at low or moderate temperature ranges (10° C. to 60° C.). Such applications include their use in food, feed and leather industry, pharmaceuticals, diagnostics, waste management and silver recovery. As meant herein, these applications exclude the use of the serine protease enzyme of the invention as a biocontrol agent in biological control of plant pathogenic fungi and nematodes.

In the present invention the term "detergent stability" means that the enzyme or enzyme variant sufficiently retains its activity in detergent solution, during storage and/or washing. Therefore it is efficient in degrading or removing proteinaceous stains or material in the presence of a detergent such as the Ecolabel Reference Detergent, light duty (wfk Testgewebe GmbH) or the Commercial liquid detergent as described in Table 3 of Example 6. The stability may be assayed by determining the residual activity e.g. after several days incubation (at 37° C.) in detergent. The residual protease activity may be determined using the method described in Example 3 or any other method disclosed in the literature (Gupta et al. 2002).

The term "effective amount" of a serine protease refers to the quantity of the protease enzyme necessary to achieve the enzymatic activity in the specific detergent composition. Preferably the detergent composition of the invention comprises from about 0.0001% to about 10% by weight of the detergent composition of a protease variant of the invention, more preferably from 0.001% to about 1%, still more preferably from 0.001% to about 0.5%.

Typically, the wash performance of protease is measured as "stain removal efficiency" or "stain removal effect" or "degree of cleaning property" meaning a visible and measureable increase of lightness or change in colour of the stained material, e.g. in artificially soiled swatches or test cloths. Lightness or change in colour values can be measured, for example by measuring the colour as reflectance values with a spectrophotometer using L*a*b* colour space coordinates as described in Examples 6 to 8. Fading or removal of proteinaceous stain indicating of the protease performance (stain removal efficiency) is calculated for example as ΔL*, which means lightness value L* of enzyme treated fabric minus lightness value L* of fabric treated with washing liquor without enzyme (enzyme blank or control). The presence of detergent may improve the performance of the enzyme in removing the stains. The serine protease of the present invention degrades various kinds of proteinaceous stains under alkaline conditions in the presence of detergents with different compositions (Examples 6-8).

As shown in Example 6 the serine protease of the invention removed the blood/milk/ink stain at 10-50° C. and especially at or below 30° C. in Commercial liquid detergent considerably better than the commercial protease preparations Savinase® 16L and Savinase® Ultra 16L (FIGS. 6 and 7). The enzyme preparations were dosed as activity units. The same effect was observed also when the dosing was calculated as amount of added protein (FIG. 8). It is surprising that *Malbranchea* ALKO4122 protease shows optimal stain removal performance at very broad temperature range and especially at low temperatures, like 10-30° C., despite of its high temperature optimum at analytical conditions on casein substrate (approx. 70° C., FIG. 5A). Savinase® that has similar temperature profile in analytical conditions (FIG. 5A) shows clearly lower performance at cold washing temperatures. The results of these tests indicate that the protease according to the invention has excellent performance with liquid detergent at broad temperature range and even at very cold washing temperatures.

In addition to the different blood/milk/ink stains the *Malbranchea* ALKO4122 protease was effective in removing stains, such as grass and cocoa when tested in liquid detergent at 30 and 60° C. Treatments were performed in ATLAS LP-2 Launder-Ometer and enzyme dosed as activity. Results (FIGS. 9A-H) show that the *Malbranchea* proteasea was effective on several stains at both temperatures 30 and 60° C. and showed better stain removal performance compared to Savinase® Ultra 16L. *Malbranchea* ALKO4122 was effective also on groundnut oil/milk and egg yolk stains.

The performance of the *Malbranchea* ALKO4122 protease was tested also with Commercial traditional detergent powder containing bleaching agents and optical brighteners and with ECE Reference detergent 77 without optical brighteners and bleaching agents at 50° C. at pH 10.5 or 10, respectively, as described in Example 8. The ability of the enzyme in removing blood/mills/ink stain on polyester-cotton material was assayed. As shown in FIGS. 10 A and B the protease of the invention is suitable also for powder detergents at very alkaline conditions and the effect was similar compared to Savinase® Ultra 16L, when each enzyme preparation was dosed as activity units.

Figure 11A:
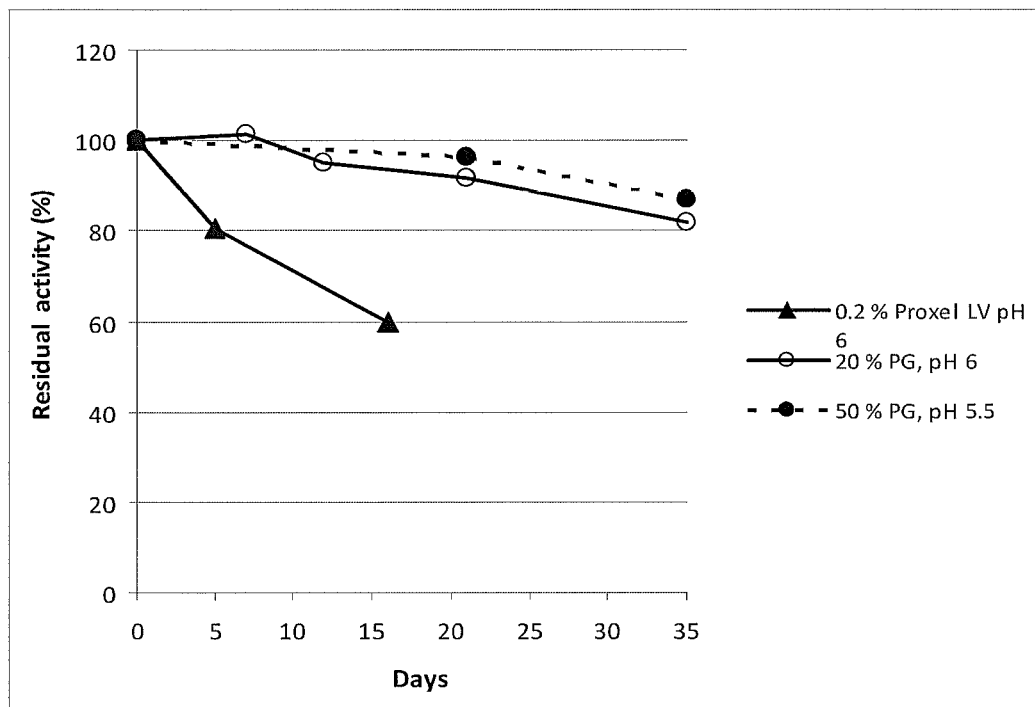
FIG. 11A shows the stability of recombinant Malbranchea ALKO4122 protease during storage at 37° C., when preserved/stabilized with Proxel LV or propylene glycol (PG).
Figure 12A:
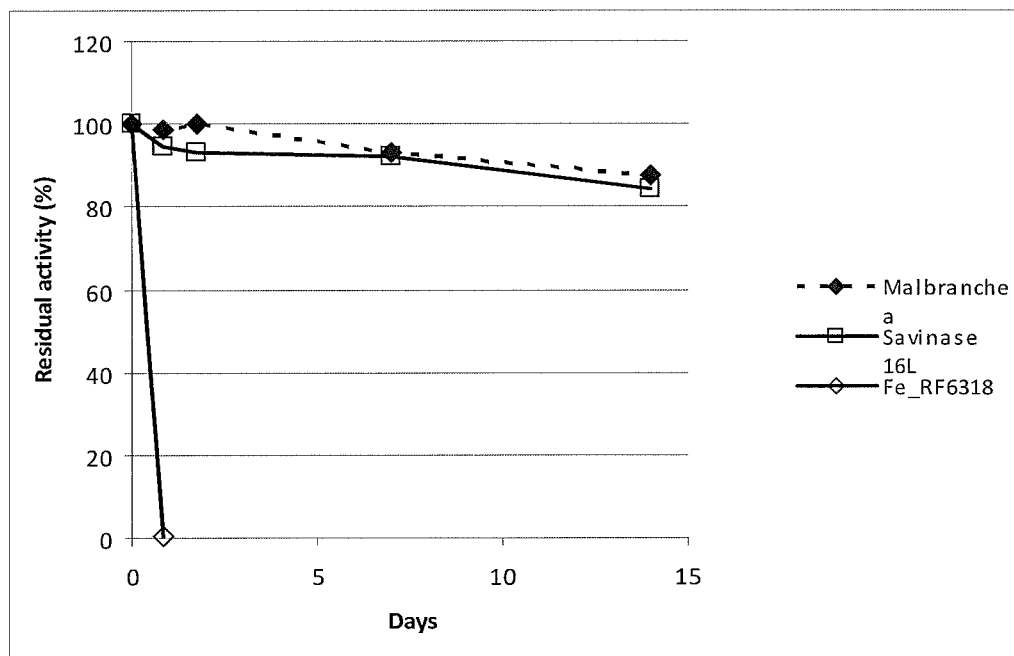
FIG. 12A shows the stability of recombinant Malbranchea ALKO4122 protease in Ecolabel Reference Detergent at 37° C. pH approx. 7. Commercial preparation Savinase® Ultra 16L and recombinant protease Fe_RF6318 (WO2010125174A1) were used for comparison. The amount of enzyme preparation used in detergent was 4% (w/w).
Figure 12B:
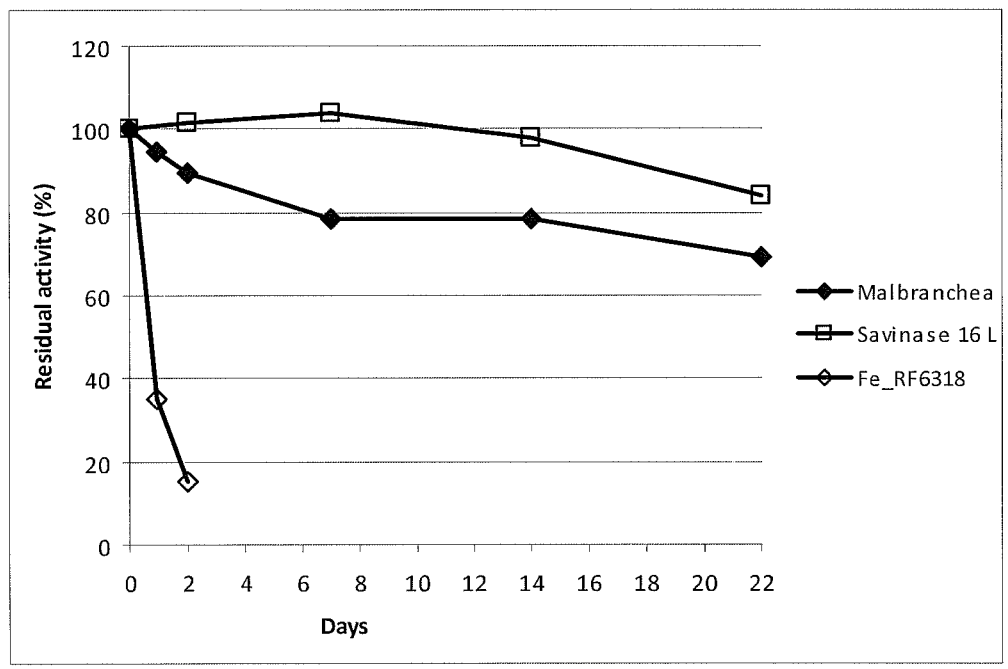
FIG. 12B shows the stability of Malbranchea ALKO4122 protease in Commercial liquid detergent at 37° C. (pH approx. 8). Commercial preparation Savinase® Ultra 16L and recombinant protease Fe_RF6318 (WO2010125174A1) were used for comparison. The amount of enzyme preparation used in detergent was 4% (w/w).

In addition to washing, the enzyme of the present invention sufficiently retains its activity also during storage, even when stored in liquid detergents, as shown in Examples 9 and 10. *Malbranchea* ALKO4122 protease has excellent storage stability at 37° C. compared to e.g. *Fusarium* protease Fe_RF6318 (WO2010125174A1) (FIGS. 11A and B). FIGS. 12A and 12B show that *Malbranchea* protease has especially good stability in Ecolabel Reference Detergent, light duty (wfk Testgewebe GmbH) and Commercial liquid detergent (Table 3) compared to *Fusarium* protease and similar stability in Ecolabel compared to commercial bacterial protease Savinase® 16L. Good stability of the protease according to the invention at elevated temperatures makes it especially suitable for liquid detergent formulations in warm climate countries.

According to a preferred embodiment of the invention the fungal serine protease of the invention is useful in detergent liquids and detergent powders as shown in Examples 6 to 10. The enzyme of enzyme preparation of the invention may be formulated for use in a hand or machine laundry or may be formulated for use in household hard surface cleaning or preferably in hand or machine dishwashing operations.

As a conclusion it can be seen that a new thermostable fungal serine protease enzyme is provided, originating from a thermophilic micro-organism, and which acts particularly well at low temperatures and is compatible and stable in liquid detergent compositions, whereby less stabilizing and other additives are needed.

The invention is illustrated with the following examples relating to some embodiments of the invention, however, the invention is not meant to be limited to these examples only.

EXAMPLES

Example 1

Synthesis of Probes for Cloning Protease Genes from *Malbranchea* and Cloning of Protease Gene from *Malbranchea* ALKO4122 and ALKO4178 Strains (a) Isolation of DNA and Molecular Biology Methods Used Standard molecular biology methods were used in the isolation and enzyme treatments of DNA (e.g. isolation of plasmid DNA, digestion of DNA to produce DNA fragments), in *E. coli* transformations, sequencing etc. The basic methods used were either as described by the enzyme, reagent or kit manufacturer or as described in the standard molecular biology handbooks, e.g. Sambrook and Russell (2001). Isolation of genomic DNA from filamentous fungi was done as described in detail by Raeder and Broda (1985).

(b) Primers for Probe Preparation

The probes for cloning the genes encoding *Malbranchea* proteases were synthesised by PCR. Degenerate sense and antisense oligos were planned basing on the consensus amino acid sequences of fungal proteases (e.g. *Fusarium equiseti* RF6318, *Fusarium* acuminatum RF7182, *T. reesei* Prb1 in WO2010125174, WO2010125175 and WO2011003968, AB Enzymes Oy, respectively). An additional 5'-primer (DET5) was synthesised according to a region chosen from the published N-terminal sequence of *Malbranchea cinnamomea* Thermomycolin (altogether 34 amino acids; Swiss-Prot accession number P13858.1). Amino acids 20-28 of the above sequence were used for designing DET5. The sequences of the primers and the peptide sequences used for their design are shown in the following Table 1 (SEQ ID NOs: 1-5 and SEQ ID NOs: 6-10, respectively). The oligo's name, SEQ ID NO, length, degeneracy and nucleotide sequence are included in the table as well as the peptide sequences used in planning of the primers and their SEQ ID NOs: 6-10.

TABLE 1

Oligonucleotides (SEQ ID NOs: 1-5) used as PCR primers in probe amplification.

| Oligo | SEQ ID NO: | Length (nts) | Degeneracy | Sequence[a] | Peptide | SEQ ID NO: |
|---|---|---|---|---|---|---|
| DET1 | 1 | 17 | 256 | GGNCAYGGNACNCAYGT (s) | GHGTHV | 6 |
| DET2 | 2 | 20 | 128 | AAYTGGGCNGTNAAYGAYAT (s) | NWAVNDI | 7 |
| DET3 | 3 | 20 | 3072 | NCCRTARTTNGTRAANSWNG (as) | ASFTNYG | 8 |
| DET4 | 4 | 20 | 6912 | NGCCATNSWNGTNCCNSWDA (as) | ISGTSMA | 9 |
| DET5 | 5 | 26 | 6144 | CARGCNGGNATHMGNGAYTAYCAYTA (s) | QAGIRDYHY | 10 |

[a]N = A, T, C or G; R = A or G; Y = T or C, H = A, C or T, M = A or C; "s" and "as" in parenthesis after the nucleotide sequence = sense strand and antisense strand, respectively.

(c) PCR Reactions and Selection of Probes for Cloning the Full-length Protease Genes Genomic DNA preparations isolated from *Malbranchea* ALKO4122 and ALKO4178 were used as templates in the PCR reactions. *Malbranchea* ALKO4122 has been identified by CBS identification service (Utrecht, The Netherlands) as *Malbranchea cinnamomea* (Lib.) Oorschot de Hoog (Synonym of *Malbranchea pulchella* var. *sulfurea* (Miehe) Cooney & R. Emers.) at January, 2011. *Malbranchea* ALKO4178 is deposited to Roal Oy culture collection as *Malbranchea sulfurea* but no further identification of this isolate has been done by CBS or other institute specialised in identification of filamentous fungi.

For isolation of the genomic DNAs, *Malbranchea* ALKO4122 and ALKO4178 mycelia were grown by cultivating the strains at 37° C. for 4 days at 250 rpm in 50 ml of glucose-yeast extract medium (25 g glucose, 27.5 g yeast extract pH 6.5). The mycelia were collected and the genomic DNAs were isolated and used as templates for probe synthesis. The PCR reaction mixtures contained Phusion® GC buffer (Finnzymes/Fisher Scientific, Finland), 0.2 mM dNTPs, 50 µmol each primer, DMSO (1/10 of the volume) and 1 units of Phusion® polymerase (Finnzymes/Fisher Scientific) and approximately 0.5-1 µg of genomic DNA per 50 µl reaction volume. The conditions for the PCR reactions were: 1 min initial denaturation at 98° C., followed by 28 cycles of 10 sec at 98° C., 30 sec annealing at 45, 47, 52 and 57° C., 30 sec extension at 72° C. and a final extension at 72° C. for 5 min. Primer combination DET5 (SEQ ID NO: 5) and DET4 (SEQ ID NO: 4) produced, in the three lowest annealing temperatures (see above), a DNA product having size of about 0.8 kb. This size corresponded to the size expected to be obtained from a protease gene, according to calculations basing on published fungal protease sequences. A product with similar size was obtained when either ALKO4122 or ALKO4178 genomic DNA was used as a template. The DNA products were isolated and purified from the PCR reaction mixtures and ligated to pCR®4 Blunt-TOPO vector according to the manufacturer's instructions (Invitrogen, USA). The resulting plasmids were named as pALK3092 (ALKO4122 PCR product as an insert) and pALK3093 (ALKO4178 PCR product as an insert). The inserts were sequenced from both pALK3092 (SEQ ID NO: 11) and pALK3093 (SEQ ID NO: 12). Both the inserts were found to be 791 by in length and they only showed one nucleotide difference with each other in the synthesized region (disregarding the primer sequences). The nucleotide 323 in the pALK3092 insert was C and in the pALK3093 insert it was T. The *E. coli* strains RF8758 and RF8759 including the plasmids pALK3092 and pALK3093, respectively, were deposited to the DSMZ collection under the accession numbers DSM 24426 and DSM 24427, respectively.

A BLASTP search was done with the sequences obtained using program version 2.2.23 at NCBI (National Center for Biotechnology Information) with default settings (Altschul et al., 1990). The encoded amino acid sequences showed homology e.g. to hypothetical and conserved hypothetical proteins from *Uncinocarpus reesii* (XP_002584481.1 and XP_002583205.1, respectively) and to a putative subtilisin-like protein from *Coccidioides posadasii* (EER24932.1) and hypothetical protein from *Coccidioides immitis* (XP_001239485.1) with identities of 59-65%. Thus, the results indicate that the DNA fragments obtained from the PCR reactions were parts of genes encoding proteases and thus useful as probes for screening the full-length protease gene(s) from *Malbranchea*. The encoded amino acid sequence that was following the sequence encoded by the primer DET5 was, however, not identical with the published *Malbranchea* Thermomycolin sequence (amino acids 29-34, accession number P13858).

(d) Cloning of the Full-length *Malbranchea* ALKO4122 Protease Gene

*Malbranchea* ALKO4122 and ALKO4178 genomic DNAs were digested with several restriction enzymes for Southern blot analysis. The digestions were run on gel and Southern transfer and hybridization were performed. The probe for Southern blots was labelled by PCR using M13 reverse and M13 forward primers and pALK3092 (Example 1c) as a template. The probe sequence includes the SEQ ID NO:11 (Example 1c). The labelling of the probe using PCR DIG (digoxigenin) labeling mix and hybridization were performed according to supplier's instructions (Roche, Germany). Hybridization was performed over night at 68° C. After hybridization the filters were washed as follows: 2×5 min washes at room temperature using 2×SSC-0.1 SDS, followed by 2×15 min washes at 68° C. using 0.1×SSC-0.1% SDS.

Several hybridizing fragments in the *Malbranchea* ALKO4122 and ALKO4178 genomic DNA digests were detected. Most of the digests gave identical results from both the genomes. A hybridising approximately 2.7 kb fragment was obtained from the genomic XbaI digest. The XbaI fragment was analysed to contain the full-length protease gene (by double digesting the genomic DNA with XbaI and PstI included in the probe sequence and by size calculations basing on the published fungal protease sequences). The DNA fragments were isolated from ALKO4122 genomic XbaI digestion from the size range of the hybridizing fragment (approximately 2.7 kb). Isolation was done from an agarose gel. The isolated genomic fragments were cloned to pBluescript II KS+ (Stratagene, USA) vector cleaved with XbaI. Ligation mixture was transformed into *Escherichia coli* XL10-Gold cells (Stratagene) and plated on LB (Luria-Bertani) plates containing 50 µg/ml ampicillin. The positive *E. coli* colonies were screened using colonial hybridization with PCR labeled pALK3092 insert as a probe. Hybridization was performed as described for the genomic DNA digests. Altogether 20 clones were picked from the plates and out of these eight were shown, by XbaI restriction digestion and Southern blot hybridization (done as described for the genomic hybridization), to contain inserts having the expected size and hybridizing with the pALK3092 probe. The XbaI insert (2961 bp) was sequenced and confirmed to contain a full-length *Malbranchea* ALKO4122 protease gene (SEQ ID NO:13). The plasmid containing the above XbaI genomic fragment was named as pALK3094. The *E. coli* strain RF8791 including the plasmid pALK3094 was deposited to the DSMZ collection under the accession number DSM 24410.

(e) Characterisation of the Gene Encoding *Malbranchea* ALKO4122 Protease and the Deduced Amino Acid Sequence of the Protease The gene sequence (SEQ ID NO:13), its partial promoter and terminator sequences and the deduced amino acid sequence of the encoded protease (SEQ ID NO:14) are shown in FIG. 1. The length of the gene is 1436 by (including the stop codon). Three putative introns were found having lengths of 72, 87 and 71 bps. The introns had the consensus 5' and 3' border sequences as well as the internal consensus sequences according to those identified from several fungal introns (Gurr et al., 1987). The deduced protein sequence (SEQ ID NO:14) consists of 401 amino acids, including a predicted signal sequence of 20 amino acids (SignalP V3.0; Nielsen et al., 1997 and Nielsen and Krogh, 1998) and a predicted pro sequence of 100 amino acids. The location of the N-terminus of the mature protease, Ala 121, was estimated according to comparisons made with other fungal protease sequences. The predicted molecular mass of the mature protease was 28 530 Da and the predicted pI was 6.15. These predictions were calculated using the Compute pI/MW tool at ExPASy server (Gasteiger et al., 2003). The deduced mature amino acid sequence contained three possible N-glycosylation sites at amino acid positions Asn134, Asn172 and Asn277 of the mature sequence (amino acid positions 254, 292 and 397 in FIG. 1), but according to CBS Server NetNGlyc V1.0 only the sites at positions Asn 134 and Asn277 are likely.

The N-terminal sequence of the *Malbranchea* ALKO4122 protease corresponded only partly to the previously published *M. cinnamonea* Thermomycolin N-terminal sequence (P13858): only the first 28 amino acids were identical in these two sequences.

There was one nucleotide difference in the *Malbranchea* ALKO4122 protease gene probe sequence in pALK3092 compared to the genomic ALKO4122 protease gene sequence (in the corresponding region). The genomic ALKO4122 protease gene sequence was, however, identical to that of ALKO4178 protease probe sequence in pALK3093 (in the corresponding region). Thus, the one nucleotide difference in pALK3092 insert (Example 1c) most probably resulted from a mutation in the probe PCR reaction.

(f) Cloning of the *Malbranchea* ALKO4178 Protease Gene

Primers DET27 (SEQ ID NO: 19) and DET28 (SEQ ID NO: 20) were designed to synthesise the full-length protease gene from *Malbranchea* ALKO4178 by PCR. DET 27 is a sense primer from the promoter (from nucleotide −44 to −24 from ATG) and DET28 is an antisense primer from the terminator (from nucleotide 55 to 36 from the stop codon) of the *Malbranchea* ALKO4122 protease gene (FIG. 1). The PCR reaction mixtures contained 1× Phusion® HF buffer (Finnzymes/Fisher Scientific, Finland), 0.2 mM dNTPs, 75 µmol each primer and 2 units of Phusion® polymerase (Finnzymes/Fisher Scientific) and approximately 1.5 µg of genomic DNA per 200 µl reaction volume. The conditions for the PCR reactions were: 30 sec initial denaturation at 98° C., followed by 24 cycles of 10 sec at 98° C., 30 sec annealing at 60 and 65° C., 60 sec extension at 72° C. and a final extension at 72° C. for 7 min. Fragments of expected length (~1.5 kb) were obtained from the reactions. Fragments from two separate PCR reactions were isolated and ligated into pCR4® Blunt-TOPO® vectors. The inserts were sequenced from the separate clones. Sequences of the inserts in both clones were identical with each other and with the *Malbranchea* ALKO4122 protease gene, its partial promoter and terminator (FIG. 1). The plasmid containing the *Malbranchea* ALKO4178 protease gene (the PCR fragment obtained) was named as pALK3147. The *E. coli* clone including this plasmid was stored to Roal Oy culture collection as RF9332.

(g) Homology, Identity and Alignment Studies

The mature *Malbranchea* ALKO4122 protease amino acid sequence (SEQ ID NO:18) was used to search homologous protease sequences from public sources. Both the redundant protein sequences and protein sequences in the Patent division of GenBank were searched. The BLASTP program version 2.2.25 at NCBI (National Center for Biotechnology Information) with default settings was used in the search (Altschul et al., 1990). The highest identities obtained from all redundant sequences were 65% for *Coccidioides posadasii* putative subtilisin-like protease (EER24932.1) and *Coccidioides immitis* hypothetical protein CIMG_09197 (XP_001239485.1), 65% for *Uncinocarpus reesii* hypothetical protein UREG_05170 (EEP80328.1), 64% for *Coccidioides immitis* hypothetical protein CIMB_01394 (XP_001247623.1), *Coccidioides posadasii* putative subtilisin-like protease (EER23662.1), *Uncinocarpus reesii* hypothetical protein (EEP81307.1) and *Arthroderma otae* alkaline proteinase (EEQ28657.1). The EER24932.1 and XP_001239485.1 only differ from each other by three amino acids and XP_001247623.1 and EER23662.1 from each other only by one amino acid. The *Malbranchea* ALKO4122 protease sequence was aligned with the above homologous sequences using ClustalW2 alignment. The putative mature sequences from each protease were used in the alignment. The mature sequences from each protease were compared with each other. The identity values (score %) obtained by using ClustalW2 alignment (www.ebi.ac.uk/Tools/msa/clustalw2/) are shown in Table 2. The mature amino acid sequences excluding the signal peptides and propeptides were aligned using default settings (Protein Weight Matrix: Gonnet, Gap open: 10, Gap extension: 0.20, Gap distances 5). SEQ ID NO:18 is the mature amino acid sequence of ALKO4122 protease. The identity values (score %) obtained were from 63%-65%.

The highest identities for the sequences in patent division were 55% for SEQ ID NO:2 in U.S. Pat. No. 5,962,765 (AAE30270.1; protease from *Metarhizium anisopliae*) and SEQ ID:15 in WO 8807581 (AAA54276.1; protease from *Tritirachium album*).

TABLE 2

The identity values (score %) obtained from ClustalW 2.1 multiple sequence alignment of the deduced protease amino acid sequences.

| Sequence | 1 | 2 | 3 | 4 | 5 | 6 | 7 | 8 |
|---|---|---|---|---|---|---|---|---|
| 1 = SEQ ID NO: 18 | 100 | | | | | | | |
| 2 = EER24932.1 | 65 | 100 | | | | | | |
| 3 = XP_001239485.1 | 65 | 99 | 100 | | | | | |
| 4 = EEP80328.1 | 64 | 73 | 72 | 100 | | | | |
| 5 = XP_001247623.1 | 63 | 59 | 59 | 60 | 100 | | | |
| 6 = EER23662.1 | 63 | 59 | 59 | 61 | 99 | 100 | | |
| 7 = EEP81307.1 | 63 | 59 | 59 | 63 | 62 | 61 | 100 | |
| 8 = EEQ28657.1 | 64 | 58 | 58 | 58 | 57 | 57 | 62 | 100 |

Example 2

Production of the Recombinant *Malbranchea* ALKO4122 Protease in *Trichoderma reesei*

(a) Preparing the Production Vector and Production Strains

The expression plasmid pALK3097 was constructed for production of recombinant *Malbranchea* ALKO4122 protease in *Trichoderma reesei*. The gene with its own signal sequence was exactly fused to the *T. reesei* cbh1 (cel7A) promoter by PCR. The primers used in the PCR reaction were named as DET17 (5'-primer; SEQ ID NO:21) and DET18 (3'-primer; SEQ ID NO:22). The DET17 primer contains a partial cbh1 promoter from SacII site (position −16 from ATG) to position −1 and the beginning of the *Malbranchea* protease gene (26 nucleotides including the ATG start codon) and 3 extra nucleotides at the 5' end. The DET18 contains 26 nucleotides from the end of the *Malbranchea* protease gene (including the STOP codon) and a linker including a BamHI site for fusing the gene from its 3'-end to pALK2777 linker (cbh1 terminator; see below). The protease gene's native terminator is not included in the construction.

The protease gene was excised from the PCR fragment by SacII-BamHI digestion and fused to pALK2777 expression vector backbone cleaved with the same enzymes (FIG. 2). The pALK2777 plasmid contains the cbh1 promoter (to SacII site), linker including e.g. the BamHI site, cbh1 terminator and a synthetic amdS gene for screening the transformants. The synthetic amdS gene in pALK2777 contains a shortened terminator (to XbaI site) compared to the native amdS gene (Kelly and Hynes, 1985). Also, the introns of the native amdS gene have been removed and chosen restriction sites from the amdS promoter and gene have been modified to ease the construction and isolation of the expression cassettes. However, the amino acid sequence encoded by the synthetic amdS gene is identical to that encoded by the wild type amdS gene.

Figure 3:
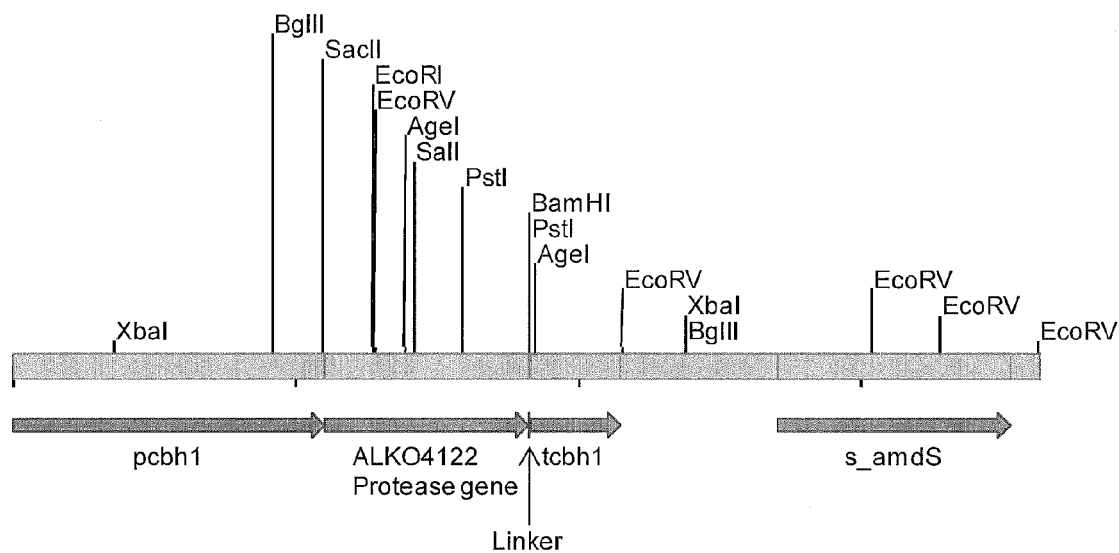
FIG. 3 schematically shows the pALK3097 cassette isolated from the vector backbone by NoI digestion and used for expressing the *Malbranchea* ALKO4122 protease gene in *Trichoderma reesei*. pcbh1, cbh1 promoter; tcbh1, cbh1 terminator; s_amdS, synthetic amdS marker gene (cDNA); Linker, linker sequence.

The 7.2 kb linear expression cassette (presented in FIG. 3) was isolated from the vector backbone after NotI digestion and was used for transforming *Trichoderma reesei* protoplasts. The *T. reesei* host strain used does not produce any of the four major *T. reesei* cellulases (CBHI, CBHII, EGI, EGII). The transformations were performed as in Penttilä et al. (1987) with the modifications described in Karhunen et al. (1993). The transformants were purified on selection plates through single conidia prior to sporulating them on PD.

(b) Protease Production in Shake Flasks and Laboratory Scale Bioreactor

The transformants were inoculated from the PD slants to shake flasks containing 50 ml of complex lactose-based cellulase inducing medium (Joutsjoki et al., 1993) buffered with 5% $KH_2PO_4$ and pH 6.0. The protease production of the transformants was analyzed from the culture supernatants after growing the transformants for 5 days at 30° C., 250 rpm. In SDS-PAGE gels, a major protein band of about 30 kDa corresponding to the expected mass of recombinant protease was detected from the spent culture supernatants. The protease activity was assayed from the samples using casein as a substrate as described in Example 3. Clearly increased activities compared to host were measured from the culture supernatants. The integration of the expression cassette into the fungal genomes was confirmed from chosen transformants by using Southern blot analysis in which several genomic digests were used and the expression cassette pALK3097 was used as a probe.

The *T. reesei* transformants producing the best protease activities in the shake flask cultivations were chosen to be cultivated in laboratory scale bioreactors. Cellulase inducing complex medium was used in the cultivations. The spent culture medium obtained from the cultivations or concentrated samples were used as starting materials for purification and further biochemical characterization of the recombinant *Malbranchea* ALKO4122 protease (Examples 3-5) as well as for the application tests presented in Examples 6-10.

Example 3

Protease Activity Assay

Protease activity was measured using casein as substrate. Rate of casein degradation by a protease was measured by monitoring the release of acid-soluble peptide fragments as a function of time. Acid-soluble peptides were quantified spectrophotometrically. The result was expressed as 1 µg of tyrosine per min per ml (or g).

First all reagent solutions needed in the assay were prepared in deionized water, Milli-Q or equivalent as follows.
(STW) Synthetic Tap Water:
   The following stock solutions were prepared:
   (A) 5.8 g $CaCl_2 \times 2\ H_2O$/200 ml $H_2O$
   (B) 2.8 g $MgCl_2 \times 6\ H_2O$/200 ml $H_2O$
   (C) 4.2 g $NaHCO_3$/200 ml $H_2O$
   10 ml of these solutions were added in the given order to 300 ml of $H_2O$ with stirring, then made up to 1 liter with $H_2O$. The resulting solution was called as synthetic tap water.
Tris Solution, 0.3 M in Synthetic Tap Water:
   36.3 g of Trizma base (SIGMA T-1503) was dissolved in synthetic tap water and made up to 1 liter.
Casein Solution:
   6 g of casein (Hammarsten Usb. 12840) was added to 350 ml synthetic tap water and dissolved with magnetic stirring for 10 min. 50 ml of Tris solution was added and the solution was stirred for another 10 min. Then, the solution was heated up to 70° C. After that the temperature was let to decrease to 50° C. and the pH was adjusted to 8.5 with 0.1M NaOH.

Stirring was continued until room temperature was reached. The solution was made up to 500 ml with synthetic tap water. The substrate solution was stored for maximum of 3 days in refrigerator (or stored as frozen).

110 mM Trichloroacetic Acid Reagent (Reaction Stop Solution):

18 g of TCA (Merck 807) was dissolved in $H_2O$ and made up to 1 liter.

0.5 M $Na_2CO$:

53 g of $Na_2CO_3$ was dissolved in $H_2O$ and made up to 1 liter.

Folin Solution:

25 ml of 2N Folin-Ciocalteu's phenol reagent (SIGMA, F 9252) was diluted up to 100 ml with $H_2O$.

Sample Dilution Buffer:

The sample was diluted in 50 mM Tris-HCl buffer pH 8.5.

The most suitable dilution will yield an absorbance of 0.4-0.8 in the reaction.

Assay:

The assay was started by temperating 2.5 ml of substrate solution in test tubes for 5 min at 50° C. After that 0.5 ml of diluted enzyme solution was added, mixed with vortex mixer and the reaction was conducted at 50° C. for exactly 30 min. The enzyme blank was prepared like the sample but the reaction stop solution (110 mM TCA) was added in test tube before the sample. After the reaction 2.5 ml of stop solution was added in tubes (not for blank), the contents were mixed and allowed to stand for 30 minutes at room temperature. Tubes were centrifuged 4000 rpm for 10 minutes (Hettich Rotanta 460). One ml of clear supernatant was mixed with 2.5 ml 0.5 M $Na_2CO_3$ and 0.5 ml diluted Folin reagent. After waiting for 10 mM (color development) the absorbance of the mixture (color) was measured at 660 nm against an enzyme blank.

At least two parallel samples were used in each measurement.

Example 4

Purification of the Recombinant Protease

Cells and solids were removed from the spent culture medium obtained from the fermentation (Example 2) by centrifugation for 30 min, 50000 g at +4° C. (Sorvall RC6 plus). 8 ml of the supernatant was used for purification of protease. All purification steps were performed at cold room. After centrifugation, sample was filtered through 0.44 filter (MILLEX HV Millipore) before applying to HiPrep 26/10 Desalting column (from GE Healthcare) equilibrated in 20 mM MES pH 5.3. Gel filtered sample was applied to a 1 mL S Sepharose HP column (from GE Healthcare) equilibrated in 20 mM MES pH 5.3.

Proteins were eluted using increasing NaCl gradient (0.5 M). Protease contains fractions were pooled and concentrated using Amicon Ultra-4 10,000 CO Centrifugal filter devices MILLIPORE. Sample was further purified using Superdex 75 gel filtration column equilibrated with 20 mM MES, 150 mM NaCl pH 5.3. Protease contains fractions were combined and used for characterization of pH and temperature profiles. Final sample was analysed on SDS PAGE gel FIG. 4.

Example 5

Characterisation of the Recombinant Protease

Temperature Profile

Figure 5A:
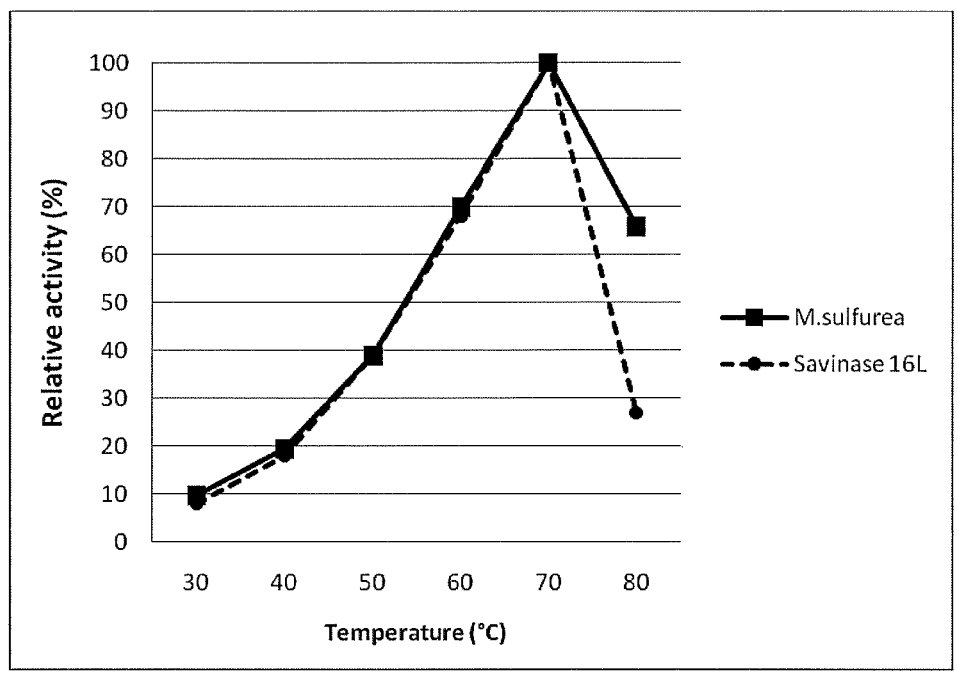
FIG. 5A describes the temperature profile of the recombinant *Malbranchea* protease and Savinase® 16L assayed at pH 8.5 using 30 min reaction time and casein as a substrate. The data points are averages of three separate measurements.

Temperature profile was obtained for the recombinant *Malbranchea* protease and Savinase® 16L by using the assay described in Example 3. The result is shown in FIG. 5A. The protease has a temperature optimum around 70° C.

pH-profile

Figure 5B:
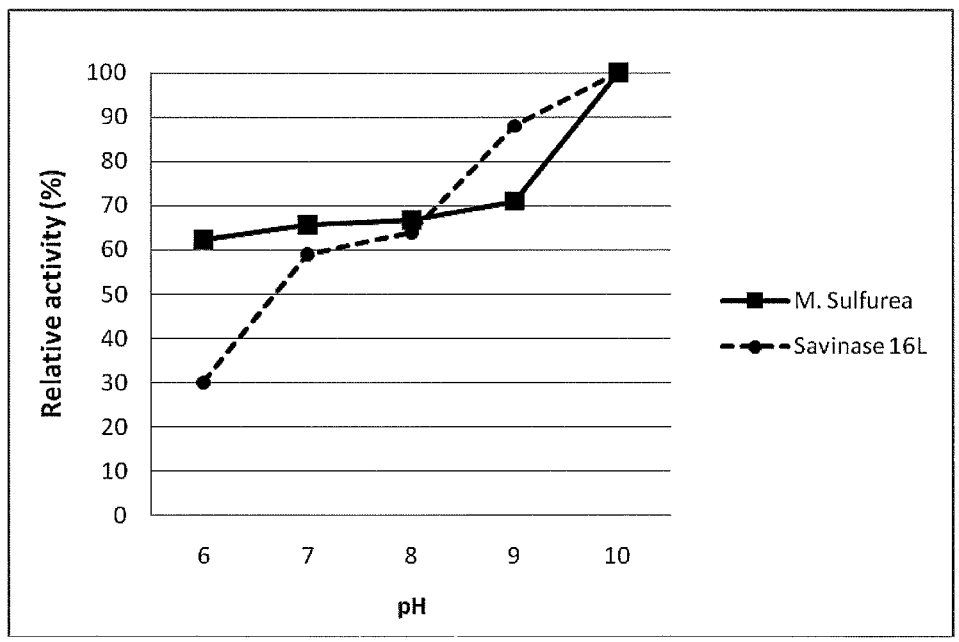
FIG. 5B describes the effect of pH on the activity of recombinant Malbrachea protease and Savinase® 16L. The buffer used was 40 mM Britton-Robinson buffer, casein was used as a substrate, reaction time was 30 min and reaction temperature was 50° C. The data points are averages of three separate measurements FIGS. 6 (6A, 6B, 6C and 6D) describes the stain removal performance of recombinant Malbranchea ALKO4122 protease with blood/milk/ink stain (Art. 117, CO+PES, Serial No. 11-08, new batch, EMPA) at 10-50° C., approx. pH 8, 60 min in the presence of Commercial liquid detergent with concentration of 5 g/l. Commercial protease preparations Savinase® 16L and Savinase® Ultra 16L were used for comparison.
Figure 6A:
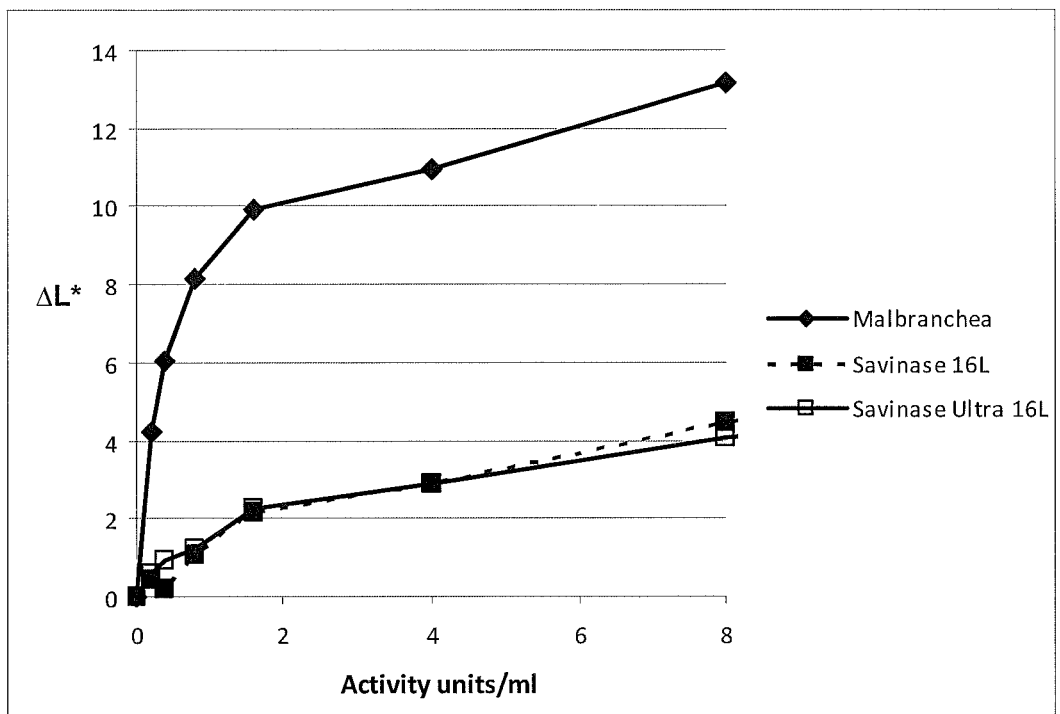
FIG. 6A describes the stain removal performance at 10° C.
Figure 6B:
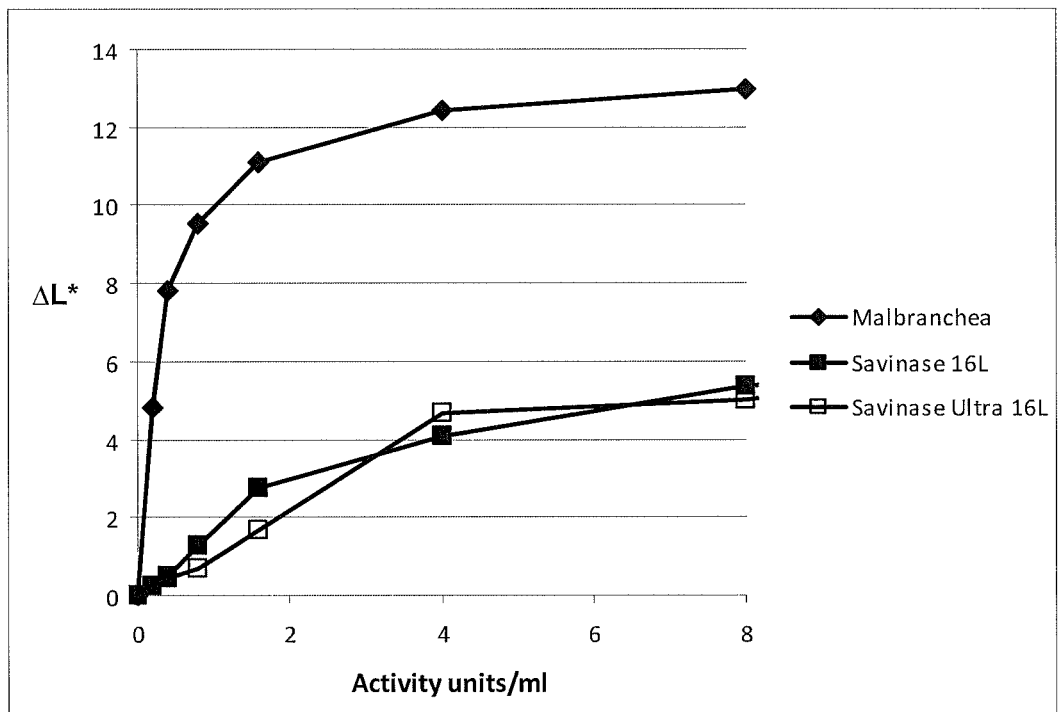
FIG. 6B describes the stain removal performance at 20° C.
Figure 6C:
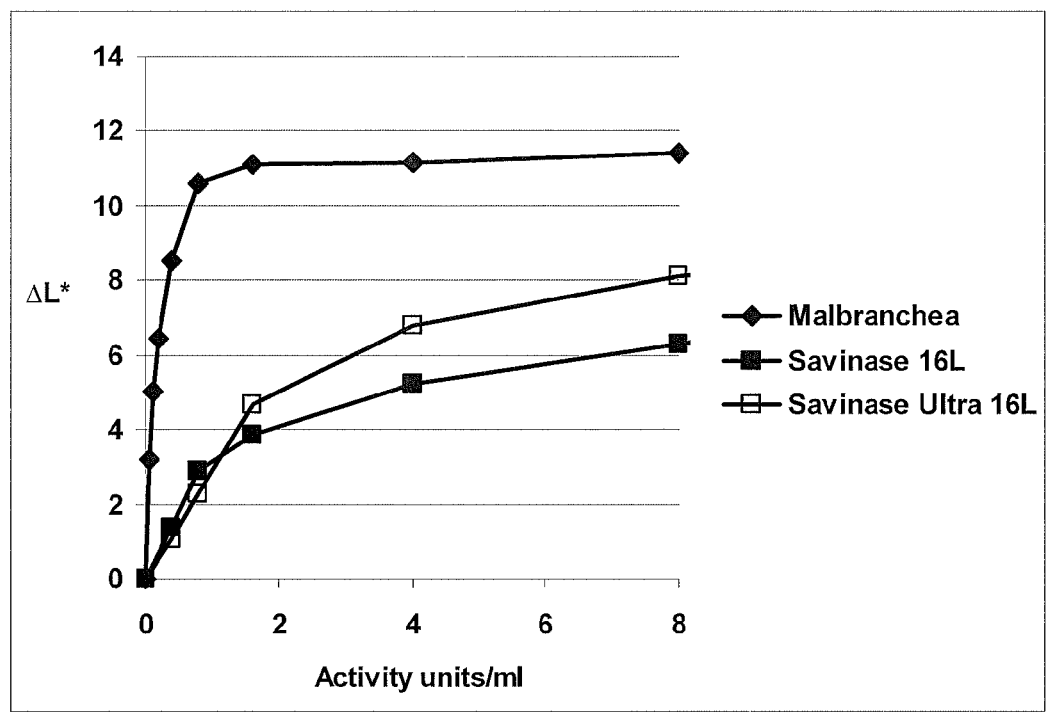
FIG. 6C describes the stain removal performance at 30° C.
Figure 6D:
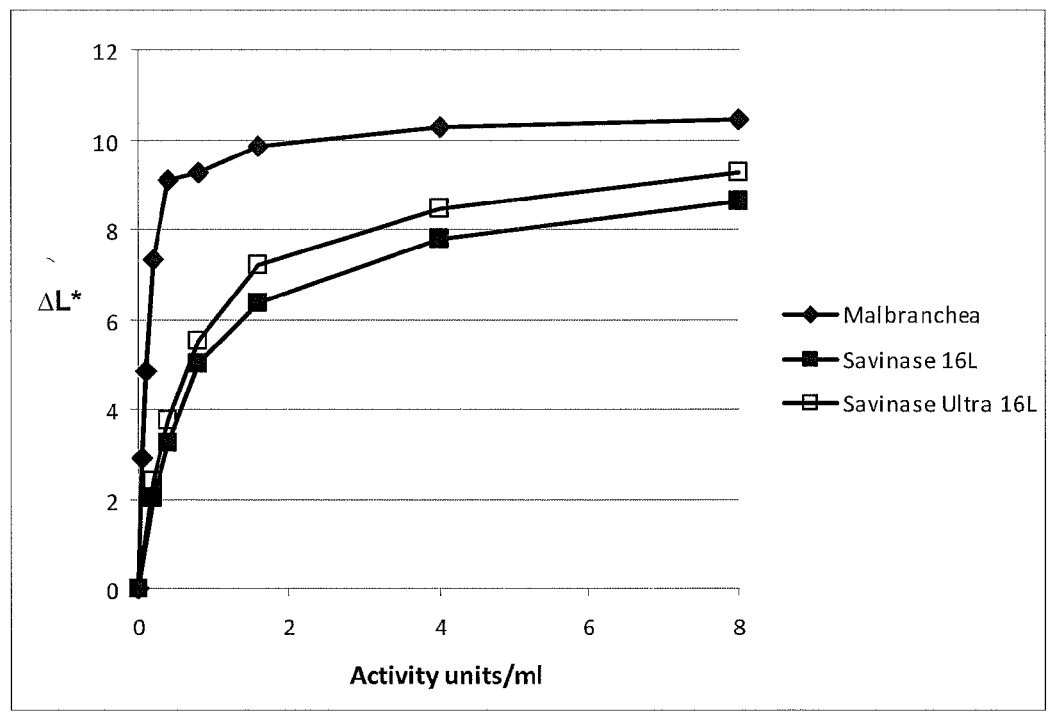
FIG. 6D describes the stain removal performance at 50° C.
Figure 7A:
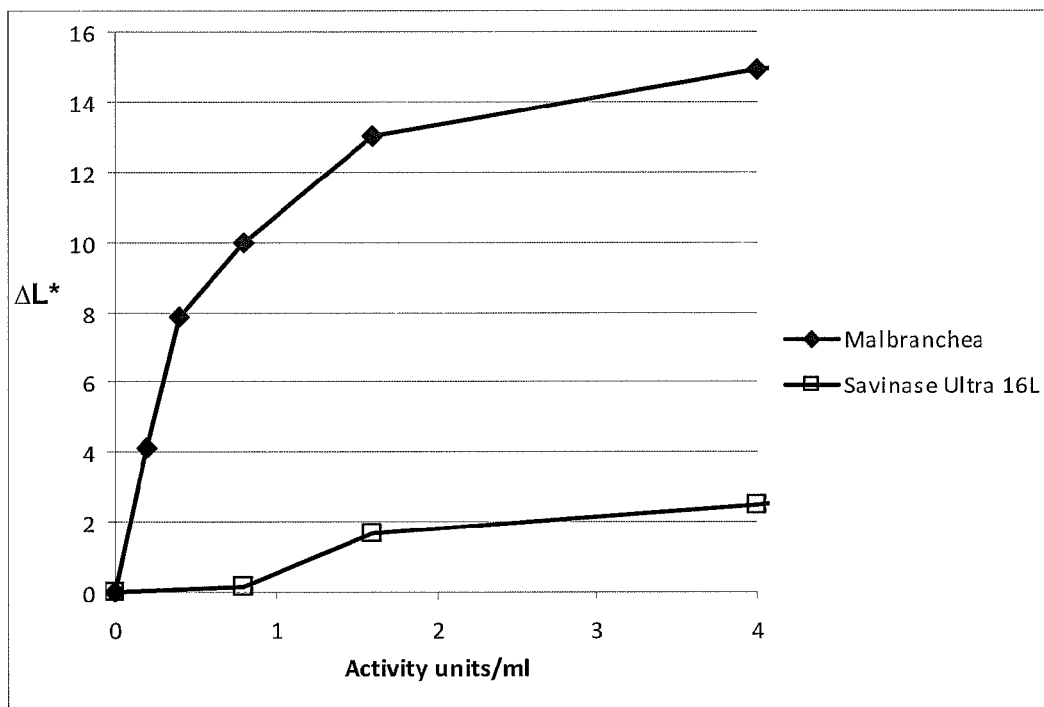
FIG. 7A describes the stain removal performance at 10° C.
Figure 7B:
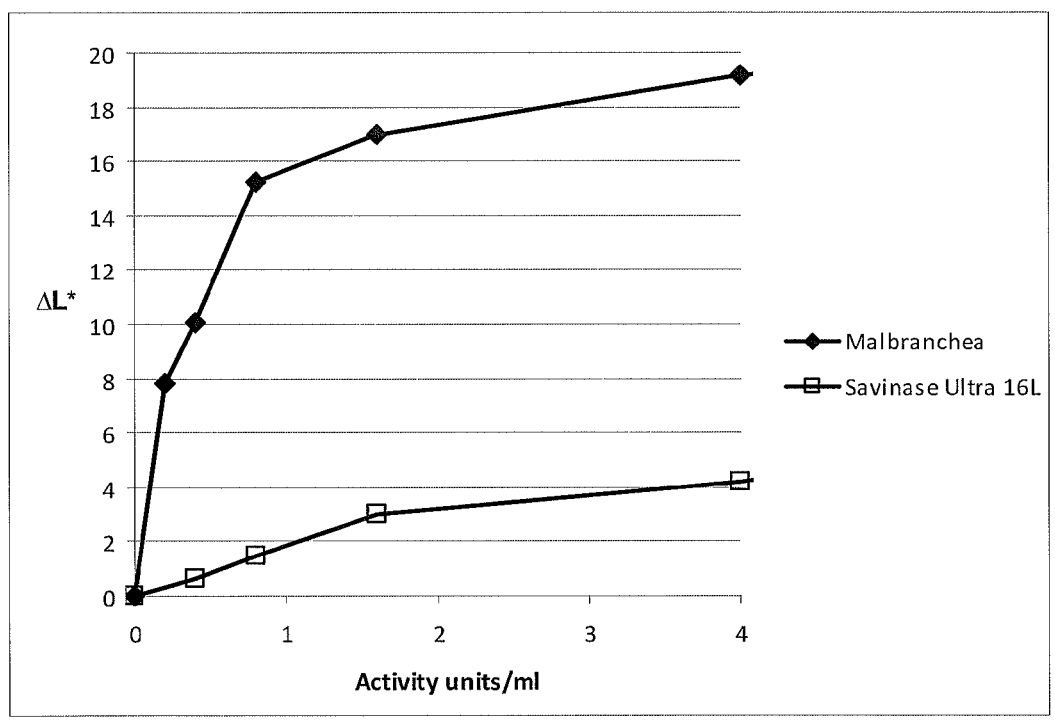
FIG. 7B describes the stain removal performance at 20° C.
Figure 7C:
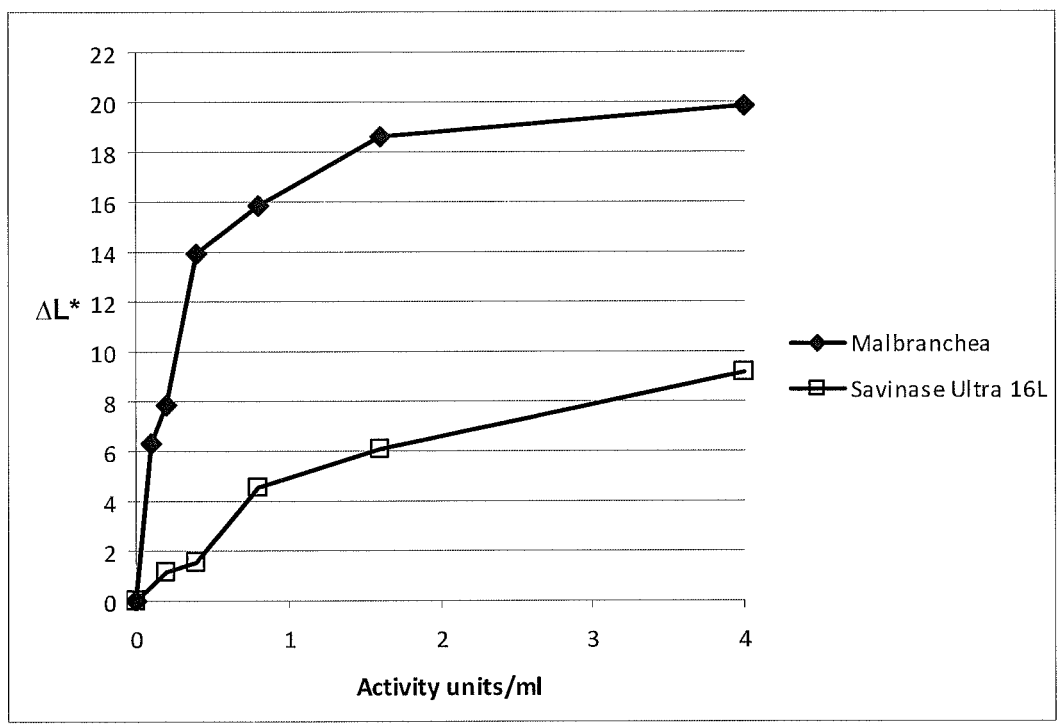
FIG. 7C describes the stain removal performance at 30° C.
Figure 7D:
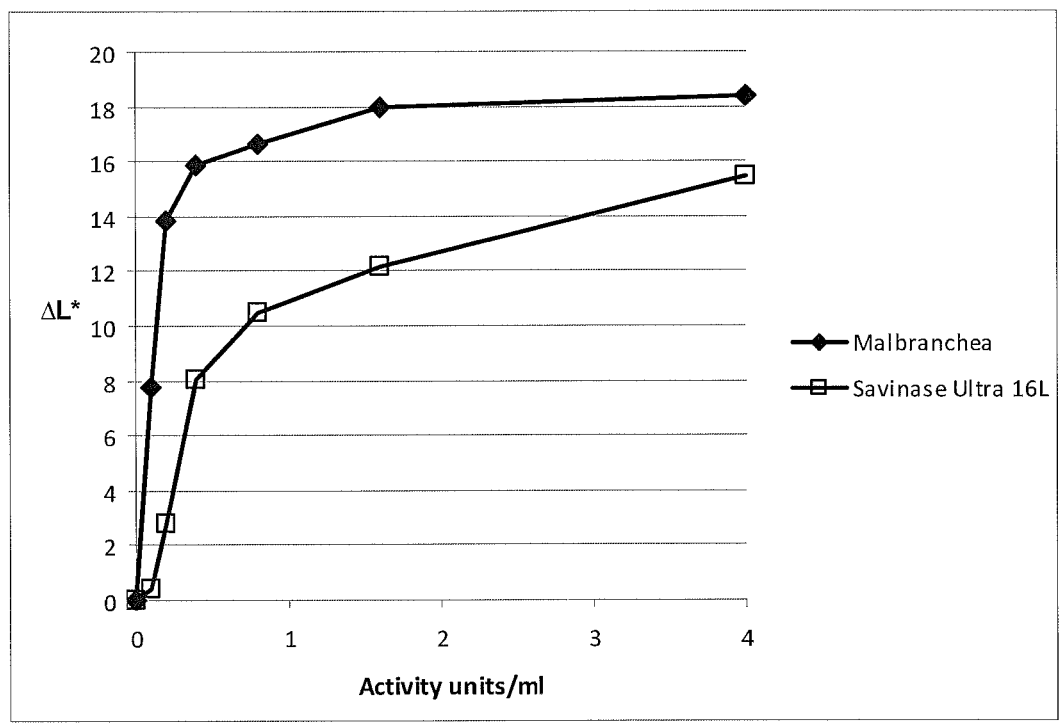
FIG. 7D describes the stain removal performance at 50° C.
Figure 8A:
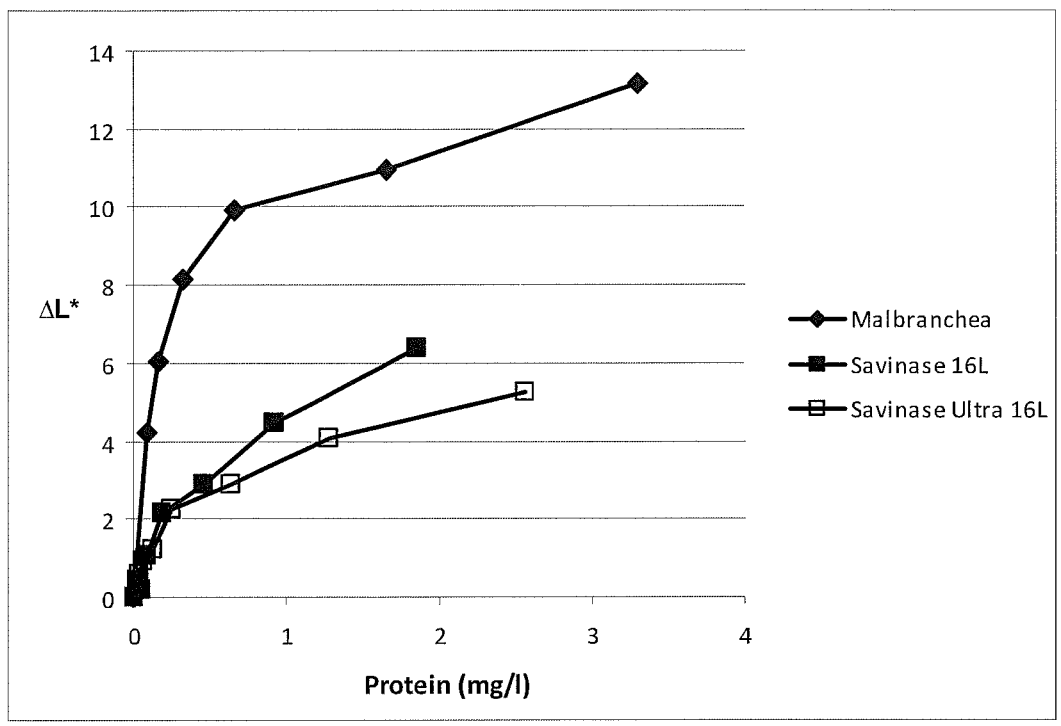
FIG. 8A describes the stain removal performance at 10° C. (enzyme dosage calculated as protein).
Figure 8B:
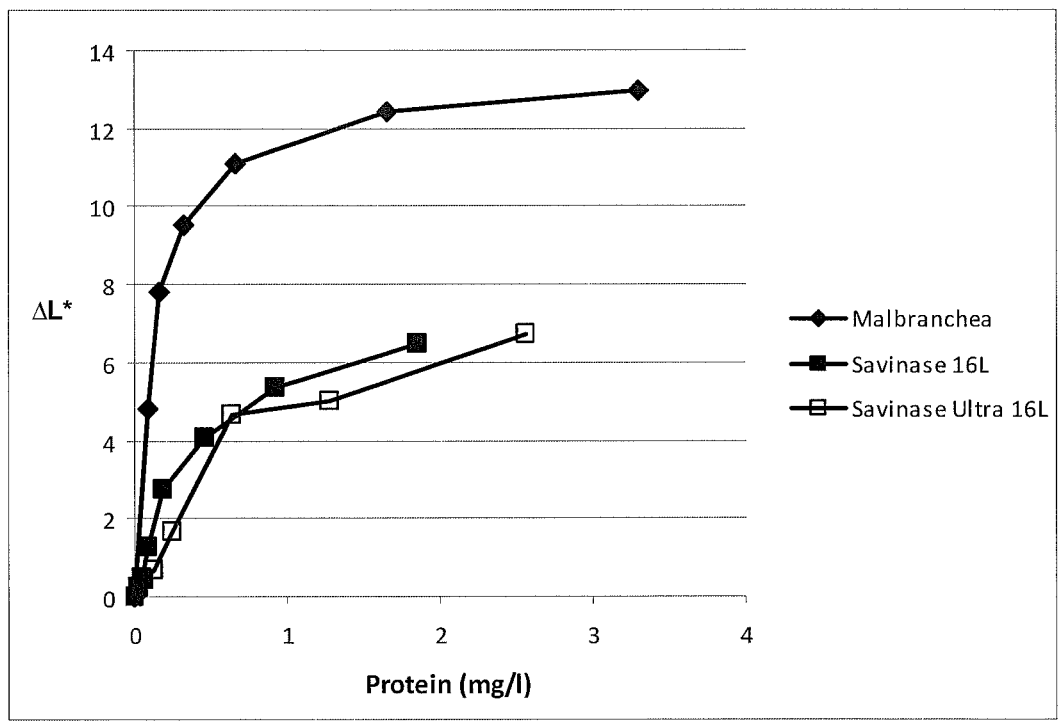
FIG. 8B describes the stain removal performance at 20° C. (enzyme dosage calculated as protein).
Figure 8C:
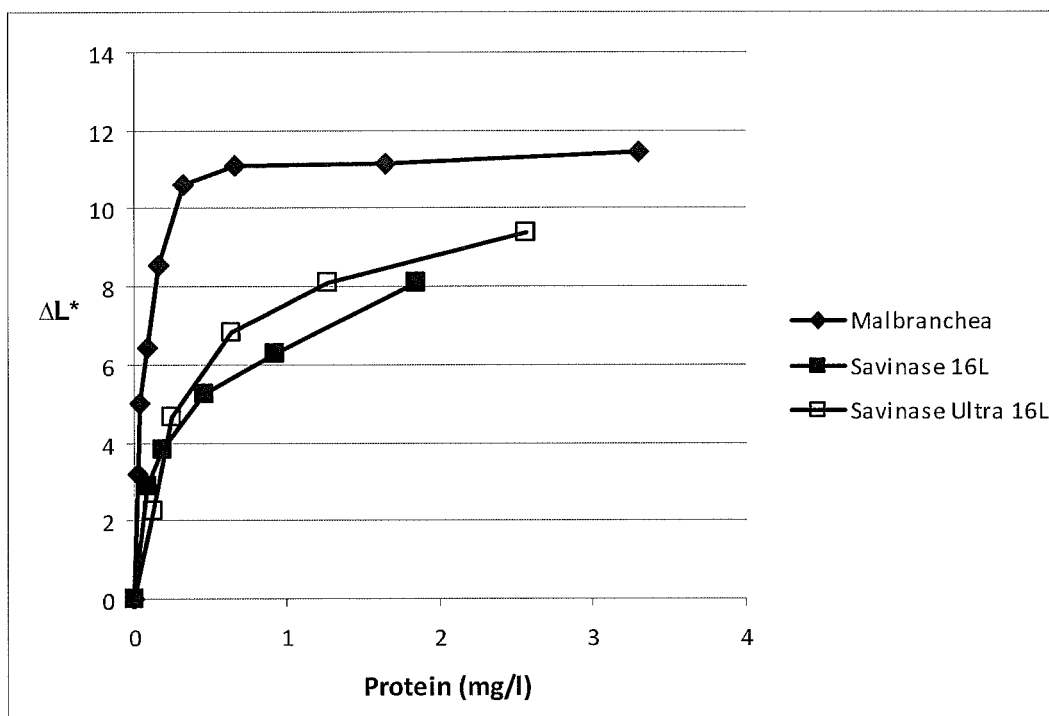
FIG. 8C describes the stain removal performance at 30° C. (enzyme dosage calculated as protein).
Figure 8D:
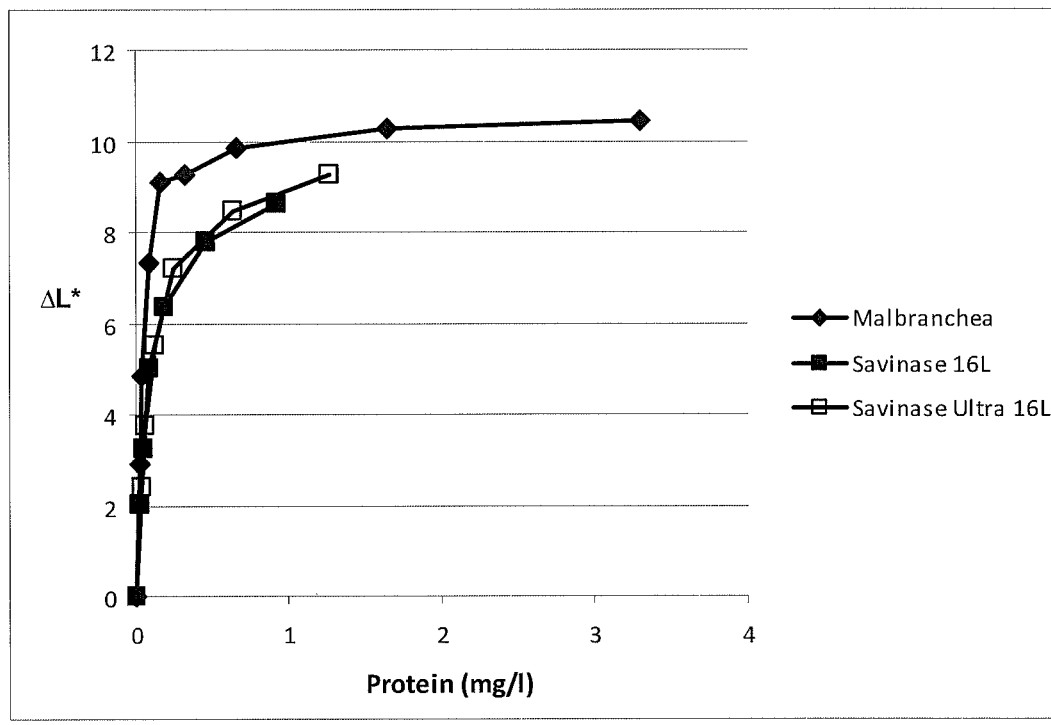
FIG. 8D describes the stain removal performance at 50° C. (enzyme dosage calculated as protein).
Figure 9A:
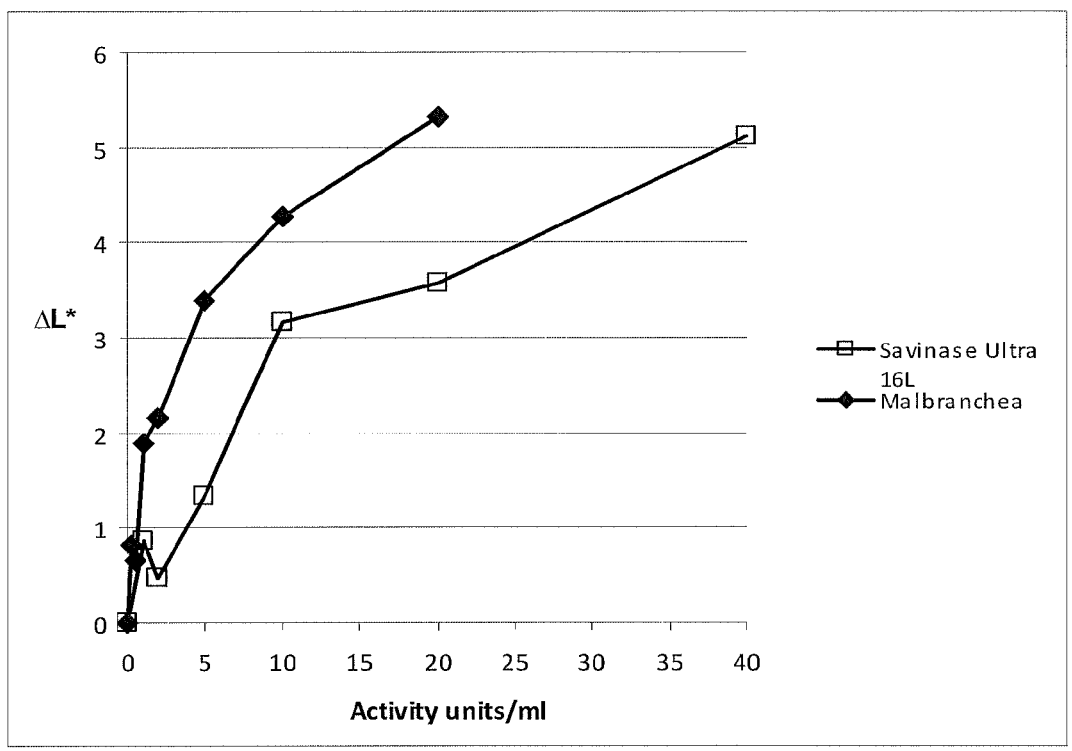
FIG. 9A shows performance on Grass, Cotton, Art. 164 (Serial No. 23-03), EMPA at 30° C.
Figure 9B:
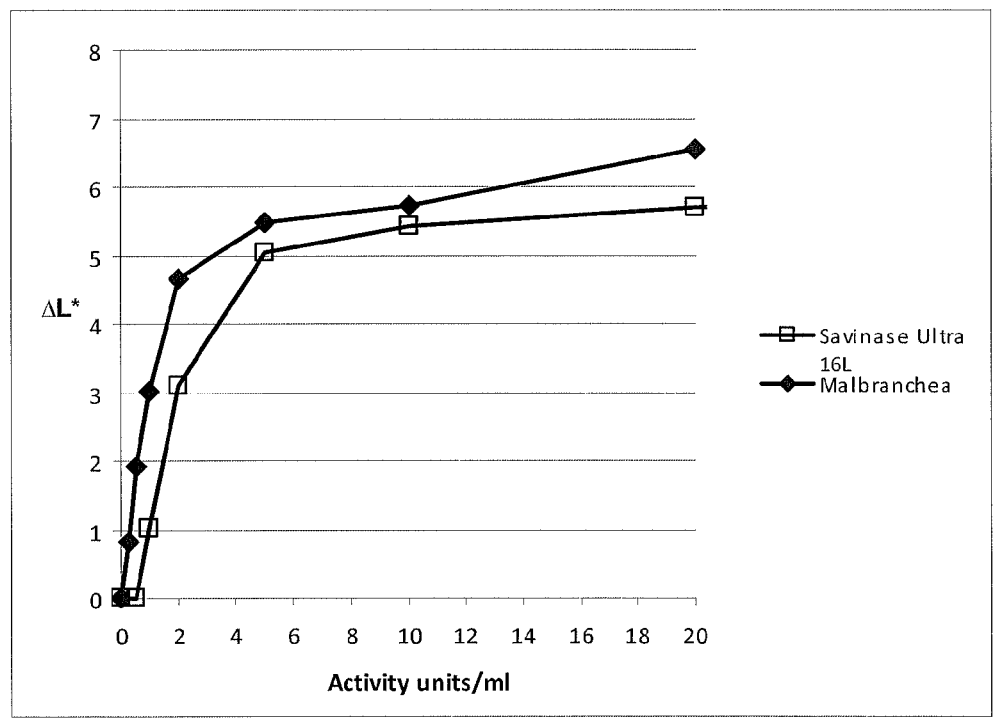
FIG. 9B shows performance on Grass, Cotton, Art. 164 (Serial No. 23-03), EMPA at 60° C.
Figure 9C:
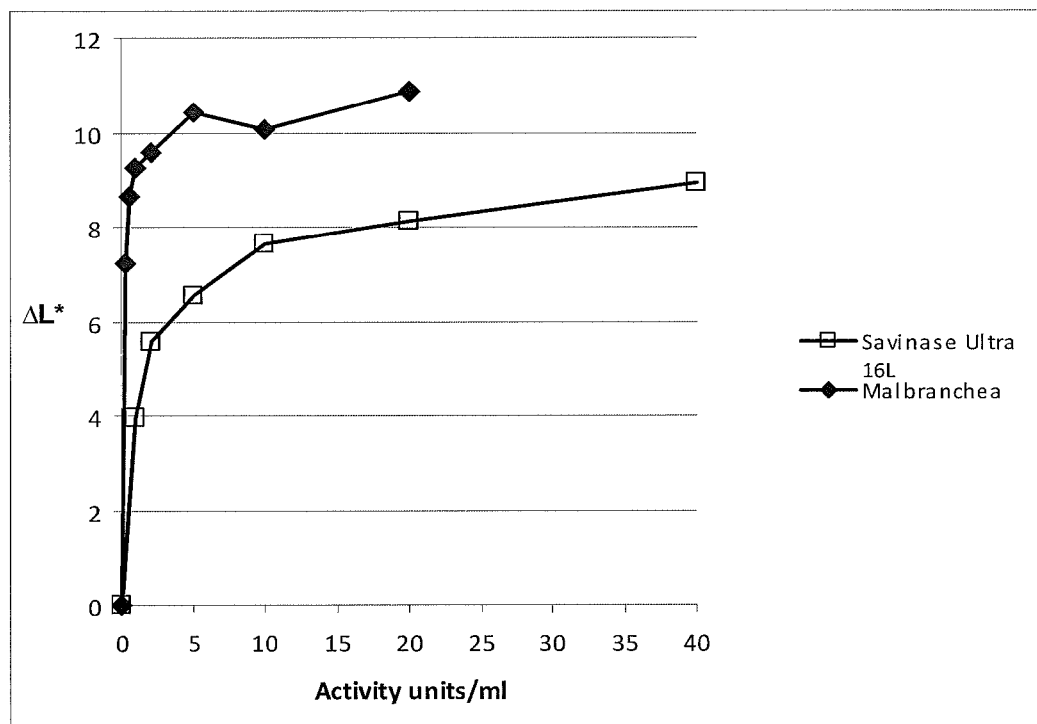
FIG. 9C shows performance on Blood/milk/ink, Cotton, Art. 116 (Serial No. 18-16), EMPA at 30° C.
Figure 9D:
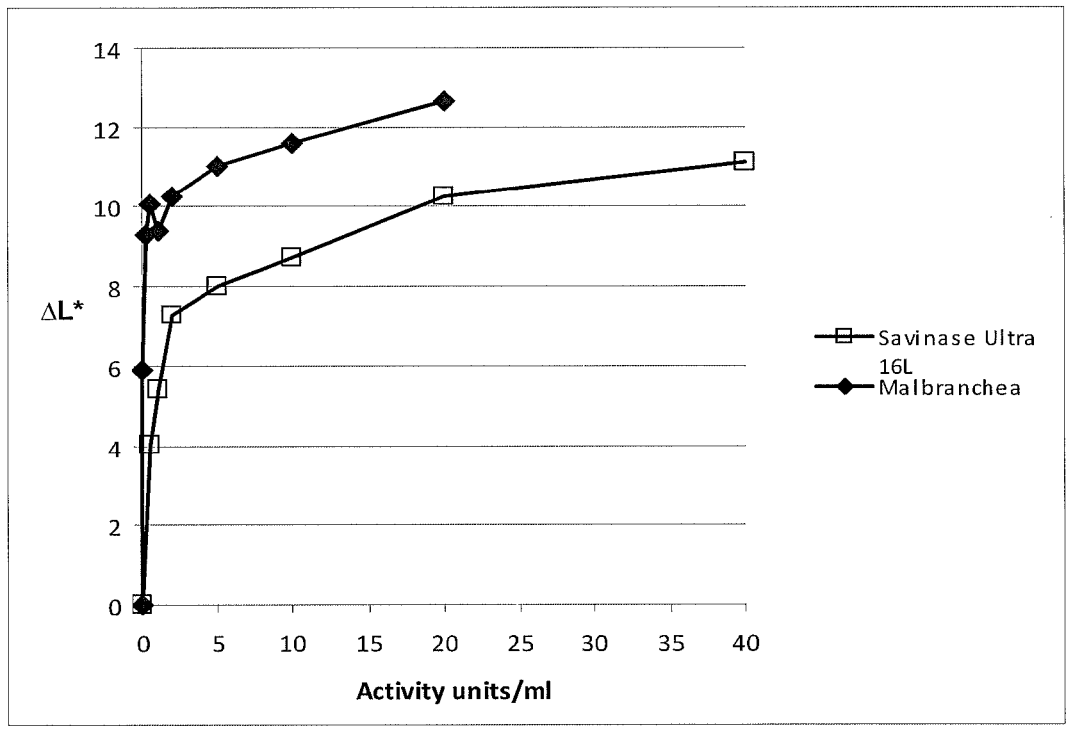
FIG. 9D shows performance on Blood/milk/ink, Cotton, Art. 116 (Serial No. 18-16), EMPA at 60° C.
Figure 9E:
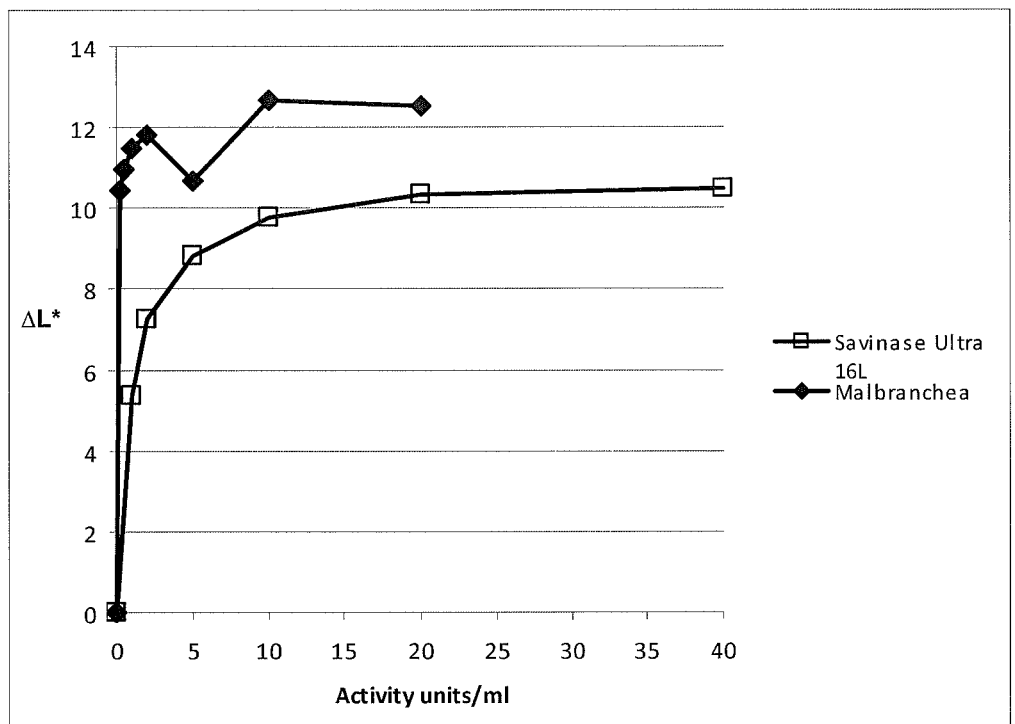
FIG. 9E shows performance on Blood/milk/ink, CO+PES, Art. 117 (Serial No. 11-08, new batch), EMPA at 30° C.
Figure 9F:
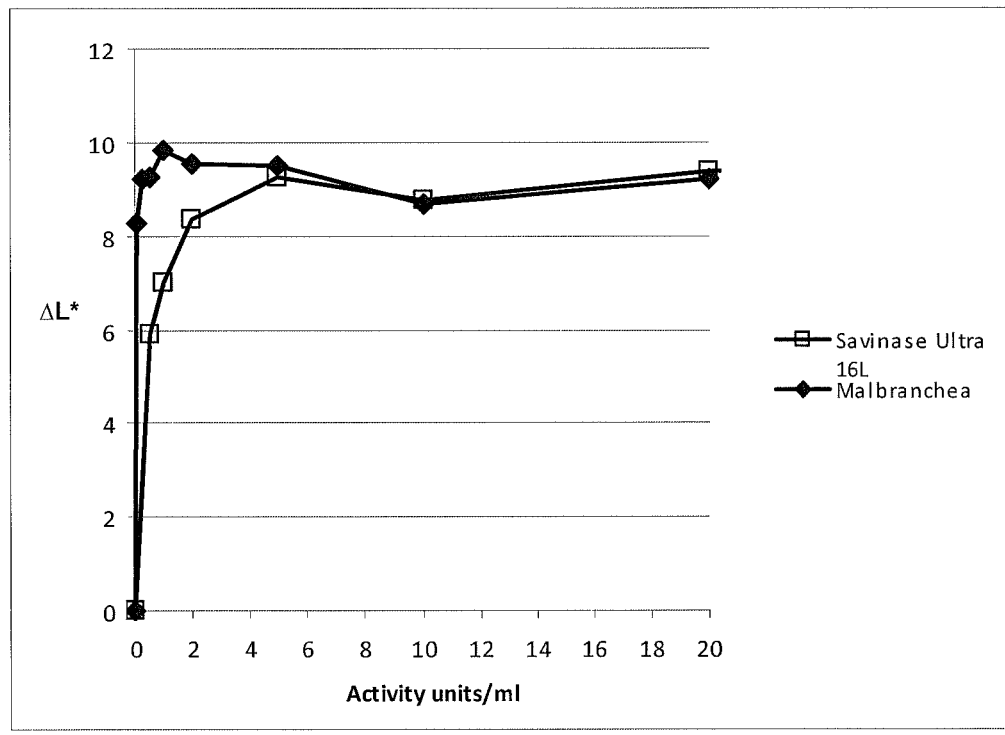
FIG. 9F shows performance on Blood/milk/ink, CO+PES, Art. 117 (Serial No. 11-08, new batch), EMPA at 60° C.
Figure 9G:
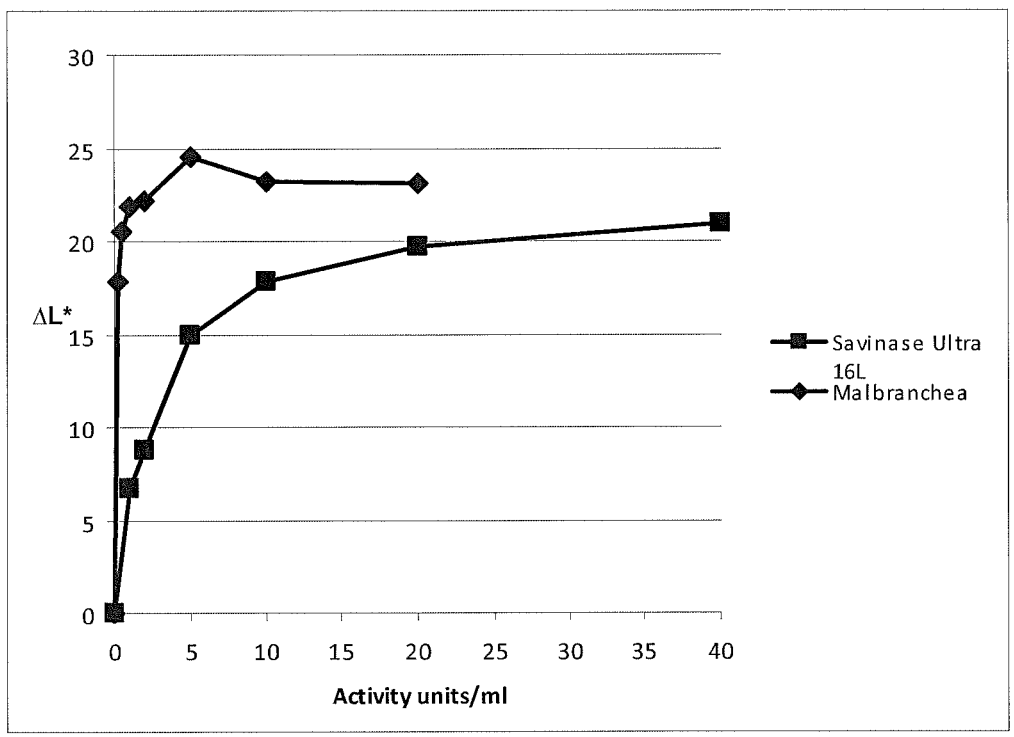
FIG. 9G shows performance on Blood/milk/ink, CO+PES, Art. 117 (Serial No. 10-07, old batch), EMPA at 30° C.
Figure 9H:
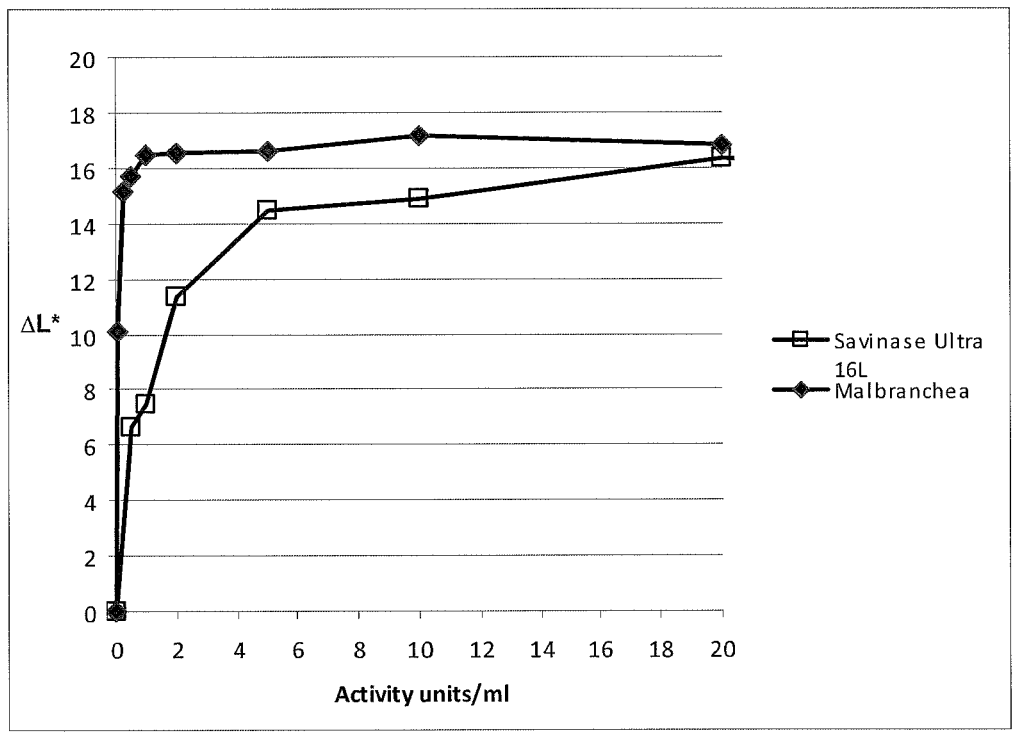
FIG. 9H shows performance on Blood/milk/ink, CO+PES, Art, 117 (Serial No. 10-07, old batch), EMPA at 60° C.
Figure 10A:
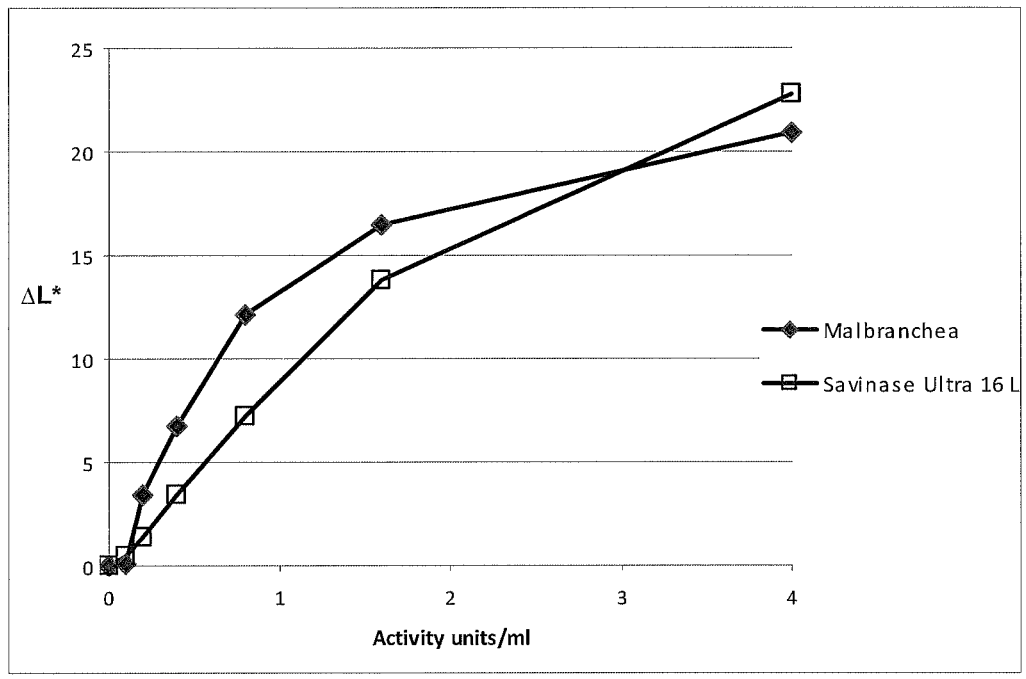
FIG. 10A describes the performance of recombinant Malbranchea ALKO4122 protease on Blood/milk/ink, CO+PES, Art. 117 (Serial No. 11-08), EMPA in the presence of Commercial traditional detergent powder (described in Example 8) 5 g/l at 50° C., 60 min, pH approx. 10.5. Savinase® Ultra 16L was used for comparison.
Figure 10B:
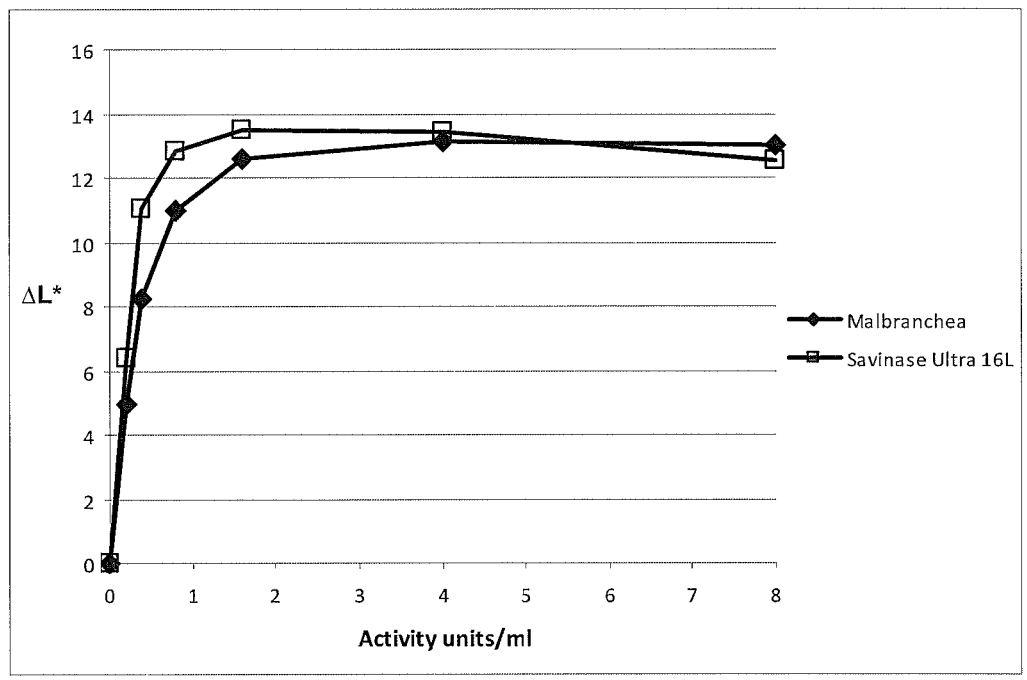
FIG. 10B describes the performance of recombinant Malbranchea ALKO4122 protease on Blood/milk/ink, CO+PES, Art. 117 (Serial No. 11-08), EMPA in the presence of detergent powder Art. 601, EMPA 5 g/l, 50° C., 60 min, pH approx. 10. Savinase® Ultra 16L was used for comparison.

The pH profile of the *Malbranchea* protease and Savinase® 16L were determined at 50° C. using casein as a substrate as described in Example 3, except that enzyme samples were diluted and casein was dissolved in 40 mM Britton-Robinson buffer, the pH of the reaction was adjusted to pH 6-10, the reaction time was 30 min and the enzyme reactions were stopped using a 0.11 M TCA solution which contained 0.22 M sodium acetate and 0.33 M acetic acid. The results are shown in FIG. 5B. The recombinant protease exhibits relative activity over 50% from pH 6 to pH 10 with best activity around pH 10.

Example 6

Stain Removal Performance of *Malbranchea* ALKO4122 Protease with Liquid Detergent at Different Temperatures

*Malbranchea* ALKO4122 protease produced in *Trichoderma*, as described in Example 2 (b) was tested for its ability to remove blood/milk/ink standard stain at 10, 20, 30 and 50° C. in the presence of Commercial liquid detergent (Table 3), at concentration of 5 g/l.

Standard stain, artificially soiled test cloth Art. 117 (blood/milk/ink, polyester+cotton, Serial No 11-08 or 10-07, EMPA Testmaterialen AG, Switzerland) was used as test material. Commercial protease preparations Savinase® 16L and Savinase® Ultra 16L (contains a protease inhibitor, 4-FBPA) and treatment without enzyme (control) were used for comparison. Each enzyme preparation was dosed 0-8 or 0-16 activity units (µg tyrosine/min) per ml wash liquor. Activity was measured as described in Example 3.

TABLE 3

| Composition of Commercial liquid detergent. | |
|---|---|
| Ingredient | % |
| Anionic surfactants | 15-30 |
| Nonionic surfactants, soap | 5-15 |
| Phosphonate, polycarboxylate | 5 |
| Optical brighteners and perfumes | |
| pH 8.2-8.6 | |

5 g of Commercial liquid detergent was dissolved in 1 liter of tap water (dH≤4), mixed well with magnetic stirrer and tempered to washing temperature. The pH in the wash liquor was approx. 8. The stain fabric was first cut in to 1.5 cm×1.5 cm swatches and the pieces were made rounder by cutting the corners. Pieces were placed in wells of microtiter plates (Nunc 150200). Into each well having a diameter of 2 cm, 1.5 ml wash liquor containing detergent and enzyme dilution in water (approx. 50 µl) was added on top of the fabric. The plates with samples were in incubated in Infors Ecotron incubator shaker at 10, 20, 30 and 50° C. for 60 min with 130 rpm. After that the swatches were carefully rinsed under running water (appr. at washing temperature) and dried overnight at indoor air, on a grid, protected against daylight.

The stain removal effect was evaluated by measuring the colour as reflectance values with Minolta CM 2500 spectrophotometer using L*a*b* colour space coordinates (illuminant D65/2°). The colour from both sides of the swatches was measured after the treatment. Each value was the average of at least 2 parallel fabric samples measured from both side of the fabric. Fading of blood/milk/ink stain, indicating the protease performance (stain removal efficiency), was calculated as ΔL* (delta L*), which means lightness value L* of enzyme treated fabric minus lightness value L* of fabric treated with washing liquor without enzyme (enzyme blank, control).

The results shown in FIGS. 6A-6D indicate that *Malbranchea* ALKO4122 protease has considerably better effect on blood/milk/ink stain (Art. 117, Serial No 11-08) at all temperatures tested compared to commercial Savinase® preparations. It was noticed that older batch (Serial No 10-07) of blood/milk/ink stain was more difficult to remove without enzyme (with detergent only), and therefore the enzyme contribution (ΔL*) was significantly higher compared to tests performed with newer batch 11-08. *Malbranchea* preparation of was even more efficient on this difficult old stain material compared to Savinase® (FIGS. 7A-7D). Also if dosing is calculated as amount of added protein (FIGS. 8A-8D), the stain removal efficiency was highest with *Malbranchea sulfurea* ALKO4122 protease. The amount of protein from the enzyme preparations was determined by Bio-Rad protein assay (Bio-Rad Laboratories, Hercules, Calif.) using bovine gammaglobulin (Bio-Rad) as standard.

It is surprising that *Malbranchea* ALKO4122 protease shows optimal stain removal performance at very broad temperature range and especially at low temperatures, like 10-30° C., despite of its high temperature optimum at analytical conditions on casein substrate (approx. 70° C., FIG. 5A). Savinase® that has similar temperature profile in analytical conditions (FIG. 5A) shows clearly lower performance at cold washing temperatures. The results of these tests indicate that *Malbranchea* ALKO4122 protease has excellent performance with liquid detergent at broad temperature range and even at very cold washing temperatures.

Example 7

Launder Tests of *Malbranchea* ALKO 4122 Protease with Liquid Detergent and Different Stains

*Malbranchea* ALKO4122 protease produced in *Trichoderma*, as described in Example 2 (b), was tested for its ability to remove different stains with Commercial liquid detergent at 30 and 60° C. compared to commercial protease preparation Savinase® Ultra 16L. The following artificially soiled test cloths from EMPA were used: blood/milk/ink (Art. 117, Serial No 11-08 and 10-07, polyester+cotton), blood/milk/ink (Art. 116, Serial No. 18-16, cotton), grass (Art. 164, Serial No. 23-03, cotton) and cocoa (Art. 112, Serial No. 31-06, cotton). The fabric was cut in 6 cm×6 cm swatches and the edges were neated by zig-zag stitches.

Stain removal treatments were performed in LP-2 Launder Ometer as follows. Launder Ometer was first preheated to 30 or 60° C. Then 0, 2, 5, 10 and 20 (40) activity units of enzyme per ml wash liquor was added into 1.2 liter containers containing 250 ml of tempered wash liquor and the stain swatches. Activity (μg tyrosine/min) was measured as described in Example 3. The wash liquor contained 5 g Commercial liquid detergent (Table 3) per liter tap water (dH≤4) and its pH was approx. 8. The Launder Ometer was run at 30° C. for 60 min with a rotation speed of 42 rpm. After that the swatches were carefully rinsed under running water (ca. 20° C.) and dried overnight at indoor air, on a grid, protected against daylight.

The colour of the swatches after treatment was measured with Minolta CM 2500 spectrophotometer using L*a*b* color space coordinates and stain removal effect calculated as ΔL* as described in Example 6. The colour from both sides of the swatches was measured after the treatment. Each value was the average of at least 12 measurements per swatch. The measurements were avoided from areas with crease marks formed during the treatment because of the folding of the fabric (in cotton stains Art. 116 and Art. 112).

The results shown in FIGS. 9A-9H indicate that *Malbranchea sulfurea* ALKO4122 protease has better effect on grass stain (Art. 164, Serial No. 23-03) and different blood/milk/ink stains (Art. 117, Serial No 11-08 and 10-07, Art. 116, Serial No 18-16) both at 30 and 60° C. compared to commercial protease preparation Savinase® Ultra16L. The dosage of 10-20 units of Savinase® Ultra 16L per was liquor was equal to dosage of approximately 0.4-0.7% of enzyme preparation per weight of detergent, which is in typical use level range for detergent enzymes.

Also results obtained with cocoa stain were better with *Malbranchea* compared to Savinase® Ultra 16L (data not shown). In additional Launder tests (data not shown) *Malbranchea* protease was found to be effective at 30° C. also on the following stains of CFT (Center for Testmaterials BV, The Netherlands: Groundnutoil, pigments, high milk (C-10), Egg yolk, pigment, aged (CS-38), Grass extract (CS-08)). Same commercial liquid detergent was used in all the tests. Results of these tests indicate that *Malbranchea* protease is efficient on several stains at broad temperature range 30-60° C.

Example 8

Stain Removal Performance of *Malbranchea* ALKO4122 Protease with Detergent Powders The ability of *Malbranchea* ALKO4122 protease produced in *Trichoderma* to remove blood/milk/ink standard stain in the presence of detergent (5 g/l) was tested at 50° C. using similar test system as described in Example 7, except Commercial traditional detergent powder containing bleaching agents, optical brighteners and phosphates/phosphonates and ECE reference detergent 77 without optical brightener and bleaching agents (Art. 601, EMPA) were used. Also the colour of the swatches after treatment was measured with Minolta CM 2500 spectrophotometer using L*a*b* colour space coordinates and stain removal effect calculated as ΔL* as described in Example 6.

Results (FIGS. 10A and 10B) show that *Malbranchea* ALKO4122 protease can also be used with detergent powders at highly alkaline conditions (pH approx. 10-10.5).

Example 9

Storage Stability of *Malbranchea* ALKO4122 Protease

Storage of *Malbranchea* ALKO4122 protease produced in *Trichoderma* at 37° C. was tested using the following formulation recipes: 1) 0.2% (w/w) Proxel LV (preservative, Arch Biosides, U.K), pH adjusted to 6, 2) 20% propylene glycol, pH adjusted 6, 3) 50% propylene glycol, pH adjusted 5.5. The samples of were packed in Sarstedt's test tubes (13 ml) and incubated at 37° C. Activity was measured (as described in Example 3) at certain intervals and compared to earlier results obtained with *Fusarium* protease Fe_RF6318 (WO2010125174A1) at similar conditions.

Figure 11B:
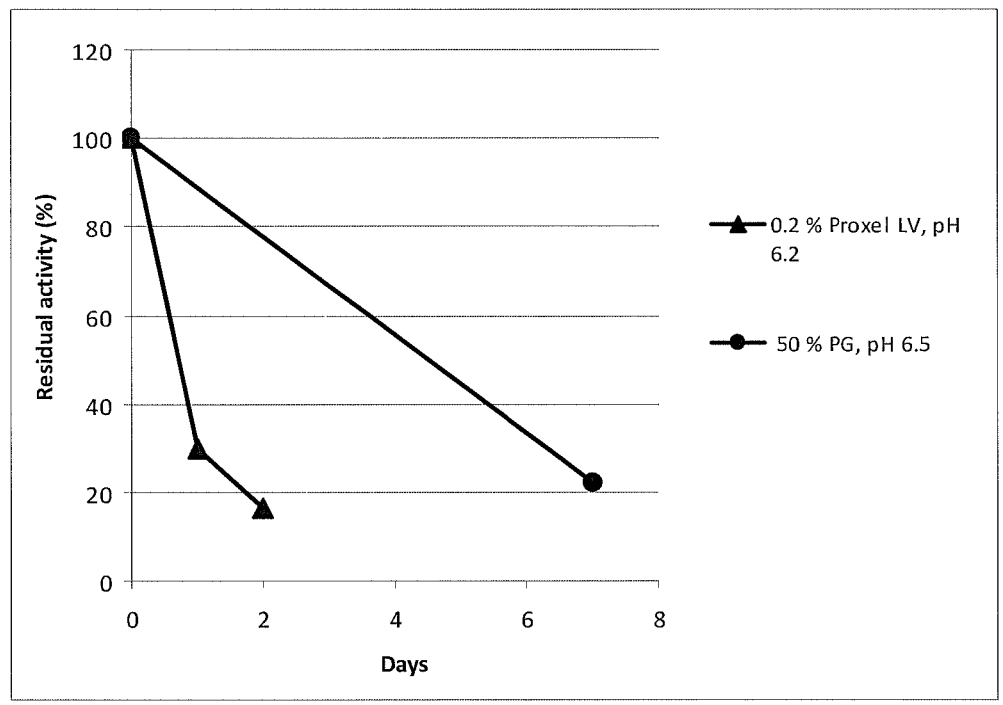
FIG. 11B shows the stability of recombinant protease Fe_RF6318 (WO2010125174A1) during storage at 37° C., when preserved/stabilized with Proxel LV or propylene glycol.

FIG. 11 shows that *Malbranchea* ALKO4122 protease has excellent storage stability at elevated temperatures (37° C.) compared to wild type *Fusarium* protease Fe_RF6318. When propylene glycol was used for stabilization, the residual activity of *Fusarium* protease was about 20% after 7 days incubation, whereas *Malbranchea* protease had not lost activity in that time.

Example 10

Stability of *Malbranchea* ALKO4122 Protease in Liquid Detergents

Stability of *Malbranchea* ALKO4122 protease produced in *Trichoderma* at 37° C. was tested in Commercial liquid detergent (Table 3) and Ecolabel Reference Detergent, light duty (Ch. Nr. 196-391, wfk Testgewebe GmbH). Savinase® 16L and *Fusarium* protease Fe_RF6318 (WO2010125174A1) were used as references.

The following test systems were used: 0.4 g enzyme preparation and 9.6 g of detergent solution were mixed well in Sarstedt's test tubes (13 ml). 0.2% of Proxel LV was added as preservative in detergent before mixing it with other components. The pH value of the samples prepared in Commercial liquid detergent was approx. 8. pHs of the samples prepared in Ecolabel Reference Detergent were approx. 7.2. Test tubes were incubated at 37° C. and the protease activity was measured at certain intervals according to the method described in Example 3.

FIG. 12 shows that *Malbranchea* ALKO4122 has very good storage stability at elevated temperatures (37° C.) in liquid detergents compared to wild type *Fusarium* protease Fe_RF6318 (WO2010125174A1). *Malbranchea* protease had similar stability compared to Savinase® 16L in Ecolabel Reference Detergent.

At room temperature an excellent stability was observed (data not shown).

REFERENCES

Altschul S F, W Gish, W Miller, E W Myers and D J Lipman. 1990. Basic local alignment search tool. J. Mol. Biol. 215: 403-410.

AMFEP, 2009. Association of Manufacturers and Formulators of Enzyme products, List of enzymes at www.amfep.org/list.html (updated October 2009).

Anwar, A and M Saleemuddin. 1998. Alkaline proteases: A review. Bioresource Technology 64:175-183.

Bolton, E T and B J McCarthy. 1962. A general method for the isolation of RNA complementary to DNA. Proc. Nat. Acad. Sci. USA 48:1390-1397.

Chen, Y-J, and M Inouye, 2008. The intramolecular chaperone-mediated protein folding. Curr. Opin. Struct. Biol. 18: 765-770.

Cherry, J. R., and Fidantsef, A. L. 2003. Directed evolution of industrial enzymes: an update. Curr. Opin. Biotechnol. 14: 438-443.

Gasteiger, E, A Gattiker, C Hoogland, I Ivanyi, R D Appel and A Bairoch. 2003.

Gaucher G M, Stevenson K J 2004. Thermomycolin. Handbook of Proteolytic Enzymes $2^{nd}$ Ed.: 1834-1835

ExPASy: The proteomics server for in-depth protein knowledge and analysis. Nucleic Acids Res. 31:3784-3788.

Gupta, R, Q K Beg, S Khan and B Chauhan. 2002. An overview on fermentation, downstream processing and properties of microbial alkaline protease. Appl. Microbiol. Biotechnol. 60: 381-395.

Gurr, S J, Uncles, S E, and Kinghorn J R. 1987. The structure and organization of nuclear genes in filamentous fungi. pp 93-139. In (J R Kinghorn, ed.) Gene Structure in Eukaryotic Microbes. IRL Press, Oxford.

Joutsjoki, V V, T K Torkkeli, and K M H Nevalainen. 1993. Transformation of *Trichoderma reesei* with the *Hormoconis resinae* glucoamylase P (gamP) gene: production of a heterologous glucoamylase by *Trichoderma reesei*. Curr. Genet. 24:223-228.

Kalisz, H M. 1988. Microbial proteinases. Adv. Biochem. Eng. Biotechnol. 36:1-65.

Karhunen T, A Mantyla, K M H Nevalainen, and P L Suominen. 1993. High frequency one-step gene replacement in *Trichoderma reesei*. I. Endoglucanase I overproduction. Mol. Gen. Genet. 241:515-522.

Kelly and Hynes 1985. Transformation of *Aspergillus niger* by the amdS gene of *Aspergillus nidulans*. The EMBO Journal 4(2):475-479.

Laemmli, U K. 1970. Cleavage of structural proteins during the assembly of the head of bacteriophage T4. Nature 227: 680-685.

Malardier L, M J Daboussi, J Julien, F Roussel, C Scazzocchio and Y Brygoo, 1989. Cloning of the nitrate reductase gene (niaD) of *Aspergillus nidulans* and its use for transformation of *Fusarium oxysporum*. Gene 78:147-156.

Maurer, K-H. 2004. Detergent proteases. Curr. Opin. Biotechnol. 15: 330-334.

Maurer, K-H, 2010. Enzymes, Detergent. pp. 1-17. In (M C Flickinger ed.) Encyclopedia of Industrial Biotechnology: Bioprocess, Bioseparation, and Cell Technology, John Wiley & Sons, Inc.

Nielsen H, J Engelbrecht, S Brunak and G von Heijne. 1997. Identification of prokaryotic and eukaryotic signal peptides and prediction of their cleavage sites. Protein Engineering 10:1-6.

Nielsen H and A Krogh. 1998. Prediction of signal peptides and signal anchors by a hidden Markov model. In: Proceedings of the Sixth International Conference on Intelligent Systems for Molecular Biology (ISMB 6), AAAI Press, Menlo Park, Calif., pp. 122-130.

Ong P H and Gaucher G M, 1975. Production, purification and characterization of thermomycolase, the extracellular serine protease of the thermophilic fungus *Malbranchea pulchella* var. *sulfurea*. Can. J. Microbiol. 22: 165-175.

Penttilä M, H Nevalainen, M Rättö, E Salminen, and J. Knowles. 1987. A versatile transformation system for the cellulolytic filamentous fungus *Trichoderma reesei*. Gene 61:155-164.

Raeder U and P Broda. 1985. Rapid preparation of DNA from filamentous fungi. Lett. Appl. Microbiol. 1:17-20.

Rao, M B, A M Tanksale, M S Ghatge and V V Deshpande. 1998. Molecular and biotechnological aspects of microbial proteases. Microbiol. Mol. Biol. Rev. 62:597-635.

Sambrook J and D W Russell. 2001. Molecular cloning, a laboratory manual. Cold Spring Harbor Laboratory, New York, US.

Shimogaki, H, K Takenchi, T. Nishino, M. Ohdera, T. Kudo, K. Ohba, M V Iwama and M Irie. 1991. Purification and properties of a novel surface active agent and alkaline-resistant protease from *Bacillus* sp. Y. Agric. Biol. Chem. 55:2251-2258.

The invention claimed is:

1. A method for removing a stain from a stained material, the method comprising contacting the stained material with a polypeptide comprising a serine protease enzyme consisting of an amino acid sequence at least 85% identical to the sequence set forth in SEQ ID NO:18.

2. A method for degrading or removing proteinaceous material from the surface of a solid water-insoluble carrier, the method comprising contacting the proteinaceous material with a polypeptide comprising a serine protease enzyme consisting of an amino acid sequence at least 85% identical to the sequence set forth in SEQ ID NO:18.

3. A method of preparing a detergent, comprising adding a polypeptide comprising a serine protease enzyme consisting of an amino acid sequence at least 85% identical to the sequence set forth in SEQ ID NO:18 as a detergent additive to a detergent selected from the group consisting of a liquid detergent, a detergent powder, and a detergent tablet.

4. A method of converting fibrous protein waste into useful biomass, the method comprising contacting the fibrous protein waste with a polypeptide comprising a serine protease enzyme consisting of an amino acid sequence at least 85% identical to the sequence set forth in SEQ ID NO:18.

5. The method of claim 1, wherein the stain is selected from the group consisting of blood, milk, ink, grass, cocoa, groundnut oil, egg yolk, food, and a body secretion.

6. The method of claim 1, wherein the stained material is a dish or a cloth.

7. The method of claim 1, wherein the polypeptide is in a composition comprising an additive selected from the group consisting of a stabilizer, a surfactant, a builder, a bleaching agent, a mediator, an anti-corrosion agent, an antiredeposition agent, a caustic, an abrasive, an optical brightener, a dye, a perfume, a pigment, and a preservative.

8. The method of claim 7, wherein the additive is a stabilizer.

9. The method of claim 8, wherein the stabilizer is a polyol.

10. The method of claim 1, wherein the polypeptide comprises a serine protease enzyme consisting of an amino acid sequence that is at least 90% identical, at least 95% identical at least 98%, at least 99% identical, or 100% identical to the sequence set forth in SEQ ID NO:18.

11. The method of claim 2, wherein the polypeptide is in a composition comprising an additive selected from the group consisting of a stabilizer, a surfactant, a builder, a bleaching agent, a mediator, an anti-corrosion agent, an antiredeposition agent, a caustic, an abrasive, an optical brightener, a dye, a perfume, a pigment, and a preservative.

12. The method of claim 11, wherein the additive is a stabilizer.

13. The method of claim 12, wherein the stabilizer is a polyol.

14. The method of claim 2, wherein the polypeptide comprises a serine protease enzyme consisting of an amino acid sequence that is at least 90% identical, at least 95% identical at least 98%, at least 99% identical, or 100% identical to the sequence set forth in SEQ ID NO:18.

15. The method of claim 3, wherein the polypeptide comprises a serine protease enzyme consisting of an amino acid sequence that is at least 90% identical, at least 95% identical at least 98%, at least 99% identical, or 100% identical to the sequence set forth in SEQ ID NO:18.

16. The method of claim 4, wherein the fibrous protein waste is selected from the group consisting of horns, feathers, nails, and hair.

17. The method of claim 4, wherein the polypeptide comprises a serine protease enzyme consisting of an amino acid sequence that is at least 90% identical, at least 95% identical at least 98%, at least 99% identical, or 100% identical to the sequence set forth in SEQ ID NO:18.

18. A method for degrading a proteinaceous material selected from the group consisting of wool, hair, leather, silk, food, and feed, the method comprising contacting the proteinaceous material with a polypeptide comprising a serine protease enzyme consisting of an amino acid sequence at least 85% identical to the sequence set forth in SEQ ID NO:18 for a sufficient time to achieve at least partial degradation of the proteinaceous material.

19. The method of claim 18, wherein the polypeptide comprises a serine protease enzyme consisting of an amino acid sequence that is at least 90% identical, at least 95% identical at least 98%, at least 99% identical, or 100% identical to the sequence set forth in SEQ ID NO:18.

* * * * *